US008067228B2

(12) United States Patent
Fournillier et al.

(10) Patent No.: US 8,067,228 B2
(45) Date of Patent: Nov. 29, 2011

(54) NUCLEIC ACID COMPOSITIONS AND THEIR USE AGAINST THE HEPATITIC C VIRUS

(75) Inventors: Anne Fournillier, Lyons (FR); Nourredine Himoudi, Lyons (FR); Genevieve Inchauspe, Lyons (FR)

(73) Assignees: Transgene SA, Illkirch Graffenstaden (FR); INSERM (Institut National de la Sante et de la Recherche Medicale), Paris (FR)

(*) Notice: Subject to any disclaimer, the term of this patent is extended or adjusted under 35 U.S.C. 154(b) by 382 days.

(21) Appl. No.: 12/211,385

(22) Filed: Sep. 16, 2008

(65) Prior Publication Data

US 2009/0087449 A1 Apr. 2, 2009

Related U.S. Application Data

(62) Division of application No. 12/132,321, filed on Jun. 3, 2008, which is a division of application No. 10/514,762, filed as application No. PCT/FR03/01478 on May 15, 2003, now Pat. No. 7,393,831.

(30) Foreign Application Priority Data

May 17, 2002 (FR) ..................................... 02 06111

(51) Int. Cl.

| | |
|---|---|
| ***A61K 31/711*** | (2006.01) |
| ***A61K 31/7115*** | (2006.01) |
| ***A61K 39/29*** | (2006.01) |
| ***C12N 1/00*** | (2006.01) |
| ***C12N 1/19*** | (2006.01) |
| ***C12N 1/21*** | (2006.01) |
| ***C12N 5/10*** | (2006.01) |
| ***C12N 15/00*** | (2006.01) |
| ***C12N 15/11*** | (2006.01) |
| ***C12N 15/63*** | (2006.01) |

(52) U.S. Cl. ......... 435/320.1; 435/6; 435/325; 435/348; 424/189.1; 424/228.1

(58) Field of Classification Search ....................... None
See application file for complete search history.

(56) References Cited

U.S. PATENT DOCUMENTS

| | | | |
|---|---|---|---|
| 5,106,726 | A | 4/1992 | Wang |
| 5,436,126 | A | 7/1995 | Wang |
| 5,582,968 | A | 12/1996 | Wang et al. |
| 5,639,594 | A | 6/1997 | Wang et al. |
| 5,683,864 | A | 11/1997 | Houghton et al. |
| 5,712,087 | A | 1/1998 | Houghton et al. |
| 5,736,321 | A | 4/1998 | Hosein et al. |
| 5,747,239 | A | 5/1998 | Wang et al. |
| 6,150,087 | A | 11/2000 | Chien |
| 6,312,889 | B1 | 11/2001 | Houghton et al. |
| 6,346,375 | B1 | 2/2002 | Chien |
| 6,534,482 | B1 | 3/2003 | Fikes et al. |
| 6,562,346 | B1 | 5/2003 | Paliard et al. |
| 6,635,257 | B1 | 10/2003 | Depla et al. |
| 7,393,831 | B2 | 7/2008 | Fournillier et al. |
| 2002/0115061 | A1 | 8/2002 | Chisari et al. |
| 2003/0095980 | A1 | 5/2003 | Maertens et al. |
| 2003/0118603 | A1 | 6/2003 | Maertens et al. |
| 2003/0194747 | A1 | 10/2003 | Georges et al. |
| 2003/0202987 | A1 | 10/2003 | Depla et al. |
| 2003/0203869 | A1 | 10/2003 | Fikes et al. |
| 2007/0020285 | A1 | 1/2007 | Fournillier et al. |
| 2007/0072176 | A1 | 3/2007 | Inchauspe et al. |

FOREIGN PATENT DOCUMENTS

| | | | |
|---|---|---|---|
| EP | 0 388 232 | A1 | 9/1990 |
| EP | 0 450 931 | A2 | 4/1991 |
| EP | 0 468 527 | A2 | 7/1991 |
| EP | 1506225 | B1 | 7/2006 |
| WO | WO 93/00365 | A | 1/1993 |
| WO | WO 94/20127 | | 9/1994 |
| WO | WO 99/58658 | A2 | 11/1999 |
| WO | WO 99/67285 | A | 12/1999 |
| WO | WO 01/21189 | A1 | 3/2001 |
| WO | WO 01/30812 | A3 | 5/2001 |
| WO | WO 01/90197 | A1 | 11/2001 |
| WO | WO 01/92311 | | 12/2001 |
| WO | WO 02/070006 | A2 | 9/2002 |
| WO | WO 03/097677 | A2 | 11/2003 |

OTHER PUBLICATIONS

Eck SL and Wilson JM, "Gene-Based Therapy," Goodman & Gilman's The Pharmaological basis of Therapeutics, McGraw-Hill, New Yor, NY. 1996, 77-101.*

Verma IM and Somia N, "Gene therapy-promises, problems and prospects," Nature, 1997, 389: 239-242.*

Pfeifer A and Verma IM, "Gene Therapy: Promises and Problems," Annual Review of Genomics and Human Genetics, 2001, 2:177-211).*

Kato N, Hijikata M, Ootsuyama Y, Nakagawa M, Ohkoshi S, Sugimura T, Shimotohno K, "Molecular cloning of the human hepatitis C virus genome from Japanese patients with non-A, non-B hepatitis," Proc. Natl. Acad. Sci. USA, 1990, 87: 9524-9528.*

U.S. Appl. No. 12/132,321, filed Jun. 3, 2008, Fournillier et al.

Abrams et al., "Generation of Stable CD4 and CD8 T-cell Lines from Patients Immunized with ras Oncogene-Derived Peptides Reflecting Codon 12 Mutations," *Cell. Immunol.* 182:137-151, 1997.

Battegay et al., "Patients with Chronic Hepatitis C Have Circulating Cytotoxic T-cells Which Recognize Hepatitis C Virus-Encoded Peptides Binding to HLA-A2.1 Molecules," *J. Virol.* 69:2462-2470, 1995.

(Continued)

*Primary Examiner* — Julie Ha
(74) *Attorney, Agent, or Firm* — Clark & Elbing LLP

(57) ABSTRACT

Peptide compositions are described. In particular, peptide compositions are described which include at least two peptides which are selected from among the following peptides: a peptide A having at least the amino acid sequence of SEQ ID N° 1, a peptide B having at least the amino acid sequence of SEQ ID N° 45, a peptide C having at least the amino acid sequence of SEQ ID N° 127, and a peptide D having at least the amino acid sequence of SEQ ID N° 174. The compositions can be used, in particular, in the preparation of active pharmaceutical compositions against the hepatitis C virus.

26 Claims, 13 Drawing Sheets

OTHER PUBLICATIONS

Brinster et al., "Different Hepatitis C Virus Nonstructural Protein 3 (NS3)-DNA-Expressing Vaccines Induce in HLA-A2.1 Transgenic Mice Stable Cytotoxic T Lymphocytes that Target One Major Epitope," *Hepatology* 34:1206-1217, 2001.
Chang et al., "Identification of HLA-A3 and -B7-Restricted CTL Response to Hepatitis C Virus in Patients with Acute and Chronic Hepatitis C," *J. Immunol.* 162:1156-1164, 1999.
Definition of "epitope," in *Immunobiology,* 4th Edition, p. 600, 1999.
Diepolder et al., "Immunodominant $CD4^+$ T-cell Epitope Within Nonstructural Protein 3 in Acute Hepatitis C Virus Infection," *J. Virol.* 71:6011-6019, 1997.
Fournillier et al., "Primary and Memory T Cell Responses Induced by Hepatitis C Virus Multiepitope Long Peptides," *Vaccine* 24:3153-3164, 2006.
Fytili et al., "Cross-Genotype-Reactivity of the Immunodominant HCV CD8 T-cell Epitope NS3-1073," *Vaccine,* online publication, Jun. 2008.
Heile et al., "Evaluation of Hepatitis C Virus Glycoprotein E2 for Vaccine Design: An Endoplasmic Reticulum-Retained Recombinant Protein is Superior to Secreted Recombinant Protein and DNA-based Vaccine Candidates," *J. Virol.* 74:6885-6892, 2000.
Himoudi et al., "Comparative Vaccine Studies in HLA-A2.1-Transgenic Mice Reveal a Clustered Organization of Epitopes Presented in Hepatitis C Virus Natural Infection," *J. Virol.* 76:12735-12746, 2002.
Kozeil et al., "Hepatitis C Virus (HCV)-Specific Cytotoxic T Lymphocytes Recognize Epitopes in the Core and Envelope Proteins of HCV," *J. Virol.* 367:7522-7532, 1993.
Lamonaca et al., "Conserved Hepatitis C Virus Sequences are Highly Immunogenic for $CD4^+$ T Cells: Implications for Vaccine Development," *Hepatology* 30:1088-1098, 1999.
Lechner et al., "Analysis of Successful Immune Responses in Persons Infected with Hepatitis C Virus," *J. Exp. Med.* 191:1499-1512, 2000.
Leroux-Roels, "Development of Prophylactic and Therapeutic Vaccines Against Hepatitis C Virus," *Expert Rev. Vaccines* 4:351-371, 2005.
Manns et al., "The Way Forward in HCV Treatment- Finding the Right Path," *Nature Rev. Drug Discov.* 6:991-1000, 2007.
Martin et al., "Genetic Immunization and Comprehensive Screening Approaches in HLA-A2 Transgenic Mice Lead to the Identification of Three Novel Epitopes in Hepatitis C Virus NS3 Antigen," *J. Med. Virol.* 74:397-405, 2004.
Martin et al., "A Vector-Based Minigene Vaccine Approach Results in Strong Induction of T-cell Responses Specific of Hepatitis C Virus," *Vaccine* 26:2471-2481, 2008.
Pancholi et al., "DNA Immunization with Hepatitis C Virus (HCV) Polycistronic Genes or Immunization by HCV DNA Priming-Recombinant Canarypox Virus Boosting Induces Immune Responses and Protection from Recombinant HCV-Vaccinia Virus Infection in HLA-A2.1-Transgenic Mice," *J. Virol.* 77:382-390, 2003. Abstract only.
Pascolo et al., "HLA-A2.1-Restricted Education and Cytolytic Activity of $CD8^+$ T Lymphocytes from β2 Microglobulin (β2m) HLA-A2.1 Monochain Transgenic H-$2D^b$ β2m Double Knockout Mice," *J. Exp. Med.* 185:2043-2051, 1997.
Puig et al., "$CD4^+$ Immune Escape and Subsequent T-cell Failure Following Chimpanzee Immunization Against Hepatitis C Virus," *Hepatology* 44:736-745, 2006.
Qiao et al., "Hepatitis C Virus-Like Particles Combined with Novel Adjuvant Systems Enhance Virus-Specific Responses," *Hepatology* 37:52-59, 2003. Abstract only.
Racanelli et al., "Dendritic Cells Transfected with Cytopathic Self-Replicating RNA Induce Crossprinting of $CD8^+$ T Cells and Antiviral Immunity," *Immunity* 20:47-58, 2004. Abstract only.
Rollier et al., "Control of Heterologous Hepatitis C Virus Infection in Chimpanzees is Associated with the Quality of Vaccine-Induced Peripheral T-Helper Immune Response," *J. Virol.* 78:187-196, 2004.
Rudikoff et al., "Single Amino Acid Substitution Altering Antigen-Binding Specificity," *Proc. Natl. Acad. Sci. U.S.A.* 79:1979-1983, 1982.
Shirai et al., "An Epitope in Hepatitis C Virus Core Region Recognized by Cytotoxic T cells in Mice and Humans," *J. Virol.* 68:3334-3342, 1994.
Simon et al., "DNA Vaccination Protects Mice Against Challenge with *Listeria monocytogenes* Expressing the Hepatitis C Virus NS3 Protein," *Infect. Immun.* 71:6372-6380, 2003.
Spaulding et al., "Analysis of Murine CD8(+) T-cell Clones Specific for the Dengue Virus NS3 Protein: Flavivirus Cross-Reactivity and Influence of Infecting Serotype," *J. Virol.* 73:398-403, 1999.
Sutter et al., "Nonreplicating Vaccinia Vector Efficiently Expresses Recombinant Genes," *Proc. Natl. Acad. Sci. U.S.A.* 89:10847-10851, 1992.
Tabatabai et al., "Functionally Distinct T-cell Epitopes Within the Hepatitis C Virus Non-Structural 3 Protein," *Human Immunol.* 60:105-115, 1999.
Wedemeyer et al., "Cross-Reactivity Between Hepatitis C Virus and Influenza A Virus Determinant-Specific Cytotoxic T Cells," *J. Virol.* 75:11392-11400, 2001. Abstract only.
Wedemeyer et al., "Oral Immunization with HCV-NS3-Transformed *Salmonella:* Induction of HCV-Specific CTL in a Transgenic Mouse Model," *Gastroenterology* 121:1158-1166, 2001. Abstract only.
Wong et al., "Liver-Derived CTL in Hepatitis C Virus Infection: Breadth and Specificity of Responses in a Cohort of Persons with Chronic Infection," *J. Immunol.* 160:1479-1488, 1998.
"Annex 1: Additional Results Submitted by the Inventors" filed with the European Patent Office for European Patent Application No. EP 03752815.5 on Jan. 14, 2008.
International Search Report for PCT/FR03/01478, Nov. 11, 2003.
Substantive prosecution documents from U.S. Appl. No. 11/503,245, filed Aug. 11, 2006.
Chang et al., "Immunological Significance of Cytotoxic T Lymphocyte Epitope Variants in Patients Chronically Infected by the Hepatitis C Virus," J. Clin. Invest. 100:2376-2385, 1997.
Ibe et al., "Identification and Characterization of a Cytotoxic T Cell Epitope of Hepatitis C Virus Presented by HLA-B*3501 in Acute Hepatitis," J. Gen Virol. 79:1735-1744, 1998.
Kato et al., "Molecular Cloning of the Human Hepatitis C Virus Genome from Japanese Patients with Non-A, Non-B Hepatitis," Proceedings of the National Academy of Sciences of the United State of America 87:9524-9528, 1990.
Ward et al., "Cellular Immune Responses Against Hepatitis C Virus: The Evidence Base 2002," Clin. Exp. Immunol. 128:195-203, 2002.
Wertheimer et al., "Novel $CD4^+$ and $CD8^+$ T-Cell Determinants Within the NS3 Protein in Subjects with Spontaneously Resolved HCV Infection," Hepatol. 37:577-589, 2003.
International Preliminary Examination Report for PCT/FR03/01478, Oct. 28, 2004 (and English language translation thereof).
Day et al., "Broad Specificity of Virus-Specific $CD4^+$ T-Helper-Cell Responses in Resolved Hepatitis C Virus Infection," J. Virol. 76:12584-12595, 2002.
Substantive prosecution documents from U.S. Appl. No. 10/514,762, filed Nov. 16, 2004 (now U.S. Patent No. 7,393,831).

* cited by examiner

Figure 2

Shimotono:

```
STKVPAAYAAQGYKVRVLNPSVAATLGFGAYMSKAHGIEPNIRTGV
```

1a :

```
---------------L----------------------D-------  50% (7/14)
---------------L---------------------VD-------  50% (7/14)
```

1b: /135

```
STKVPAAYAAQGYKVRVLNPSVAATLGFGAYMSKAHGIEPNIRTGV
---------------L---------------------VD-------  29% (39/135)
---------------L----------------------D-------  28% (38/135)
---------------L---------------------TD-------   6% (9/135)
---------------L-------------------Y-TD-------   6% (8/135)
---------------L------------------------------   4% (6/135)
---------------L----------S----------TD-------   4% (5/135)
---------------L-------------------Y--D--V---- 1,5% (2/135)
---------------------------------------------- 1,5% (2/135)
---------------L---------------------T-------- 1,5% (2/135)
-N---VE--------L---------------------VD------- 1,5% (2/135)
---------------L------T--------------VD------- 1,5% (2/135)
---------G-----L----------------------D------- 1,5% (2/135)
---------------L----------S-----------D------- 1,5% (2/135)
--R------------L----------------------D--L---- 1,5% (2/135)
---------T-----L---------------------TD------- 1,5% (2/135)
---------------L----------------------D--V---- 1,5% (2/135)
---------------L----------S----------VD-S----- 1,5% (2/135)
---------------L---------------------VD---S--- 0,8% (1/135)
---------------L-------------------Y-TD--V---- 0,8% (1/135)
---------T-----L----------S--------Y-MD--L---- 0,8% (1/135)
---------------L----------S----------VD----- 0,8% (1/135)
---------------L----------S--------Y-VD------- 0,8% (1/135)
--R------------L---------------------TD------- 0,8% (1/135)
--R------------L----------S--------Y-VD------- 0,8% (1/135)
--R------------L-------------T-----Y-TD------- 0,8% (1/135)
```

4:

```
STKVPAAYAAQGYKVRVLNPSVAATLGFGAYMSKAHGIEPNIRTGV
-------H-------L-------------V-----Y--D----S-- 100% (1/1)
```

Figure 3A

Shimotono:

```
APITAYSQQTRGLLGCIITSLTGRDKNQVDGEVQVLSTATQSFLATCVNGVCWTVYHGAGSKT
```

```
------A----------------------E----IV---A-T-----I------------TR- 93% (13/14)
------T----------------------E----IV-----T-----I------------TR-  7% (1/14)
```

```
-----------------------------E-----V--------------------------- 24%(32/136)
-------------------------R---E-----V--------------------------- 11%(15/136)
-----------------------------E-----V-----------I--------------- 10%(13/136)
---------------------------------------------------------------  5%(7/136)
-------------F---------------E-----V---------------------------  3%(4/136)
------------V---V------------E-----V-----------I---------------  3%(4/136)
-----------------------------E-----V--------------A----F-------  3%(4/136)
-------R---------------------E-----V---------------------------  2%(3/136)
-----------------------------E-----V-----------I-------F----A--  2%(3/136)
-----------------------------E-----V-----------I-------F-------  2%(3/136)
------------V----------------E-----V-----------I---------------  2%(3/136)
------A----------------------E-----V-------------------F-------  2%(3/136)
-----------------V-----------E-----V--------------A----F-------  2%(3/136)
------A-----V----------------E-----V-------------------F------- 1,5%(2/136)
-----------------------------------------------I--------------- 1,5%(2/136)
-----------------------------E-----V--------------A------------ 1,5%(2/136)
------------V----------------E-----V----H------I--------------- 1,5%(2/136)
-----------------------------E-----V-----------I--A------------ 1,5%(2/136)
-----------------------------E-----V---------S----------------- 1,5%(2/136)
-----------------------------E-----V-----------T--------------- 1,5%(2/136)
------------V----------------E-----V--------------------------- 1,5%(2/136)
-----------------------------E-----V---K-----------------------0,75%(1/136)
------C----------------------E-----V---------------------------0,75%(1/136)
-----------------------------E-----V---K----------A------------0,75%(1/136)
-----------------------------E-----V------------------------T--0,75%(1/136)
-----------------------------E-----V-----T-------------F-------0,75%(1/136)
-----------------------------E-----V--------------A---------T--0,75%(1/136)
-----------------------------E-----V-------------------F----T--0,75%(1/136)
-----------------------------E----EV--------------------------I0,75%(1/136)
-------------F---V-----------E--A--V---------------------------0,75%(1/136)
-------------F---------------E-----V-----------I---------------0,75%(1/136)
```

```
--------------F---V-----------E--A--V--------------A------------0,75%(1/136)
-------------V----------------E-----V-------------------F-------0,75%(1/136)
-------------V----------------E-----V---------------------------0,75%(1/136)
----T-------------------------E-----V------------------------T--0,75%(1/136)
-S-----------V---V------------E-----V-----------I---------------0,75%(1/136)
-S----------------V-----------E-----V-------------------F-------0,75%(1/136)
------A-----------V-----------E-----V-------------------F-------0,75%(1/136)
------A-----------------------E-----V-----------I---------------0,75%(1/136)
------A------F-----------R---E-----V-----------I---------------0,75%(1/136)
------A------F---------------E-----V-----------I---------------0,75%(1/136)
--------------------------R---E-----V-----------I-------F-------0,75%(1/136)
--------------------------R---E-----V------------------------A--0,75%(1/136)
-H------------------------R---E----MV---------------------------0,75%(1/136)
```

```
------X------FST----------T-ENC--------------G-A----M--------A-- 100%(1/1)
```

Figure 4

Shimotono:

```
NFITGIQYLAGLSTLPGNPAIASLMAFTASITSPLTTQNTLLFNILGGWVAAQLAPP
```

1a:

```
---S-------------------------AV------SQ----------------A-  50% (7/14)
---S-------------------------AV------GQ----------------A-  43% (6/14)
---S-T-----------------------AV------SQ----------------A-   7% (1/14)
```

1b:

```
NFITGIQYLAGLSTLPGNPAIASLMAFTASITSPLTTQNTLLFNILGGWVAAQLAPP
---S----------------------------------H------------------35%(48/139)
---S----------------------------------S------------------18%(25/139)
---S-----------------------------------------------------16%(22/139)
---S----------------------------------------------------- 6%(9/139)
---S----------------------------------Y------------------ 6%(8/139)
---S-----------------V----------------H------------------ 2%(3/139)
---S--------------------------V-------------------------- 2%(3/139)
---S--------------------------V-------S------------------ 2%(3/139)
---S----------------------------------T--M---------------1,5%(2/139)
---S--------------------------V-------Y--------------I---1,5%(2/139)
---S-----------------R-P--------------H------------------1,5%(2/139)
---S--------------------------------I-H--------------P---0,8%(1/139)
---S------A---------------------------------------------A0,8%(1/139)
---S------------------------S---------S------------------0,8%(1/139)
---S-------------------------------S---------W-----------0,8%(1/139)
---S-------------------------------------M---------------0,8%(1/139)
---S----------------M-----------------H--M---------------0,8%(1/139)
---S-V---------------------------------------------------0,8%(1/139)
---S-V--------------------------------H------------------0,8%(1/139)
---S-V--------------------------------Y------------------0,8%(1/139)
---S-V------------------------V-------S------------------0,8%(1/139)
---S--------------L-------------------H------------------0,8%(1/139)
---S-------------------------------A--Y------------------0,8%(1/139)
```

4:

```
NFITGIQYLAGLSTLPGNPAIASLMAFTASITSPLTTQNTLLFNILGGWVAAQLAPP

---S---------------------S---AV-------Q------------S-IRDS 100% (1/1)
```

Figure 5

Shimotono:

```
KGGRKPARLIVFPDLGVRVCEKMALYDVVSTLPQAVMGPSYGFQ
```

1a:

```
------------------------------K--L----S----- 57% (8/14)
------------------------------K--P----S----- 21% (3/14)
-----------------------------TK--L----S----- 21% (3/14)
```

1b:

```
--------------------------------------S----- 68% (97/142)
-------------------------------------------- 10% (15/142)
--------------------------------------A-----  3% (5/142)
----------------------------------V---S-----  2% (3/142)
---Q----------------------------------S----- 1,5% (2/142)
-----A--------------------------------S----- 1,5% (2/142)
------------------------------I-------S----- 1,5% (2/142)
-------------E------------------------S----- 1,5% (2/142)
--------F------------------------K----S----- 0,8% (1/142)
--------F-----------------------------S----- 0,8% (1/142)
---------------------------------R----S---C- 0,8% (1/142)
----------------------------------P---S----- 0,8% (1/142)
---------------------------------H----S----- 0,8% (1/142)
--------------------------------------SA---- 0,8% (1/142)
--------------------------------------S--R-- 0,8% (1/142)
-----A-------------------------------------- 0,8% (1/142)
-----A--------------------N-----------S----- 0,8% (1/142)
------------------------------N-------S----- 0,8% (1/142)
-------------E------------------------------ 0,8% (1/142)
---------------------------------H----S----- 0,8% (1/142)
---------------------------------HT---S----- 0,8% (1/142)
-----------Y--------------------------S----- 0,8% (1/142)
```

4:

```
-----------Y----S-----R--H--IKKTAL----AA---- 100% (1/1)
```

NUCLEIC ACID COMPOSITIONS AND THEIR USE AGAINST THE HEPATITIC C VIRUS

CROSS-REFERENCE TO RELATED APPLICATIONS

This application is a divisional of, and claims priority from, U.S. Ser. No. 12/132,321, filed Jun. 3, 2008, which is a divisional of U.S. Ser. No. 10/514,762, filed Nov. 16, 2004, which is a U.S. national stage application under 35 U.S.C. §371 of PCT/FR03/01478, filed May 15, 2003, which claims priority from French Application No. 02/06111, filed May 17, 2002.

A subject of the present invention is novel peptide compositions and their use in particular in the preparation of pharmaceutical compositions active against the hepatitis C virus.

A subject of the present invention is a peptide composition useful in particular in prophylactic and therapeutic vaccination directed against the hepatitis C virus.

Hepatitis C is the main cause of hepatitis acquired by transfusion. Hepatitis C can also be transmitted by other percutaneous routes, for example by injection of drugs by intravenous route. The risk of contamination to health professionals is moreover not negligible.

Hepatitis C differs from the other forms of liver diseases associated with viruses, such as hepatitis A, B or D. Infections by the hepatitis C virus (HCV) are mostly chronic, resulting in liver diseases, such as hepatitis, cirrhosis and carcinoma in a large number of cases (5 to 20%).

Although the risk of transmission of the virus by transfusion has diminished due to the establishment of screening tests in the 1990s, the frequency of hepatitis C remains high. By way of example, a recent study indicates that today there are still 10,000 to 15,000 new cases of infection per year in France (S. Deuffic et al., Hepatology 1999; 29: 1596-1601). At present, approximately 170 million people world-wide are chronically infected by HCV. Populations at high risk are chiefly hospital staff and intravenous-drug users, but asymptomatic blood donors exist who do not belong to these high-risk groups and in whom circulating anti-HCV antibodies have been found. For the latter, the infection route has not yet been identified.

HCV was the first hepatotropic virus isolated by means of molecular biology techniques. The sequences of the viral genome were cloned before the viral particle was visualized.

HCV belongs to a novel group of the Flaviviridae family, the hepaciviruses. This is a virus with a single positive RNA strand, of 9.5 kb, which is replicated by a copy of complementary RNA and the translation product of which is a precursor of a single polyprotein of approximately 3,000 amino acids. The 5' end of the HCV genome corresponds to a non-translated region adjacent to the genes which code for the structural proteins, the core protein of the nucleocapsid, the two envelope glycoproteins, E1 and E2, and a small protein called p7. The non-translated 5' region and the core gene are relatively well preserved in the different genotypes. The envelope proteins E1 and E2 are encoded by more variable regions from one isolate to another. The protein p7 is an extremely hydrophobic protein the function of which is not known. The 3' end of the HCV genome contains the genes which code for the non-structural proteins (NS2, NS3, NS4, NS5) and for a non-coding 3' region possessing a well-preserved domain (Major M E, Feinstone S M, Hepatology, June 1997, 25(6): 1527-1538).

Therapy for the treatment of hepatitis C which is the current focus of attention is a dual therapy using pegylated interferon and ribavirin (Manns M P et al., The Lancet, 22 Sep. 2001, Vol. 358, 958-965). Whilst this therapy is particularly effective in the case of patients infected by viral strains belonging to genotypes 2 and 3, it only has a limited effect on genotypes 1a, 1b and 4 (Manns M P, above).

It is therefore necessary to develop a vaccine composition targeting these poorly-responsive genotypes as a priority.

Several studies today show that the control of an infection caused by HCV, either naturally ("spontaneous resolution"), or after treatment ("therapeutic resolution") is associated with the induction or potentialization of cell-mediated immune responses involving the T-$CD4^+$ and T-$CD8^+$ lymphocytes (CERNY A et al., J. Clin. Invest., 95: 521-530 (1995)).

The object of vaccines based on the use of peptides is generally to induce immune responses mediated by the T-CD4+ and/or T-CD8+ lymphocytes.

The molecules of the major histocompatibility complex (MHC) are described as class I or class II. Class I molecules are expressed on virtually all of the nucleated cells and can be the target of $CD8^+$ cytotoxic T lymphocytes (CTLs). The CTLs recognize the peptides or epitopes which are presented in association with the MHC molecules of class I.

For example, the class I molecule HLA-A2.1 indicates that the binding site of the peptide is created by bringing together the domains $\alpha_1$ and $\alpha_2$ of the heavy chain of class I (Bjorkaman et al., Nature, 329: 506 (1987)).

Certain authors have concluded the immunogenic power of peptide preparations on the basis of their good binding scores on HLA molecules, as in the Patent Application WO01/21189.

Such a deduction is not evident and can lead:

either to the selection of peptides having no immunogenic power, although having a high binding score, as demonstrated by the Applicant in Example 1 of the present Application with the FLAT peptide, or to the elimination of peptides which are in fact very immunogenic, as shown with the CIN peptide in Brinster C. et al. (Hepatology, Vol. 34, NO 6, 2001, 1206-1217). In fact, although the CIN peptide has an average, or even low (335), binding score, it is nevertheless capable of inducing a strong response mediated by cytotoxic T lymphocytes.

The Applicant has now unexpectedly found that a novel peptide composition containing at least two peptides chosen from the A to D peptides had a strong immunogenic power and had an effect on the ability of the cells originating from patients infected by viral strains of genotype 1a, 1b and 4 to induce specific immune responses. These patients preferably, but not limitatively, have an HLA of type HLA-A2.1.

Thus, a subject of the present invention is the peptide compositions comprising at least two compounds chosen from:

an A peptide having at least the following amino acid sequence SEQ ID NO: 1:

$X_1AX_2QGYKVX_3VLNPSVX_4ATLX_5FGX_6YMSKAX_7GX_8$, in which $X_1$ is Y or H, $X_2$ is A, G or T, $X_3$ is R or L, $X_4$ is A or T, $X_5$ is G or S, $X_6$ is A, T or V, $X_7$ is H or Y and $X_8$ is I, T, M or V, a B peptide having at least the following amino acid sequence SEQ ID NO: 45:

$GX_{18}X_{19}X_{20}X_{21}X_{22}X_{23}TSLTGRDX_{24}NX_{25}X_{26}X_{27}GEX_{28}QX_{29}X_{30}STAX_{31}X_{32}X_{33}FLX_{34}$ $X_{35}X_{36}X_{37}NGX_{38}X_{39}WTVX_{40}$ in which $X_{18}$ is L or V, $X_{19}$ is L or F, $X_{20}$ is G or S, $X_{21}$ is C or T, $X_{22}$ is I or V, $X_{23}$ is I or V, $X_{24}$ is K, R or T, $X_{25}$ is Q or E, $X_{26}$ is V or N, $X_{27}$ is D, E or C, $X_{28}$ is V or A, $X_{29}$ is V, L E or M, $X_{30}$ is L or V, $X_{31}$ is T, K or A, $X_{32}$ is Q or H, $X_{33}$ is S or T, $X_{34}$ is A or G, $X_{35}$ is T or S, $X_{36}$ is C or A, $X_{37}$ is V, I or T, $X_{38}$ is V or A, $X_{39}$ is C or M and $X_{40}$ is Y or F, a C peptide having at least the following amino acid sequence SEQ ID NO: 127:

$SX_{47}MX_{48}FTX_{49}X_{50}X_{51}TSPLX_{52}X_{53}X_{54}X_{55}TLX_{56}FNIX_{57}GGWVAX_{58}QX_{59}$ in which $X_{47}$ is L or P, $X_{48}$ is A or S, $X_{49}$ is A or S, $X_{50}$ is A or S, $X_{51}$ is I or V, $X_{52}$ is T, S or A, $X_{53}$ is T or, $X_{54}$ is Q, S or G, $X_{55}$ is N, Q, H, S, Y or T, $X_{56}$ is L or M, $X_{57}$ is L or W, $X_{58}$ is A or S and $X_{59}$ is L, P or I, and a D peptide having at least the following amino acid sequence SEQ ID NO: 174:

$X_{69}KX_{70}ARX_{71}IVX_{72}PX_{73}LGX_{74}RVCEKX_{75}ALX_{76}X_{77}VX_{78}X_{79}$ $X_{80}X_{81}$ in which $X_{69}$ is R or Q, $X_{70}$ is P or A, $X_{71}$ is L or F, $X_{72}$ is F or Y, $X_{73}$ is D or E, $X_{74}$ is V or S, $X_{75}$ is M or R, $X_{76}$ is Y or H, $X_{77}$ is D or N, $X_{78}$ is V or I, $X_{79}$ is S, T or K, $X_{80}$ is T, K, I or N and $X_{81}$ is L or T, a B' epitope having the following sequence SEQ ID NO: 213:

$GX_{18}X_{19}X_{20}X_{21}X_{22}X_{23}TSL$ in which $X_{18}$ is L or V, $X_{19}$ is L or F, $X_{20}$ is G or S, $X_{21}$ is C or T, $X_{22}$ is I or V and $X_{23}$ is I or V, and a C' epitope having the following sequence SEQ ID NO: 221:

$SPLX_{52}X_{53}X_{54}X_{55}TL$ in which $X_{52}$ is T, S or A, $X_{53}$ is T or I, $X_{54}$ is Q, S or G and $X_{55}$ is N, Q, H, S, Y or T, as well as the pharmaceutical compositions containing them and their use, in particular as vaccine, for the preparation of a medicament intended for the inhibition or prevention of an infection caused by the hepatitis C virus, and as a diagnostic composition.

A particular subject of the invention is a peptide composition as defined above, characterized in that it comprises at least two peptides chosen from the A, B, C, D peptides.

A subject is also the particular A, B, C, D peptides, the nucleotide sequences coding for said peptides and the microorganisms or host cells cotransformed by these vectors.

Finally a subject is the antibodies directed against the compositions of the invention and a process for detection and/or quantification of the hepatitis C virus in a biological sample using said antibodies.

The peptide compositions of the invention, having a strong immunogenic power against the genotypes 1a, 1b and 4 of the hepatitis C virus, therefore contain at least two peptides chosen from the A to D peptides as defined above.

The A peptide is included in the non-structural protein 3 (NS3) between positions 1244 and 1274 of the polyprotein encoded by the HCV virus.

The B peptide is also included in the protein NS3 between positions 1038 and 1082 of the viral polyprotein.

The C peptide is included in the non-structural protein NS4 between positions 1789 and 1821 of said viral polyprotein.

As for the D peptide, it is included in the non-structural protein NS5b between positions 2573 and 2601 of said viral polyprotein.

Of course, by peptide is meant the peptide as such, as well as its homologues having at least 60%, preferably at least 70%, still more preferably at least 80%, better at least 90% and still better 95% homology with the peptide of interest.

The A to D peptides were obtained from the strain HCV-JA (Kato L., et al., (1990), Proc. Natl. Acad. Sci. USA, 87(24), 9524-9528) otherwise called the Shimotohno strain. They contain known epitopes but, as indicated previously, these epitopes do not necessarily have a high binding score.

The binding score is obtained by prediction, using software, of the ability of known or potential epitope sequences (peptide sequences) to bind to the HLA molecule of interest. This score can be included in a range from negative values to the value of approximately 1000 and by high binding score is meant a binding score greater than or equal to 600.

On the other hand, unexpectedly, the combination of the A to D peptides of the invention makes it possible to induce specific cytotoxic T lymphocytes capable of a vigour and effectiveness greater than that obtained with each of the peptides used separately and/or each of the individual epitopes contained in these peptides used alone or in combination as well as stimulating a higher production of γ interferon.

Moreover, these peptides are capable of inducing specific T lymphocytes having cross-reactivity.

According to one embodiment of the invention, the compositions of the invention contain two peptides according to the following combinations: A and B peptides, A and C peptides, A and D peptides, B and C peptides, B and D peptides and C and D peptides.

The preferred compositions contain the A and B, A and C, B and D, and C and D peptides, the compositions containing the A and B, C and D, and B and D peptides being more preferred.

According to another embodiment, the compositions of the invention contain three peptides according to the following combinations: A, B and D peptides, A, C and D peptides, and B, C and D peptides, the compositions comprising the A, B and C, A, C and D, and B, C and D peptides being particularly preferred.

According to yet another embodiment, the compositions of the invention contain the four A, B, C, D peptides.

The A peptide in the compositions of the invention has at least the amino acid sequence SEQ ID NO: 1 as described above.

According to one embodiment of the invention, the A peptide has at most the 46 amino acids as described in the following sequence SEQ ID NO: 2:

$SX_9X_{10}VPX_{11}X_{12}X_1AX_2QGYKVX_3VLNPSVX_4ATLX_5FGX_6YMSKAX_7GX_8X_{13}PX_{14}X_{15}X_{16}X_{17}GV$, in which $X_1$ to $X_8$ are as defined previously, and $X_9$ is T or N, $X_{10}$ is K or R, $X_{11}$ is A or V, $X_{12}$ is A or E, $X_{13}$ is E or D, $X_{14}$ is N or S, $X_{15}$ is I, L or V, $X_{16}$ is R or S and $X_{17}$ is T or S.

In this case, the A peptide is situated between positions 1237 and 1282 of the viral polyprotein.

According to yet another embodiment, the A peptide is chosen from the following peptides:

the peptides having at least sequence SEQ ID NO: 3, which corresponds to sequence SEQ ID NO: 1 in which $X_1$ is Y, $X_2$ is A, $X_3$ is R, $X_4$ is A, $X_5$ is G, $X_6$ is A, $X_7$ is H and Xs is I, and at most sequence SEQ ID NO: 19 which corresponds to sequence SEQ ID NO: 2 in which $X_1$ to $X_8$ are as defined for sequence SEQ ID NO: 3 and $X_9$ is T, $X_{10}$ is K, $X_{11}$ is A, $X_{12}$ is A, $X_{13}$ is E, $X_{14}$ is N, $X_{15}$ is I, $X_{16}$ is R and $X_{17}$ is T, the peptides having at least sequence SEQ ID NO: 4 which corresponds to sequence SEQ ID NO: 1 in which $X_1$ is Y, $X_2$ is A, $X_3$ is L, $X_4$ is A, $X_5$ is G, $X_6$ is A, $X_7$ is H and $X_8$ is L and at most a sequence chosen from the following sequences:

i) sequence SEQ ID NO: 20 which corresponds to sequence SEQ ID NO: 2 in which $X_1$ to $X_8$ are as defined for sequence SEQ ID NO: 4 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, ii) sequence SEQ ID NO: 24 which corresponds to sequence SEQ ID NO: 2 in which $X_1$ to $X_8$ are as defined for sequence SEQ ID NO: 4 and $X_9$ is T, $X_{10}$ is K, $X_{11}$ is A, $X_{12}$ is A, $X_{13}$ is E, $X_{14}$ is N, $X_{15}$ is I, $X_{16}$ is R and $X_{17}$ is T, iii) sequence SEQ ID NO: 32 which corresponds to sequence SEQ ID NO: 2 in which $X_1$ to $X_8$ are as defined for sequence SEQ ID NO: 4 and $X_9$ is T, $X_{10}$ is R, $X_{11}$ is A, $X_{12}$ is A, $X_{13}$ is D, $X_{14}$ is N, $X_{15}$ is L, $X_{16}$ is R and $X_{17}$ is T, and iv) sequence SEQ ID NO: 34 which corresponds to sequence SEQ ID NO: 2 in which $X_1$ to $X_8$ are as defined for sequence SEQ ID NO: 4 and $X_9$ is T, $X_{10}$ is K, $X_{11}$ is A, $X_{12}$ is A, $X_{13}$ is D, $X_{14}$ is N, $X_{15}$ is V, $X_{16}$ is R and $X_{17}$ is T, the peptides having at least sequence SEQ ID NO: 5 which corresponds to sequence SEQ ID NO: 1 in which $X_1$ is Y, $X_2$ is A, $X_3$ is L, $X_4$ is A, $X_5$ is G, $X_6$ is A, $X_7$ is H and $X_8$ is V, and at most a sequence chosen from the following sequences:

i) sequence SEQ ED NO: 21 which corresponds to sequence SEQ ID NO: 2 in which $X_1$ to $X_8$ are as defined for sequence SEQ ID NO: 5 and $X_9$ is T, $X_{10}$ is K, $X_{11}$ is A, $X_{12}$ is A, $X_{13}$ is D, $X_{14}$ is N, $X_{15}$ is L $X_{16}$ is R and $X_{17}$ is T, ii) sequence SEQ ID NO: 28 which corresponds to sequence SEQ ID NO: 2 in which $X_1$ to $X_8$ are as defined for sequence SEQ ID NO: 5 and $X_9$ is N, $X_{10}$ is K, $X_{11}$ is V, $X_{12}$ is E, $X_{13}$ is D, $X_{14}$ is N, $X_{15}$ is I, $X_{16}$ is R and $X_{17}$ is T, and iii) sequence SEQ ID NO: 36 which corresponds to sequence SEQ ID NO: 2 in which $X_1$ to $X_8$ are as defined for sequence SEQ ID NO: 5 and $X_9$ is T, $X_{10}$ is K, $X_{11}$ is A, $X_{12}$ is A, $X_{13}$ is D, $X_{14}$ is N, $X_{15}$ is I, $X_{16}$ is S and $X_{17}$ is T, the peptides having at least sequence SEQ ID NO: 6 which corresponds to sequence SEQ ID NO: 1 in which $X_1$ is Y, $X_2$ is A, $X_3$ is L, $X_4$ is A, $X_5$ is G, $X_6$ is A, $X_7$ is H and $X_8$ is T, and at most a sequence chosen from the following sequences:

i) sequence SEQ ID NO: 22 which corresponds to sequence SEQ ID NO: 2 in which $X_1$ to $X_8$ are as defined for sequence SEQ ID NO: 6 and $X_9$ is T, $X_{10}$ is K, X is A, $X_{12}$ is A, $X_{13}$ is D, $X_{14}$ is N, $X_{15}$ is I, $X_{16}$ is R and $X_{17}$ is T, ii) sequence SEQ ID NO: 27 which corresponds to sequence SEQ ID NO: 2 in which $X_1$ to $X_8$ are as defined for sequence SEQ ID NO: 6 and $X_9$ is T, $X_{10}$ is K, $X_{11}$ is A, $X_{12}$ is A, $X_{13}$ is E, $X_{14}$ is N, $X_{15}$ is I, $X_{16}$ is R and $X_{17}$ is T, and iii) sequence SEQ ID NO: 41 which corresponds to sequence SEQ ID NO: 2 in which $X_1$ to $X_8$ are as defined for sequence SEQ ID NO: 6 and $X_9$ is T, $X_{10}$ is R, $X_{11}$ is A, $X_{12}$ is A, $X_{13}$ is D, $X_{14}$ is N, X is L $X_{16}$ is R and $X_{17}$ is T, the peptides having at least sequence SEQ ID NO: 7 which corresponds to sequence SEQ ID NO: 1 in which $X_1$ is Y, $X_2$ is A, $X_3$ is L, $X_4$ is A, $X_5$ is G, $X_6$ is A, $X_7$ is Y and $X_8$ is T, and at most a sequence chosen from the following sequences:

i) sequence SEQ ID NO: 23 which corresponds to sequence SEQ ID NO: 2 in which $X_1$ to $X_8$ are as defined for sequence SEQ ID NO: 7 and $X_9$ is T, $X_{10}$ is K, $X_{11}$ is A, $X_{12}$ is A, $X_{13}$ is D, $X_{14}$ is N, $X_{15}$ is N, $X_{16}$ is R and $X_{17}$ is T, and ii) sequence SEQ ID NO: 37 which corresponds to sequence SEQ ID NO: 2 in which $X_1$ to $X_8$ are as defined for sequence SEQ ID NO: 7 and $X_9$ is T, $X_{10}$ is K, $X_{11}$ is A, $X_{12}$ is A, $X_{13}$ is D, $X_{14}$ is N, $X_5$ is V, $X_{16}$ is R and $X_{17}$ is T, the peptides having at least sequence SEQ ID NO: 8 which corresponds to sequence SEQ ID NO: 1 in which $X_1$ is Y, $X_2$ is A, $X_3$ is L, $X_4$ is A, $X_5$ is S, $X_6$ is A, $X_7$ is H and $X_8$ is T, and at most sequence SEQ ID NO: 25 which corresponds to sequence SEQ ID NO: 2 in which $X_1$ to $X_8$ are as defined for sequence SEQ ID NO: 8 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 9 which corresponds to sequence SEQ ID NO: 1 in which $X_1$ is Y, $X_2$ is A, $X_3$ is L, $X_4$ is A, $X_5$ is G, $X_6$ is A, $X_7$ is Y and X is I, and at most sequence SEQ ID NO: 26 which corresponds to sequence SEQ ID NO: 2 in which $X_1$ to $X_8$ are as defined for sequence SEQ ID NO: 9 and $X_9$ is T, $X_{10}$ is K, X is A, $X_{12}$ is A, $X_{13}$ is D, $X_{14}$ is N, $X_{15}$ is V, $X_{16}$ is R and $X_{17}$ is T, the peptides having at least sequence SEQ ID NO: 10 which corresponds to sequence SEQ ID NO: 1 in which $X_1$ is Y, $X_2$ is A, $X_3$ is L, $X_4$ is T, $X_5$ is G, $X_6$ is A, $X_7$ is H and $X_8$ is V, and at most sequence SEQ ID NO: 29 which corresponds to sequence SEQ ID NO: 2 in which $X_1$ to $X_8$ are as defined for sequence SEQ ID NO: 10 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 11 which corresponds to sequence SEQ D NO: 1 in which $X_1$ is Y, $X_2$ is G, $X_3$ is L, $X_4$ is A, Xs is G, $X_6$ is A, $X_7$ is H and $X_8$ is I, and at most sequence SEQ ID NO: 30 which corresponds to sequence SEQ ID NO: 2 in which $X_1$ to $X_8$ are as defined for sequence SEQ ID NO: 11 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 12 which corresponds to sequence SEQ ID NO: 1 in which $X_1$ is Y, $X_2$ is A, $X_3$ is L, $X_4$ is A, $X_5$ is S, $X_6$ is A, $X_7$ is H and $X_8$ is I, and at most sequence SEQ ID NO: 31 which corresponds to sequence SEQ ID NO: 2 in which $X_1$ to $X_8$ are as defined for sequence SEQ ID NO: 12 and $X_9$ is T, $X_{10}$ is K, $X_{11}$ is A, $X_{12}$ is A, $X_{13}$ is D, $X_{14}$ is N, $X_{15}$ is L $X_{16}$ is R and $X_{17}$ is T, the peptides having at least sequence SEQ ID NO: 13 which corresponds to sequence SEQ ID NO: 1 in which $X_1$ is Y, $X_2$ is T, $X_3$ is L, $X_4$ is A, $X_5$ is G, $X_6$ is A, $X_7$ is H and $X_8$ is T, and at most sequence SEQ ID NO: 33 which corresponds to sequence SEQ ID NO: 2 in which $X_1$ to $X_8$ are as defined for sequence SEQ ID NO: 13 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 14 which corresponds to sequence SEQ ID NO: 1 in which $X_1$ is Y, $X_2$ is A, $X_3$ is L, $X_4$ is A, $X_5$ is S, $X_6$ is A, $X_7$ is H and $X_8$ is V, and at most a sequence chosen from the following sequences:

i) sequence SEQ ID NO: 35 which corresponds to sequence SEQ ID NO: 2 in which $X_1$ to $X_8$ are as defined for sequence SEQ ID NO: 14 and $X_9$ is T, $X_{10}$ is K, $X_{11}$ is A, $X_{12}$ is A, $X_{13}$ is D, $X_{14}$ is S, $X_{15}$ is I, $X_{16}$ is R and $X_{17}$ is T, and ii) sequence SEQ ID NO: 39 which corresponds to sequence SEQ ED NO: 2 in which $X_1$ to $X_8$ are as defined for sequence SEQ ID NO: 14 and $X_9$ is T, $X_{10}$ is K, $X_{11}$ is A, $X_{12}$ is A, $X_{13}$ is D, $X_{14}$ is N, $X_{15}$ is I, $X_{16}$ is R and $X_{17}$ is T, the peptides having at least sequence SEQ ID NO: 15 which corresponds to sequence SEQ ID NO: 1 in which $X_1$ is Y, $X_2$ is T, $X_3$ is L, $X_4$ is A, $X_5$ is S, $X_6$ is A, $X_7$ is Y and $X_8$ is M, and at most sequence SEQ ID NO: 38 which corresponds to sequence SEQ ID NO: 2 in which $X_1$ to $X_8$ are as defined for sequence SEQ ID NO: 15 and $X_9$ is T, $X_{10}$ is K, $X_{11}$ is A, $X_{12}$ is A, $X_{13}$ is D, $X_{14}$ is N, $X_{15}$ is L, $X_{16}$ is R and $X_{17}$ is T, the peptides having at least sequence SEQ ID NO: 16 which corresponds to sequence SEQ ID NO: 1 in which $X_1$ is Y, $X_2$ is A, $X_3$ is L, $X_4$ is A, $X_5$ is S, $X_6$ is A, $X_7$ is Y and $X_8$ is V, and at most a sequence chosen from the following sequences:

i) sequence SEQ ID NO: 40 which corresponds to sequence SEQ ID NO: 2 in which $X_1$ to $X_8$ are as defined for sequence SEQ ID NO: 16 and $X_9$ is T, $X_{10}$ is K, $X_{11}$ is A, $X_{12}$ is A, $X_{13}$ is D, $X_{14}$ is N, X is L, $X_{16}$ is R and $X_{17}$ is T, and ii) sequence SEQ ID NO: 42 which corresponds to sequence SEQ ID NO: 2 in which $X_1$ to $X_8$ are as defined for sequence SEQ ID NO: 16 and $X_9$ is T, $X_{10}$ is R, $X_{11}$ is A, $X_{12}$ is A, $X_{13}$ is D, $X_{14}$ is N, $X_{15}$ is I, $X_{16}$ is R and $X_7$ is T, the peptides having at least sequence SEQ ID NO: 17 which corresponds to sequence SEQ ID NO: 1 in which $X_1$ is Y, $X_2$ is A, $X_3$ is L, $X_4$ is A, $X_5$ is G, $X_6$ is $T_{17}$ is Y and $X_8$ is T, and at most sequence SEQ ID NO: 43 which corresponds to sequence SEQ ID NO: 2 in which $X_1$ to $X_8$ are as defined for sequence SEQ ID NO: 17 and $X_9$ is T, $X_{10}$ is R, X is A, $X_{12}$ is A, $X_{13}$ is D, $X_{14}$ is N, $X_{15}$ is I, $X_6$ is R and $X_{17}$ is T, and the peptides having at least sequence SEQ ID NO: 18 which corresponds to sequence SEQ ID NO: 1 in which $X_1$ is H, $X_2$ is A, $X_3$ is L, $X_4$ is A, $X_5$ is G, $X_6$ is V, $X_7$ is Y and $X_8$ is I, and at most sequence SEQ ID NO: 44 which corresponds to sequence SEQ ID NO: 2 in which $X_1$ to $X_8$ are as defined for sequence SEQ ID NO: 18 and $X_9$ is T, $X_{10}$ is K, $X_{11}$ is A, $X_{12}$ is A, $X_{13}$ is D, $X_{14}$ is N, X is I, $X_{16}$ is R and $X_{17}$ is S.

Preferably, the A peptide is chosen from the peptides of sequences SEQ ID NO: 3 to 18, the peptide of sequence SEQ ID NO: 3 being particularly preferred.

The B peptide in the compositions of the invention has at least the amino acid sequence SEQ ID NO: 45 as described above.

According to one embodiment, the B peptide has at most the 63 amino acids as described in the following sequence SEQ ID NO: 46:

$$AX_{41}ITX_{42}YX_{43}X_{44}QTRGX_{18}X_{19}X_{20}X_{21}X_{22}X_{23}TSLTGRDX_{24}NX_{25}X_{26}X_{27}GEX_{28}QX_{29}$$

$$X_{30}STAX_{31}X_{32}X_{33}FLX_{34}X_{35}X_{36}X_{37}NGX_{38}X_{39}WTVX_{40}HGAGX_{45}X_{46}X_{47}$$

in which $X_{18}$ to $X_{40}$ are as defined above and $X_{41}$ is P, S or H, $X_{42}$ is A or T, $X_{43}$ is S, A, T or C, $X_{44}$ is Q or R, $X_{45}$ is S, T or A, $X_{46}$ is K or R and $X_{47}$ is T or I.

In this case, the B peptide is situated between positions 1027 and 1089 of the viral polyprotein.

According to yet another embodiment the B peptide is chosen from the following peptides:

the peptides having at least sequence SEQ ED NO: 47 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is D, $X_{29}$ is V, $X_{29}$ is V, $X_{30}$ is L, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 81 which corresponds to sequence SEQ ID NO: 46 in which $X_{18}$ to $X_{40}$ are as defined for sequence SEQ ID NO: 47 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 48 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is I, $X_{30}$ is V, $X_{31}$ is A, $X_{32}$ is Q, $X_{33}$ is T, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 82 which corresponds to sequence SEQ ID NO: 46 in which $X_{18}$ to $X_{40}$ are as defined for sequence SEQ ID NO: 48 and $X_{41}$ is P, $X_{42}$ is A, $X_{43}$ is A, $X_{44}$ is Q, $X_{45}$ is T, $X_{46}$ is R and $X_{47}$ is T, the peptides having at least sequence SEQ ID NO: 49 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is I, $X_{30}$ is V, $X_{31}$ is T, $X_{32}$ is Q, $X_{33}$ is T, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 83 which corresponds to sequence SEQ ID NO: 46 in which $X_{18}$ to $X_{40}$ are as defined for sequence SEQ ID NO: 49 and $X_{41}$ is P, $X_{42}$ is A, $X_{43}$ is T, $X_{44}$ is Q, $X_{45}$ is T, $X_{46}$ is R and $X_{47}$ is T, the peptides having at least sequence SEQ ID NO: 50 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most a sequence chosen from the following sequences:

i) sequence SEQ ID NO: 84 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is S, $X_{44}$ is Q, $X_{45}$ is S, $X_{46}$ is K and $X_{47}$ is T, ii) sequence SEQ ID NO: 90 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is S, $X_{44}$ is R, $X_{45}$ is S, $X_{46}$ is K and $X_{47}$ is T, iii) sequence SEQ ID NO: 105 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is C, $X_{44}$ is Q, $X_{45}$ is S, $X_{46}$ is K and $X_{47}$ is T, iv) sequence SEQ ID NO: 107 which corresponds to sequence SEQ ID NO: 46 in which $X_{18}$ to $X_{40}$ are as defined for sequence SEQ ID NO: 50 and $X_{41}$ is P, $X_{42}$ is A, $X_{43}$ is S, $X_{44}$ is Q, $X_{45}$ is T, $X_{46}$ is K and $X_{47}$ is T, and v) sequence SEQ ID NO: 116 which corresponds to sequence SEQ ID NO: 46 in which $X_{18}$ to $X_{40}$ are as defined for sequence SEQ ID NO: 50 and $X_{41}$ is P, $X_{42}$ is T, $X_{43}$ is S, $X_{44}$ is Q, $X_{45}$ is T, $X_{46}$ is K and $X_{47}$ is T, the peptides having at least sequence SEQ ID NO: 51 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most a sequence chosen from the following sequences:

i) sequence SEQ ID NO: 85 which corresponds to sequence SEQ ID NO: 46 in which $X_{18}$ to $X_{40}$ are as defined for sequence SEQ ID NO: 51 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ID NO: 124 which corresponds to sequence SEQ ID NO: 46 in which $X_{18}$ to $X_{40}$ are as defined for sequence SEQ ID NO: 51 and $X_{41}$ is P, $X_{42}$ is A, $X_{43}$ is S, $X_{44}$ is Q, $X_{45}$ is A, $X_{46}$ is K and $X_{47}$ is T.

the peptides having at least sequence SEQ ID NO: 52 which corresponds to sequence SEQ ID NO: 45 in which $X_{18}$ is L, $X_{19}$ is L, $X_2O$ is G, $X_{21}$ is C, $X_{22}$ is I, $X_{23}$ is I, $X_{24}$ is K, $X_{25}$ is Q, $X_{26}$ is V, $X_{27}$ is E, $X_{29}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most a sequence chosen from the following sequences:

i) sequence SEQ ID NO: 86 which corresponds to sequence SEQ ID NO: 46 in which $X_{18}$ to $X_{40}$ are as defined for sequence SEQ ID NO: 52 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ID NO: 120 which corresponds to sequence SEQ ID NO: 46 in which $X_{18}$ to $X_{40}$ are as defined for sequence SEQ ID NO: 52 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 53 which corresponds to sequence SEQ ID NO: 45 in which $X_{18}$ is L, $X_{19}$ is F, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q. $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 87 which corresponds to sequence SEQ ID NO: 46 in which $X_{18}$ to $X_{40}$ are as defined for sequence SEQ ID NO: 53 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 54 which corresponds to sequence SEQ ID NO: 45 in which $X_{18}$ is V, $X_{19}$ is L, $X_{20}$ is G, $X_{21}$ is C, $X_{22}$ is V, $X_{23}$ is I, $X_{24}$ is K, $X_{25}$ is Q, $X_{26}$ is V, $X_{27}$ is B, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most a sequence chosen from the following sequences:

i) sequence SEQ ID NO: 88 which corresponds to sequence SEQ ID NO: 46 in which $X_1$ to $X_{40}$ are as defined for sequence SEQ ID NO: 54 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ID NO: 117 which corresponds to sequence SEQ ID NO: 46 in which $X_{18}$ to $X_{40}$ are as defined for sequence SEQ ID NO: 54 and $X_{41}$ is S, $X_{42}$ is A, $X_{43}$ is S, $X_{44}$ is Q, $X_{45}$ is S, $X_{46}$ is K and $X_{47}$ is T, the peptides having at least sequence SEQ ID NO: 55 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is F, and at most sequence SEQ ID NO: 89 which corresponds to sequence SEQ ID NO: 46 in which $X_{18}$ to $X_{40}$ are as defined for sequence SEQ ID NO: 55 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 56 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is F, and at most a sequence chosen from the following sequences:

i) sequence SEQ ID NO: 91 which corresponds to sequence SEQ ID NO: 46 in which $X_{18}$ to $X_{40}$ are as defined for sequence SEQ ID NO: 56 and $X_{41}$ is P, $X_{42}$ is A, $X_{43}$ is S, $X_{44}$ is Q, $X_{45}$ is A, $X_{46}$ is K and $X_{47}$ is T, and ii) sequence SEQ ID NO: 92 which corresponds to sequence SEQ ID NO: 46 in which $X_{18}$ to $X_{40}$ are as defined for sequence SEQ ID NO: 56 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 57 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 93 which corresponds to sequence SEQ ID NO: 46 in which $X_{18}$ to $X_{40}$ are as defined for sequence SEQ ID NO: 57 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 58 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is F, and at most a sequence chosen from the following sequences:

i) sequence SEQ ID NO: 94 which corresponds to sequence SEQ ID NO: 46 in which $X_{18}$ to $X_{40}$ are as defined for sequence SEQ ID NO: 58 and $X_{41}$ is P, $X_{42}$ is A, $X_{43}$ is A, $X_{44}$ is Q, $X_{45}$ is S, $X_{46}$ is K and $X_{47}$ is T, and ii) sequence SEQ ID NO: 110 which corresponds to sequence SEQ ID NO: 46 in which $X_{18}$ to $X_{40}$ are as defined for sequence SEQ ID NO: 58 and $X_{41}$ is P, $X_{42}$ is A, $X_{43}$ is S, $X_{44}$ is Q, $X_{45}$ is T, $X_{46}$ is K and $X_{47}$ is T, the peptides having at least sequence SEQ ID NO: 59 which corresponds to sequence SEQ ID NO: 45 in which $X_{18}$ is L, $X_{19}$ is L, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is F, and at most sequence SEQ ED NO: 95 which corresponds to sequence SEQ ID NO: 46 in which $X_{18}$ to $X_{40}$ are as defined for sequence SEQ ID NO: 59 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 60 which corresponds to sequence SEQ ID NO: 45 in which $X_{18}$ is V, X is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is F, and at most a sequence chosen from the following sequences:

i) sequence SEQ ID NO: 96 which corresponds to sequence SEQ ID NO: 46 in which $X_{18}$ to $X_{40}$ are as defined for sequence SEQ ID NO: 60 and $X_{41}$ is P, $X_{42}$ is A, $X_{43}$ is A, $X_{44}$ is Q, $X_{45}$ is S, $X_{46}$ is K and $X_{47}$ is T, and ii) sequence SEQ ID NO: 115 which corresponds to sequence SEQ ID NO: 46 in which $X_{18}$ to $X_{40}$ are as defined for sequence SEQ ID NO: 60 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 61 which corresponds to sequence SEQ ID NO: 45 in which $X_{18}$ is L, $X_{19}$ is L, $X_{20}$ is G, $X_{21}$ is C, $X_{22}$ is L $X_{23}$ is I, $X_{24}$ is K, $X_{25}$ is Q, $X_{26}$ is V, $X_{27}$ is D, $X_{28}$ is V, $X_{29}$ is V, $X_{30}$ is L, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 97 which corresponds to sequence SEQ ID NO: 46 in which $X_{18}$ to $X_{40}$ are as defined for sequence SEQ ID NO: 61 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 62 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is Y, and at most a sequence chosen from the following sequences:

i) sequence SEQ ID NO: 98 which corresponds to sequence SEQ ID NO: 46 in which $X_{18}$ to $X_{40}$ are as defined for sequence SEQ ID NO: 62 and $X_{41}$ is P, $X_{42}$ is A, $X_{43}$ is S, $X_{44}$ is Q, $X_{45}$ is S, $X_{46}$ is K and $X_{47}$ is T, and ii) sequence SEQ ED NO: 109 which corresponds to sequence SEQ ID NO: 46 in which $X_{18}$ to $X_{40}$ are as defined for sequence SEQ ID NO: 62 and $X_{41}$ is P, $X_{42}$ is A, $X_{43}$ is S, $X_{44}$ is Q, $X_{45}$ is T, $X_{46}$ is K and $X_{47}$ is T, the peptides having at least sequence SEQ ID NO: 63 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is H, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 99 which corresponds to sequence SEQ ID NO: 46 in which $X_{18}$ to $X_{40}$ are as defined for sequence SEQ ID NO: 63 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 64 which corresponds to sequence SEQ ID NO: 45 in which $X_{18}$ is L, $X_{19}$ is L, $X_{20}$ is G, $X_2$, is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is A, $X_{39}$ is C and $X_{40}$ is Y, and at most sequence SEQ ID NO: 100 which corresponds to sequence SEQ ID NO: 46 in which $X_{18}$ to $X_{40}$ are as defined for sequence SEQ ID NO: 64 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 65 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is S, $X_{36}$ is C, $X_{37}$ is V, $X_{38}$ is V, $X_{39}$ is C and $X_{40}$ is Y, and at most sequence SEQ ID NO: 101 which corresponds to sequence SEQ ID NO: 46 in which $X_{18}$ to $X_{40}$ are as defined for sequence SEQ ID NO: 65 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 66 which corresponds to sequence SEQ ID NO: 45 in a which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is T, $X_{38}$ is V, $X_{39}$ is C and $X_{40}$ is Y, and at most sequence SEQ ID NO: 102 which corresponds to sequence SEQ ID NO: 46 in which $X_{18}$ to $X_{40}$ are as defined for sequence SEQ ID NO: 66 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 67 which corresponds to sequence SEQ ID NO: 45 in which $X_{18}$ is V, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 103 which corresponds to sequence SEQ ID NO: 46 in which $X_{18}$ to $X_{40}$ are as defined for sequence SEQ ID NO: 67 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 68 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is K, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 104 which corresponds to sequence SEQ ID NO: 46 in which $X_{18}$ is to $X_{40}$ are as defined for sequence SEQ ID NO: 68 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 69 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is K, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is Y, and at most sequence SEQ ID NO: 106 which corresponds to sequence SEQ ID NO: 46 in which $X_{18}$ to $X_{40}$ are as defined for sequence SEQ ID NO: 69 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 70 which corresponds to sequence SEQ ED NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is T, $X_{34}$ is A, $X_{35}$ is T, $X_{36}$ is C, $X_{37}$ is V, $X_{38}$ is V, $X_{39}$ is C and $X_{40}$ is F, and at most sequence SEQ ID NO: 108 which corresponds to sequence SEQ ID NO: 46 in which $X_{18}$ to $X_{40}$ are as defined for sequence SEQ ID NO: 70 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 71 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{25}$ is V, $X_{29}$ is E, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 111 which corresponds to sequence SEQ ID NO: 46 in which $X_{18}$ to $X_{40}$ are as defined for sequence SEQ ID NO: 71 and $X_{41}$ is P, $X_{42}$ is A, $X_{43}$ is S, $X_{44}$ is Q, $X_{45}$ is S, $X_{46}$ is K and $X_{47}$ is I, the peptides having at least sequence SEQ ID NO: 72 which corresponds to sequence SEQ ID NO: 45 in which $X_{18}$ is L, $X_{19}$ is F, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is A, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 112 which corresponds to sequence SEQ ID NO: 46 in which $X_{18}$ to $X_{40}$ are as defined for sequence SEQ ID NO: 72 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 73 which corresponds to sequence SEQ ID NO: 45 in which $X_{18}$ is L, $X_{19}$ is F, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 113 which corresponds to sequence SEQ ID NO: 46 in which $X_{18}$ to $X_{40}$ are as defined for sequence SEQ ID NO: 73 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ED NO: 74 which corresponds to sequence SEQ ID NO: 45 in which $X_{18}$ is L, $X_{19}$ is F, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is A, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is A, $X_{39}$ is C and $X_{40}$ is Y, and at most sequence SEQ ID NO: 114 which corresponds to sequence SEQ ID NO: 46 in which $X_{18}$ to $X_{40}$ are as defined for sequence SEQ ID NO: 74 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 75 which corresponds to sequence SEQ ID NO: 45 in which $X_{18}$ is L, $X_{19}$ is L, $X_{20}$ is G, $X_{21}$ is C, $X_{22}$ is I, $X_{23}$ is V, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is F, and at most a sequence chosen from the following sequences:

i) sequence SEQ ID NO: 118 which corresponds to sequence SEQ ID NO: 46 in which $X_{18}$ to $X_{40}$ are as defined for sequence SEQ ID NO: 75 and $X_{41}$ is S, $X_{42}$ is A, $X_{43}$ is S, $X_{44}$ is Q, $X_{45}$ is S, $X_{46}$ is K and $X_{47}$ is T, and ii) sequence SEQ ID NO: 119 which corresponds to sequence SEQ ID NO: 46 in which $X_{18}$ to $X_{40}$ are as defined for sequence SEQ ID NO: 75 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 76 which corresponds to sequence SEQ ID NO: 45 in which $X_{18}$ is L, $X_{19}$ is F, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 121 which corresponds to sequence SEQ ID NO: 46 in which $X_{18}$ to $X_{40}$ are as defined for sequence SEQ ID NO: 76 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 77 which corresponds to sequence SEQ ED NO: 45 in which $X_{18}$ is L, $X_{19}$ is F, $X_{20}$ is G, $X_{21}$ is C, $X_{22}$ is I, $X_{23}$ is I, $X_{24}$ is K, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is I, $X_{38}$ is V, $X_{39}$ is C and $X_{40}$ is Y, and at most sequence SEQ ID NO: 122 which corresponds to sequence SEQ ID NO: 46 in which $X_{18}$ to $X_{40}$ are as defined for sequence SEQ ID NO: 77 and $X_{41}$ is P, $X_{42}$ is A, $X_{43}$ is A, $X_{44}$ is Q, $X_{45}$ is S, $X_{46}$ is K and $X_{47}$ is T, the peptides having at least sequence SEQ ID NO: 78 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is V, $X_{30}$ is V, $X_{31}$ is T, $X_{32}$ is Q, $X_{33}$ is S, $X_{34}$ is A, $X_{35}$ is T, $X_{36}$ is C, $X_{37}$ is L $X_{38}$ is V, $X_{39}$ is C and $X_{40}$ is F, and at most sequence SEQ ED NO: 123 which corresponds to sequence SEQ ID NO: 46 in which $X_{18}$ to $X_{40}$ are as defined for sequence SEQ ID NO: 78 and $X_{41}$ is P, $X_{42}$ is A, $X_{43}$ is S, $X_{44}$ is Q, $X_{45}$ is S, $X_{46}$ is K and $X_{47}$ is T, the peptides having at least sequence SEQ ID NO: 79 which corresponds to sequence SEQ ID NO: 45 in which $X_{18}$ is L, $X_{19}$ is L, $X_{20}$ is G, $X_{21}$ is C, $X_{22}$ is I, $X_{23}$ is I, $X_{24}$ is R, $X_{25}$ is Q, $X_{26}$ is V, $X_{27}$ is E, $X_{28}$ is V, $X_{29}$ is M, $X_{30}$ is V, $X_{31}$ is T, $X_{32}$ is Q, $X_{33}$ is S, $X_{34}$ is A, $X_{35}$ is T, $X_{36}$ is C, $X_{37}$ is V, $X_{38}$ is V, $X_{39}$ is C and $X_{40}$ is Y, and at most sequence SEQ ID NO: 125 which corresponds to sequence SEQ ID NO: 46 in which $X_{18}$ to $X_{40}$ are as defined for sequence SEQ ID NO: 79 and $X_{41}$ is H, $X_{42}$ is A, $X_{43}$ is S, $X_{44}$ is Q, $X_{45}$ is S, $X_{46}$ is K and $X_{47}$ is T, and the peptides having at least sequence SEQ ID NO: 80 which corresponds to sequence SEQ ID NO: 45 in which $X_{18}$ is L, $X_{19}$ is F, $X_{20}$ is S, $X_{21}$ is T, $X_{22}$ is I, $X_{23}$ is L $X_{24}$ is T, $X_{25}$ is E, $X_{26}$ is N, $X_{27}$ is C, $X_{28}$ is V, $X_{29}$ is V, $X_{30}$ is L, $X_{31}$ is T, $X_{32}$ is Q, $X_{33}$ is S, $X_{34}$ is G, $X_{35}$ is T, $X_{36}$ is A, $X_{37}$ is V, $X_{38}$ is V, $X_{39}$ is M and $X_{40}$ is Y, and at most sequence SEQ ID NO: 126 which corresponds to sequence SEQ ID NO: 46 in which $X_{18}$ to $X_{40}$ are as defined for sequence SEQ ID NO: 80 and $X_{41}$ is P, $X_{42}$ is A, $X_{43}$ is S, $X_{44}$ is Q, $X_{45}$ is A, $X_{46}$ is K and $X_{47}$ is T.

Preferably, the B peptide is chosen from the peptides of sequences SEQ ID NO: 47 to 80, the peptide of sequence SEQ ID NO: 47 being particularly preferred.

The C peptide in the compositions of the invention has at least the amino acid sequence SEQ ID NO: 127 as described previously.

According to one embodiment, the C peptide has at most the 57 amino acids as described in the following sequence SEQ ID NO: 128:

$$NFIX_{60}GX_{61}QYLAX_{62}LSTLPGNX_{63}AX_{64}X_{65}SX_{47}MX_{48}FTX_{49}X_{50}X_{51}TSPLX_{52}X_{53}X_{54}$$

$$X_{55}TLX_{56}FNIX_{57}GGWVAX_{58}QX_{59}X_{66}X_{67}X_{68}$$

in which $X_{47}$ to $X_{59}$ are as defined above and $X_{60}$ is T or S, $X_{61}$ is I, T or V, $X_{62}$ is G or A, $X_{63}$ is P or L, $X_{64}$ is I or M, $X_{65}$ is A, V or R, $X_{66}$ is A or R, $X_{67}$ is P, A or D and $X_{68}$ is P, A or S.

In this case, the C peptide is situated between positions 1767 and 1823 of the viral polyprotein.

According to another embodiment, the C peptide is chosen from the following peptides:

the peptides having at least sequence SEQ ID NO: 129 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is N, $X_{56}$ is L, $X_{57}$ is L, $X_{58}$ is A and $X_{59}$ is L and at most a sequence chosen from the following sequences:

i) sequence SEQ ID NO: 147 which corresponds to sequence SEQ ID NO: 128 in which $X_{47}$ to $X_{59}$ are as defined for sequence SEQ ID NO: 129 and $X_{60}$ is T, $X_{61}$ is I, $X_{62}$ is G, $X_{63}$ is P, $X_{64}$ is I, $X_{65}$ is A, $X_{66}$ is A, $X_{67}$ is P and $X_{68}$ is P, ii) sequence SEQ ID NO: 153 which corresponds to sequence SEQ ID NO: 128 in which $X_{47}$ to $X_{59}$ are as defined for sequence SEQ ID NO: 129 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, iii) sequence SEQ ID NO: 162 which corresponds to sequence SEQ ID NO: 128 in which $X_{47}$ to $X_{59}$ are as defined for sequence SEQ BD NO: 129 and $X_{60}$ is S, $X_{61}$ is I, $X_{62}$ is A, $X_{63}$ is P, $X_{64}$ is I, $X_{65}$ is A, $X_{66}$ is A, $X_{67}$ is P and $X_{68}$ is A, and iv) sequence SEQ ID NO: 167 which corresponds to sequence SEQ ID NO: 128 in which $X_{47}$ to $X_{59}$ are as defined for sequence SEQ ID NO: 129 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 130 which corresponds to sequence SEQ ID NO: 127 in which $X_{47}$ is L, $X_{48}$ is A, $X_{49}$ is A, $X_{50}$ is A, $X_{51}$ is V, $X_{52}$ is T, $X_{53}$ is T, $X_{54}$ is S, $X_{55}$ is Q, $X_{56}$ is L, $X_{57}$ is L, $X_{58}$ is A and $X_{59}$ is L and at most a sequence chosen from the following sequences:

i) sequence SEQ ID NO: 148 which corresponds to sequence SEQ ID NO: 128 in which $X_{47}$ to $X_{59}$ are as defined for sequence SEQ ID NO: 130 and $X_{60}$ is S, $X_{61}$ is I, $X_{62}$ is G, $X_{63}$ is P, $X_{64}$ is I, $X_{65}$ is A, $X_{66}$ is A, $X_{67}$ is A and $X_{68}$ is P, and ii) sequence SEQ ID NO: 150 which corresponds to sequence SEQ ID NO: 128 in which $X_{47}$ to $X_{59}$ are as defined for sequence SEQ ID NO: 130 and $X_{60}$ is S, $X_{61}$ is T, $X_{62}$ is G, $X_{63}$ is P, $X_{64}$ is I, $X_{65}$ is A, $X_{66}$ is A, $X_{67}$ is A and $X_{68}$ is P, the peptides having at least sequence SEQ ID NO: 131 which corresponds to sequence SEQ ID NO: 127 in which $X_{47}$ is L, $X_{48}$ is A, $X_{49}$ is A, $X_{50}$ is A, $X_{51}$ is V, $X_{52}$ is T, $X_{53}$ is T, $X_{54}$ is G, $X_{55}$ is Q, $X_{56}$ is L, $X_{57}$ is L, $X_{58}$ is A and $X_{59}$ is L and at most sequence SEQ ID NO: 149 which corresponds to sequence SEQ ID NO: 128 in which $X_{47}$ to $X_{59}$ are as defined for sequence SEQ ID NO: 131 and $X_{60}$ is S, $X_{61}$ is I, $X_{62}$ is G, $X_{63}$ is P, $X_{64}$ is I, $X_{65}$ is A, $X_{66}$ is A, $X_{67}$ is A and $X_{68}$ is P the peptides having at least sequence SEQ ID NO: 132 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is H, $X_{56}$ is L, $X_{57}$ is L, $X_{58}$ is A and $X_{59}$ is L and at most a sequence chosen from the following sequences:

i) sequence SEQ ID NO: 151 which corresponds to sequence SEQ ID NO: 128 in which $X_{47}$ to $X_{59}$ are as defined for sequence SEQ ID NO: 132 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, ii) sequence SEQ ID NO: 155 which corresponds to sequence SEQ ID NO: 128 in which $X_{47}$ to $X_{59}$ are as defined for sequence SEQ if D NO: 132 and $X_{60}$ is S, $X_{61}$ is I, $X_{62}$ is G, $X_{63}$ is P, $X_{64}$ is I, $X_{65}$ is V, $X_{66}$ is A, $X_{67}$ is P and $X_{68}$ is P, iii) sequence SEQ ID NO: 168 which corresponds to sequence SEQ ID NO: 128 in which $X_{47}$ to $X_{59}$ are as defined for sequence SEQ ID NO: 132 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, and iv) sequence SEQ ID NO: 171 which corresponds to sequence SEQ ID NO: 128 in which $X_{47}$ to $X_{59}$ are as defined for sequence SEQ ID NO: 132 and $X_{60}$ is S, $X_{61}$ is I, $X_{62}$ is G, $X_{63}$ is L, $X_{64}$ is I, $X_{65}$ is A, $X_{66}$ is A, $X_{67}$ is P and $X_{68}$ is P, the peptides having at least sequence SEQ ID NO: 133 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is S, $X_{56}$ is L, $X_{57}$ is L, $X_{58}$ is A and $X_{59}$ is L and at most sequence SEQ ID NO: 152 which corresponds to sequence SEQ ID NO: 128 in which $X_{47}$ to $X_{59}$ are as defined for sequence SEQ ID NO: 133 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 134 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is Y, $X_{56}$ is L, $X_{57}$ is L, $X_{58}$ is A and $X_{59}$ is L and at most a sequence chosen from the following sequences:

i) sequence SEQ ID NO: 154 which corresponds to sequence SEQ ID NO: 128 in which $X_{47}$ to $X_{59}$ are as defined for sequence SEQ ID NO: 134 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, and ii) sequence SEQ ID NO: 169 which corresponds to sequence SEQ ID NO: 128 in which $X_{47}$ to $X_{59}$ are as defined for sequence SEQ ID NO: 134 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 135 which corresponds to sequence SEQ ID NO: 127 in which $X_{47}$ is L, $X_{48}$ is A, $X_{49}$ is A, $X_{50}$ is S, $X_{51}$ is V, $X_{52}$ is T, $X_{53}$ is T, $X_{54}$ is Q, $X_{55}$ is N, $X_{56}$ is L, $X_{57}$ is L, $X_{58}$ is A and $X_{59}$ is L and at most sequence SEQ ID NO: 156 which corresponds to sequence SEQ ID NO: 128 in which $X_{47}$ to $X_{59}$ are as defined for sequence SEQ ID NO: 135 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 136 which corresponds to sequence SEQ ID NO: 127 in which $X_{47}$ is L, $X_{48}$ is A, $X_{49}$ is A, $X_{50}$ is S, $X_{51}$ is V, $X_{52}$ is T, $X_{53}$ is T, $X_{54}$ is Q, $X_{55}$ is S, $X_{56}$ is L, $X_{57}$ is L, $X_{58}$ is A and $X_{59}$ is L and at most a sequence chosen from the following sequences:

i) sequence SEQ ID NO: 157 which corresponds to sequence SEQ ID NO: 128 in which $X_{47}$ to $X_{59}$ are as defined for sequence SEQ ID NO: 136 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, and ii) sequence SEQ ID NO: 170 which corresponds to sequence SEQ ID NO: 128 in which $X_{47}$ to $X_{59}$ are as defined for sequence SEQ ID NO: 136 and $X_{60}$ is S, $X_{61}$ is V, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 137 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is T, $X_{56}$ is M, $X_{57}$ is L, $X_{58}$ is A and $X_{59}$ is L and at most sequence SEQ ID NO: 158 which corresponds to sequence SEQ ID NO: 128 in which $X_{47}$ to $X_{59}$ are as defined for sequence SEQ ID NO: 137 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 138 which corresponds to sequence SEQ ID NO: 127 in which $X_{47}$ is L, $X_{48}$ is A, $X_{49}$ is A, $X_{50}$ is S, $X_{51}$ is V, $X_{52}$ is T, $X_{53}$ is T, $X_{54}$ is Q, $X_{55}$ is Y, $X_{56}$ is L, $X_{57}$ is L, $X_{58}$ is A and $X_{59}$ is I and at most sequence SEQ ID NO: 159 which corresponds to sequence SEQ ID NO: 128 in which $X_{47}$ to, $X_{59}$ are as defined for sequence SEQ ID NO: 138 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 139 which corresponds to sequence SEQ ID NO: 127 in which $X_{47}$ is P, $X_{48}$ is A, $X_{49}$ is A, $X_{50}$ is S, $X_{51}$ is I, $X_{52}$ is T, $X_{53}$ is T, $X_{54}$ is Q, $X_{55}$ is H, $X_{56}$ is L, $X_{57}$ is L, $X_{58}$ is A and $X_{59}$ is L and at most sequence SEQ ID NO: 160 which corresponds to sequence SEQ ID NO: 128 in which $X_{47}$ to $X_{59}$ are as defined for sequence SEQ ID NO: 139 and $X_{60}$ is S, $X_{61}$ is I, $X_{62}$ is G, $X_{63}$ is P, $X_{64}$ is I, $X_{65}$ is R, $X_{66}$ is A, $X_{67}$ is P and $X_{68}$ is P, the peptides having at least sequence SEQ ID NO: 140 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is I, $X_{54}$ is Q, $X_{55}$ is H, $X_{56}$ is L, $X_{57}$ is L, $X_{58}$ is A and $X_{59}$ is P and at most sequence SEQ ID NO: 161 which corresponds to sequence SEQ ID NO: 128 in which $X_{47}$ to $X_{59}$ are as defined for sequence SEQ ID NO: 140 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and X is P, the peptides having at least sequence SEQ ID NO: 141 which corresponds to sequence SEQ ID NO: 127 in which $X_{47}$ is L, $X_{48}$ is A, $X_{49}$ is S, $X_{50}$ is S, $X_{51}$ is I, $X_{52}$ is T, $X_{53}$ is T, $X_{54}$ is Q, $X_{55}$ is S, $X_{56}$ is L, $X_{57}$ is L, $X_{58}$ is A and $X_{59}$ is L and at most sequence SEQ ID NO: 163 which corresponds to sequence SEQ ID NO: 128 in which $X_{47}$ to $X_{59}$ are as defined for sequence SEQ ID NO: 141 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 142 which corresponds to sequence SEQ ID NO: 127 in which $X_{47}$ is L, $X_{48}$ is A, $X_{49}$ is A, $X_{50}$ is S, $X_{51}$ is I, $X_{52}$ is S, $X_{53}$ is T, $X_{54}$ is Q, $X_{55}$ is N, $X_{56}$ is L, $X_{57}$ is W, $X_{58}$ is A and $X_{59}$ is L and at most sequence SEQ ID NO: 164 which corresponds to sequence SEQ ID NO: 128 in which $X_{47}$ to $X_{59}$ are as defined for sequence SEQ ID NO: 142 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 143 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is N, $X_{56}$ is M, $X_{57}$ is L, $X_{58}$ is A and $X_{59}$ is L and at most sequence SEQ ID NO: 165 which corresponds to sequence SEQ ID NO: 128 in which $X_{47}$ to $X_{59}$ are as defined for sequence SEQ ID NO: 143 and $X_{60}$ is S, $X_{61}$ is I, $X_{62}$ is G, $X_{63}$ is P, $X_{64}$ is I, $X_{65}$ is A, $X_{66}$ is A, $X_{67}$ is P and $X_{68}$ is P, the peptides having at least sequence SEQ ID NO: 144 which corresponds to sequence SEQ ID NO: 127 in which $X_{47}$ is L, $X_{48}$ is A, $X_{49}$ is A, $X_{50}$ is S, $X_{51}$ is I, $X_{52}$ is T, $X_{53}$ is T, $X_{54}$ is Q, $X_{55}$ is H, $X_{56}$ is M, $X_{57}$ is L, $X_{58}$ is A and $X_{59}$ is L and at most sequence SEQ DD NO: 166 which corresponds to sequence SEQ ID NO: 128 in which $X_{47}$ to $X_{59}$ are as defined for sequence SEQ ID NO: 144 and $X_{60}$ is S, $X_{61}$ is I, $X_{62}$ is G, $X_{63}$ is P, $X_{64}$ is M, $X_{65}$ is A, $X_{66}$ is A, $X_{67}$ is P and $X_{68}$ is P, the peptides having at least sequence SEQ ID NO: 145 which corresponds to sequence SEQ ID NO: 127 in which $X_{47}$ is L, $X_{48}$ is A, $X_{49}$ is A, $X_{50}$ is S, $X_{51}$ is I, $X_{52}$ is A, $X_{53}$ is T, $X_{54}$ is Q, $X_{55}$ is Y, $X_{56}$ is L, $X_{57}$ is L, $X_{58}$ is A and $X_{59}$ is L and at most sequence SEQ ID NO: 172 which corresponds to sequence SEQ ID NO: 128 in which $X_{47}$ to $X_{59}$ are as defined for sequence SEQ ID NO: 145 and $X_{60}$ is S, $X_{61}$ is I, $X_{62}$ is G, $X_{63}$ is P, $X_{64}$ is L $X_{65}$ is A, $X_{66}$ is A, $X_{67}$ is P and $X_{68}$ is P, the peptides having at least sequence SEQ ID NO: 146 which corresponds to sequence SEQ ID NO: 127 in which $X_{47}$ is L, $X_{48}$ is S, $X_{49}$ is A, $X_{50}$ is A, $X_{51}$ is V, $X_{52}$ is T, $X_{53}$ is T, $X_{54}$ is Q, $X_{55}$ is Q, $X_{56}$ is L, $X_{57}$ is L, $X_{58}$ is S and $X_{59}$ is I and at most sequence SEQ ID NO: 173 which corresponds to sequence SEQ ID NO: 128 in which $X_{47}$ to $X_{59}$ are as defined for sequence SEQ ID NO: 146 and $X_{60}$ is S, $X_{61}$ is I, $X_{62}$ is G, $X_{63}$ is P, $X_{64}$ is I, $X_{65}$ is A, $X_{66}$ is R, $X_{67}$ is D and $X_{68}$ is S.

Preferably, the C peptide is chosen from the peptides of sequences SEQ ID NO: 129 to 146, the peptide of sequence SEQ ID NO: 129 being particularly preferred.

The D peptide in the compositions of the invention has at least the amino acid sequence SEQ ID NO: 174 as described above.

According to one embodiment of the invention, the D peptide has at most the 44 amino acids as described in the following sequence SEQ ID NO: 175:

$$KGGX_{69}KX_{70}ARX_{71}IVX_{72}PX_{73}LGX_{74}RVCEKX_{75}ALX_{76}X_{77}VX_{78}X_{79}X_{80}X_{81}X_{82}X_{83}X_{84}$$

$$VMGX_{85}X_{86}YX_{87}X_{88}Q$$

in which $X_{69}$ to $X_{81}$ are as defined above and $X_{82}$ is P or A, $X_{83}$ is Q, L, H, R, K or P, $X_{84}$ is A, T, V or P, $X_{85}$ is P, S or A, $X_{86}$ is S or A, $X_{87}$ is G or R and $X_{88}$ is F or C.

In this case, the D peptide is situated between positions 2570 and 2613 of the viral polyprotein.

According to a further embodiment, the D peptide is chosen from the following peptides:

the peptides having at least sequence SEQ ID NO: 176 which corresponds to sequence SEQ ID NO: 174 in which $X_{69}$ is P, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from:

i) sequence SEQ ID NO: 188 which corresponds to sequence SEQ ID NO: 175 in which $X_{69}$ to $X_{81}$ are as defined for sequence SEQ ED NO: 176 and $X_{82}$ is P, $X_{83}$ is Q, $X_{84}$ is A, $X_{85}$ is P, $X_{86}$ is S, $X_{87}$ is G and $X_{88}$ is F, ii) sequence SEQ ID NO: 192 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is S, $X_{86}$ is S, $X_{87}$ is G and $X_{88}$ is F, iii) sequence SEQ ID NO: 193 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is A, $X_{86}$ is S, $X_{87}$ is G and $X_{88}$ is F, iv) sequence SEQ ED NO: 194 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is V, $X_{85}$ is S, $X_{86}$ is S, $X_{87}$ is G and $X_{88}$ is F, v) sequence SEQ ID NO: 201 which corresponds to sequence SEQ ID NO: 175 in which $X_{69}$ to $X_{81}$ are as defined for sequence SEQ ID NO: 176 and $X_{82}$ is P, $X_{83}$ is R, $X_{84}$ is A, $X_{85}$ is S, $X_{86}$ is S, $X_{87}$ is G and $X_{88}$ is C, vi) sequence SEQ ID NO: 202 which corresponds to sequence SEQ ID NO: 175 in which $X_{69}$ to $X_{81}$ are as defined for sequence SEQ BD NO: 176 and $X_{82}$ is P, $X_{83}$ is Q, $X_{84}$ is P, $X_{85}$ is S, $X_{86}$ is S, $X_{87}$ is G and $X_{88}$ is F, vii) sequence SEQ ID NO: 203 which corresponds to sequence SEQ ID NO: 175 in which $X_{69}$ to $X_{81}$ are as defined for sequence SEQ ID NO: 176 and $X_{82}$ is P, $X_{83}$ is H, $X_{84}$ is A, $X_{85}$ is S, $X_{86}$ is S, $X_{87}$ is G and $X_{88}$ is F, viii) sequence SEQ ID NO: 204 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is S, $X_{86}$ is A, $X_{87}$ is G and $X_{88}$ is F, ix) sequence SEQ ID NO: 205 which corresponds to sequence SEQ ID NO: 175 in which $X_{69}$ to $X_{81}$ are as defined for sequence SEQ ID NO: 176 and $X_{82}$ is P, $X_{83}$ is Q, $X_{84}$ is A, $X_{85}$ is S, $X_{86}$ is S, $X_{87}$ is R and $X_{88}$ is F, and x) sequence SEQ ID NO: 210 which corresponds to sequence SEQ ID NO: 175 in which $X_{69}$ to $X_{81}$ are as defined for sequence SEQ ID NO: 176 and $X_{82}$ is P, $X_{83}$ is H, $X_{84}$ is T, $X_{85}$ is S, $X_{86}$ is S, $X_{87}$ is G and $X_{88}$ is F, the peptides having at least sequence SEQ ID NO: 177 which corresponds to sequence SEQ ID NO: 174 in which $X_{69}$ is R, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is K and $X_{81}$ is L, and at most a sequence chosen from the following sequences:

i) sequence SEQ ID NO: 189 which corresponds to sequence SEQ ID NO: 175 in which $X_{69}$ to $X_{81}$ are as defined for sequence SEQ ID NO: 177 and $X_{82}$ is P, $X_{83}$ is L, $X_{84}$ is A, $X_{85}$ is S, $X_{86}$ is S, $X_{87}$ is G and $X_{88}$ is F, and ii) sequence SEQ ID NO: 190 which corresponds to sequence SEQ ID NO: 175 in which $X_{69}$ to $X_{81}$ are as defined for sequence SEQ ID NO: 177 and $X_{82}$ is P, $X_{83}$ is P, $X_{84}$ is A, $X_{85}$ is S, $X_{86}$ is S, $X_{87}$ is G and $X_{88}$ is F, the peptides having at least sequence SEQ ID NO: 178 which corresponds to sequence SEQ ID NO: 174 in which $X_{69}$ is R, $X_{70}$ is P, $X_{71}$ is L, $X_{72}$ is F, $X_{73}$ is D, $X_{74}$est V, $X_{75}$ is M, $X_{76}$ is Y, $X_{77}$ is D, $X_{78}$ is V, $X_{79}$ is T, $X_{80}$ is K and $X_{81}$ is L, and at most sequence SEQ ID NO: 191 which corresponds to sequence SEQ ID NO: 175 in which $X_{69}$ to $X_{81}$ are as defined for sequence SEQ ID NO: 178 and $X_{82}$ is P, $X_{83}$ is L, $X_{84}$ is A, $X_{85}$ is S, $X_{86}$ is S, $X_{87}$ is G and $X_{88}$ is F, the peptides having at least sequence SEQ ID NO: 179 which corresponds to sequence SEQ ID NO: 174 in which $X_{69}$ is Q, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, X is T and $X_{80}$ is L, and at most sequence SEQ ID NO: 195 which corresponds to sequence SEQ ID NO: 175 in which $X_{69}$ to $X_{81}$ are as defined for sequence SEQ ID NO: 179 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ED NO: 180 which corresponds to sequence SEQ ID NO: 174 in which $X_{69}$ is R, $X_{70}$ is A, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from the following sequences:

i) sequence SEQ ID NO: 196 which corresponds to sequence SEQ ID NO: 175 in which $X_{69}$ to $X_{81}$ are as defined for sequence SEQ ID NO: 180 and $X_{82}$ is P, $X_{83}$ is Q, $X_{84}$ is A, $X_{85}$ is S, $X_{86}$ is S, $X_{87}$ is G and $X_{88}$ is F, and ii) sequence SEQ ID NO: 206 which corresponds to sequence SEQ ID NO: 175 in which $X_{69}$ to $X_{81}$ are as defined for sequence SEQ ID NO: 180 and $X_{82}$ is P, $X_{83}$ is Q, $X_{84}$ is A, $X_{85}$ is P, $X_{86}$ is S, $X_{87}$ is G and $X_{88}$ is F, the peptides having at least sequence SEQ ID NO: 181 which corresponds to sequence SEQ ID NO: 174 in which $X_{69}$ is R, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is I and $X_{81}$ is L, and at most sequence SEQ ID NO: 197 which corresponds to sequence SEQ ID NO: 175 in which $X_{69}$ to $X_{81}$ are as defined for sequence SEQ ID NO: 181 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 182 which corresponds to sequence SEQ ID NO: 174 in which $X_{69}$ is R, $X_{70}$ is P, $X_{71}$ is L, $X_{72}$ is F, $X_{73}$ is E, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from the following sequences:

i) sequence SEQ ID NO: 198 which corresponds to sequence SEQ BD NO: 175 in which $X_{69}$ to $X_{81}$ are as defined for sequence SEQ ID NO: 182 and $X_{82}$ is P, $X_{83}$ is Q, $X_{84}$ is A, $X_{85}$ is S, $X_{86}$ is S, $X_{87}$ is G and $X_{88}$ is F, and ii) sequence SEQ ID NO: 209 which corresponds to sequence SEQ ID NO: 175 in which $X_{69}$ to $X_{81}$ are as defined for sequence SEQ ID NO: 182 and $X_{82}$ is P, $X_{83}$ is Q, $X_{84}$ is A, $X_{85}$ is P, $X_{86}$ is S, $X_{87}$ is G and $X_{88}$ is F, the peptides having at least sequence SEQ ID NO: 183 which corresponds to sequence SEQ ID NO: 174 in which $X_{69}$ is P, $X_{70}$ is P, $X_{71}$ is F, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most a sequence chosen from the following sequences:

i) sequence SEQ ID NO: 199 which corresponds to sequence SEQ ID NO: 175 in which $X_{69}$ to $X_{81}$ are as defined for sequence SEQ ID NO: 183 and $X_{82}$ is P, $X_{83}$ is K, $X_{84}$ is A, $X_{85}$ is S, $X_{86}$ is S, $X_{87}$ is G and $X_{88}$ is F, and ii) sequence SEQ ID NO: 200 which corresponds to sequence SEQ ID NO: 175 in which $X_{69}$ to $X_{81}$ are as defined for sequence SEQ ID NO: 183 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 184 which corresponds to sequence SEQ ID NO: 174 in which $X_{69}$ is R, $X_{70}$ is A, $X_{71}$ is L, $X_{72}$ is F, $X_{73}$ is D, $X_{74}$ is V, $X_{75}$ is M, $X_{76}$ is Y, $X_{77}$ is N, $X_{78}$ is V, $X_{79}$ is S, $X_{80}$ is T and $X_{81}$ is L, and at most sequence SEQ ID NO: 207 which corresponds to sequence SEQ ID NO: 175 in which $X_{69}$ to $X_{81}$ are as defined for sequence SEQ ID NO: 184 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 185 which corresponds to sequence SEQ ID NO: 174 in which $X_{69}$ is P, $X_{70}$ is P, $X_{71}$ is L, $X_{72}$ is F, $X_{73}$ is D, $X_{74}$ is V, $X_{75}$ is M, $X_{76}$ is Y, $X_{77}$ is D, $X_{78}$ is V, $X_{79}$ is S, $X_{80}$ is N and $X_{81}$ is L, and at most sequence SEQ ID NO: 208 which corresponds to sequence SEQ ID NO: 175 in which $X_{69}$ to $X_{81}$ are as defined for sequence SEQ ID NO: 185 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 186 which corresponds to sequence SEQ ID NO: 174 in which $X_{69}$ is R, $X_{70}$ is P, $X_{71}$ is L, $X_{72}$ is Y, $X_{73}$ is D, $X_{74}$ is V, $X_{75}$ is M, $X_{76}$ is Y, $X_{77}$ is D, $X_{78}$ is V, $X_{79}$ is S, $X_{80}$ is T and $X_{81}$ is L, and at most sequence SEQ ID NO: 211 which corresponds to sequence SEQ ID NO: 175 in which $X_{69}$ to $X_{81}$ are as defined for sequence SEQ ID NO: 186 and $X_{82}$ is P, $X_{83}$ is Q, $X_{84}$ is A, $X_{85}$ is S, $X_{86}$ is S, $X_{87}$ is G and $X_{88}$ is F, the peptides having at least sequence SEQ ID NO: 187 which corresponds to sequence SEQ ID NO: 174 in which $X_{69}$ is R, $X_{70}$ is P, $X_{71}$ is L, $X_{72}$ is Y, $X_{73}$ is D, $X_{74}$ is S, $X_{75}$ is R, $X_{76}$ is H, $X_{77}$ is D, $X_{78}$ is I, $X_{79}$ is K, $X_{80}$ is K and $X_{81}$ is T, and at most sequence SEQ ID NO: 212 which corresponds to sequence SEQ ID NO: 175 in which $X_{69}$ to $X_{81}$ are as defined for sequence SEQ ID NO: 187 and $X_{82}$ is A, $X_{83}$ is L, $X_{84}$ is A, $X_{85}$ is A, $X_{86}$ is A, $X_{87}$ is G and $X_{88}$ is F.

Preferably, the D peptide is chosen from the peptides of sequences SEQ ID NO: 176 to 187, the peptide of sequence SEQ ID NO: 176 being preferred.

The A, B, C or D peptides as defined by the preceding sequences 1 to 212 are novel and also constitute a subject of the invention.

Thus, according to the invention:

the A peptide has at least the amino acid sequence SEQ ID NO: 1 and at most sequence SEQ ID NO: 2; in particular it is chosen from the peptides:

having at least sequence SEQ ID NO: 3 and at most sequence SEQ ID NO: 19, having at least sequence SEQ ID NO: 4 and at most a sequence chosen from sequences SEQ ID NO: 20, SEQ ID NO: 24, SEQ ID, N32 and SEQ ID NO: 34, having at least sequence SEQ ID NO: 5 and at most a sequence chosen from sequences SEQ ID NO: 21, SEQ ID NO: 28 and SEQ ID NO: 36, having at least sequence SEQ ID NO: 6 and at most a sequence chosen from sequences SEQ ED NO: 22, SEQ ID NO: 27 and SEQ ID NO: 41, having at least sequence SEQ ID NO: 7 and at most a sequence chosen from sequences SEQ ID NO: 23 and SEQ ED NO: 37, having at least sequence SEQ ID NO: 8 and at most sequence SEQ ID NO: 25, having at least sequence SEQ ED NO: 9 and at most sequence SEQ ID NO: 26, having at least sequence SEQ ID NO: 10 and at most sequence SEQ ID NO: 29, having at least sequence SEQ ID NO: 11 and at most sequence SEQ ID NO: 30, having at least sequence SEQ ID NO: 12 and at most sequence SEQ ID NO: 31, having at least sequence SEQ ID NO: 13 and at most sequence SEQ ID NO: 33, having at least sequence SEQ ID NO: 14 and at most a sequence chosen from sequences SEQ ID NO: 35 and SEQ ID NO: 39, having at least sequence SEQ ID NO: 15 and at most sequence SEQ ID NO: 38, having at least sequence SEQ ID NO: 16 and at most a sequence chosen from sequences SEQ ID NO: 40 and SEQ ID NO: 42, having at least sequence SEQ ID NO: 17 and at most sequence SEQ ID NO: 43, and having at least sequence SEQ ID NO: 18 and at most sequence SEQ ID NO: 44, the peptides of sequence SEQ ID NO: 3 to 18 being preferred and the peptide of sequence SEQ ID NO: 3 being particularly preferred, the B peptide has at least the amino acid sequence SEQ ID NO: 45 and at most sequence SEQ ID NO: 46; in particular, the B peptide is chosen from the peptides:

having at least sequence SEQ ID NO: 47 and at most sequence SEQ ID NO: 81, having at least sequence SEQ ID NO: 48 and at most sequence SEQ ID NO: 82, having at least sequence SEQ ID NO: 49 and at most sequence SEQ ID NO: 83, having at least sequence SEQ ID NO: 50 and at most a sequence chosen from sequences SEQ ID NO: 84, SEQ ID NO: 90, SEQ ID NO: 105, SEQ ID NO: 107 and SEQ ID NO: 116, having at least sequence SEQ ID NO: 51 and at most a sequence chosen from sequences SEQ ID NO: 85 and SEQ ID NO: 124, having at least sequence SEQ ID NO: 52 and at most a sequence chosen from sequences SEQ ID NO: 86 and SEQ ID NO: 120, having at least sequence SEQ ID NO: 53 and at most sequence SEQ ID NO: 87, having at least sequence SEQ ID NO: 54 and at most a sequence chosen from sequences SEQ ID NO: 88 and SEQ ID NO: 117, having at least sequence SEQ ID NO: 55 and at most sequence SEQ ID NO: 89, having at least sequence SEQ ID NO: 56 and at most a sequence chosen from sequences SEQ ID NO: 91 and SEQ ID NO: 92, having at least sequence SEQ ID NO: 57 and at most sequence SEQ ID NO: 93, having at least sequence SEQ ID NO: 58 and at most a sequence chosen from sequences SEQ ID NO: 94 and SEQ ID NO: 110, having at least sequence SEQ ID NO: 59 and at most sequence SEQ ID NO: 95, having at least sequence SEQ ID NO: 60 and at most a sequence chosen from sequences SEQ ID NO: 96 and SEQ ID NO: 115, having at least sequence SEQ ID NO: 61 and at most sequence SEQ ID NO: 97, having at least sequence SEQ ID NO: 62 and at most a sequence chosen from sequences SEQ ID NO: 98 and SEQ ID NO: 109, having at least sequence SEQ ID NO: 63 and at most sequence SEQ ID NO: 99, having at least sequence SEQ ID NO: 64 and at most sequence SEQ ID NO: 100, having at least sequence SEQ ID NO: 65 and at most sequence SEQ ED NO: 101, having at least sequence SEQ ID NO: 66 and at most sequence SEQ ID NO: 102, having at least sequence SEQ ID NO: 67 and at most sequence SEQ ED NO: 103, having at least sequence SEQ ID NO: 68 and at most sequence SEQ ID NO: 104, having at least sequence SEQ ID NO: 69 and at most sequence SEQ ED NO: 106, having at least sequence SEQ ID NO: 70 and at most sequence SEQ ID NO: 108, having at least sequence SEQ ED NO: 71 and at most sequence SEQ ID NO: 111, having at least sequence SEQ ID NO: 72 and at most sequence SEQ ED NO: 112, having at least sequence SEQ ID NO: 73 and at most sequence SEQ ID NO: 113, having at least sequence SEQ ID NO: 74 and at most sequence SEQ ID NO: 114, having at least sequence SEQ ID NO: 75 and at most a sequence chosen from sequences SEQ ID NO: 118 and SEQ ID NO: 119 having at least sequence SEQ ID NO: 76 and at most sequence SEQ ID NO: 121, having at least sequence SEQ ID NO: 77 and at most sequence SEQ ID NO: 122, having at least sequence SEQ ID NO: 78 and at most sequence SEQ ID NO: 123, having at least sequence SEQ ID NO: 79 and at most sequence SEQ ID NO: 125, and having at least sequence SEQ ID NO: 80 and at most sequence SEQ ID NO: 126, the peptides of sequences SEQ ID NO: 47 to 80 being preferred and the peptide of sequence SEQ ID NO: 47 being particularly preferred, the C peptide has at least the amino acid sequence SEQ ID NO: 127 and at most sequence SEQ ID NO: 128; in particular, the C peptide is chosen from the peptides:

having at least sequence SEQ ID NO: 129 and at most a sequence chosen from sequences SEQ BD NO: 147, SEQ ED NO: 153, SEQ ID NO: 162 and SEQ ED NO: 167, having at least sequence SEQ ID NO: 130 and at most a sequence chosen from sequences SEQ BD NO: 148 and SEQ ID NO: 150, having at least sequence SEQ ID NO: 131 and at most sequence SEQ ID NO: 149, having at least sequence SEQ ID NO: 132 and at most a sequence chosen from sequences SEQ ID NO: 151, SEQ ID NO: 155, SEQ ED NO: 168 and SEQ ID NO: 171, having at least sequence SEQ ID NO: 133 and at most sequence SEQ BD NO: 152, having at least sequence SEQ ID NO: 134 and at most a sequence chosen from sequences SEQ BD NO: 154 and SEQ ED NO: 169, having at least sequence SEQ ID NO: 135 and at most sequence SEQ ID NO: 156, having at least sequence SEQ ID NO: 136 and at most a sequence chosen from sequences SEQ ID NO: 157 and SEQ BD NO: 170, having at least sequence SEQ ID NO: 137 and at most sequence SEQ ED NO: 158, having at least sequence SEQ ID NO: 138 and at most sequence SEQ ID NO: 159, having at least sequence SEQ BD NO: 139 and at most sequence SEQ ID NO: 160, having at least sequence SEQ ID NO: 140 and at most sequence SEQ ID NO: 161, having at least sequence SEQ ID NO: 141 and at most sequence SEQ ID NO: 163, having at least sequence SEQ BD NO: 142 and at most sequence SEQ ED NO: 164, having at least sequence SEQ ID NO: 143 and at most sequence SEQ ED NO: 165, having at least sequence SEQ ID NO: 144 and at most sequence SEQ ID NO: 166, having at least sequence SEQ ID NO: 145 and at most sequence SEQ ID NO: 172, and having at least sequence SEQ ID NO: 146 and at most sequence SEQ ID NO: 173, the peptides of sequence SEQ ID NO: 129 to 146 being preferred and the peptide of sequence SEQ ID NO: 129 being particularly preferred, and the D peptide has at least the amino acid sequence SEQ ID NO: 174 and at most sequence SEQ ID NO: 175; in particular, the D peptide is chosen from the peptides:

having at least sequence SEQ ID NO: 176 and at most a sequence chosen from sequences SEQ ID NO: 188, SEQ ID NO: 192, SEQ ID NO: 193, SEQ ID NO: 194, SEQ ID NO: 201, SEQ ID NO: 202, SEQ ID NO: 203, SEQ ID NO: 204, SEQ ID NO: 205 and SEQ ID NO: 210, having at least sequence SEQ ID NO: 177 and at most a sequence chosen from sequences SEQ ED NO: 189 and SEQ ID NO: 190, having at least sequence SEQ ID NO: 178 and at most sequence SEQ ID NO: 191, having at least sequence SEQ ID NO: 179 and at most sequence SEQ ID NO: 195, having at least sequence SEQ ID NO: 180 and at most a sequence chosen from sequences SEQ ID NO: 196 and SEQ ID NO: 206, having at least sequence SEQ ID NO: 181 and at most sequence SEQ ID NO: 197, having at least sequence SEQ ID NO: 182 and at most a sequence chosen from sequences SEQ ID NO: 198 and SEQ ID NO: 209, having at least sequence SEQ ID NO: 183 and at most a sequence chosen from sequences SEQ ID NO: 199 and SEQ ID NO: 200, having at least sequence SEQ ID NO: 184 and at most sequence SEQ ID NO: 207, having at least sequence SEQ ID NO: 185 and at most sequence SEQ ID NO: 208, having at least sequence SEQ ID NO: 186 and at most sequence SEQ ID NO: 211, and having at least sequence SEQ ID NO: 187 and at most sequence SEQ ID NO: 212, the peptides of sequence SEQ ID NO: 176 to 187 being preferred and the peptide of sequence SEQ ID NO: 176 being particularly preferred.

The expression "the A peptide has at least the amino acid sequence SEQ ID NO: 1 and at most sequence SEQ ID NO: 2" signifies that the N-terminal end is delimited by the amino acid situated at one of positions 1 to 8 of SEQ ID NO: 2 and the C-terminal end is delimited by the amino acid situated at one of positions 38 to 46 of SEQ ID NO: 2.

Thus the A peptide has at least the 31 consecutive amino acids of sequence SEQ ID NO: 1 and at most the 46 consecutive amino acids of sequence SEQ ID NO: 2.

Sequence SEQ ID NO: 2 includes the 31 amino acids of sequence SEQ ID NO: 1.

Thus the A peptide of the invention always has at least the 31 amino acids of sequence SEQ ID NO: 1 and at most 15 additional amino acids distributed on both sides of these 31 amino acids within the limit of sequence SEQ ID NO: 2. For example, an A peptide of the invention can comprise 33 amino acids constituted by 31 amino acids of SEQ ID NO: 1 and either 2 N-terminal amino acids, or 2 C-terminal amino acids, or 1 N-terminal amino acid and a C-terminal amino acid.

The expression "the B peptide has at least the amino acid sequence SEQ ID NO: 45 and at most sequence SEQ ID NO: 46" signifies that the N-terminal end is delimited by the amino acid situated at one of positions 1 to 12 of SEQ ID NO: 46 and the C-terminal end is delimited by the amino acid situated at one of positions 56 to 63 of SEQ ID NO: 46.

Thus the B peptide has at least the 45 consecutive amino acids of sequence SEQ ID NO: 45 and at most the 63 consecutive amino acids of sequence SEQ ID NO: 46.

Sequence SEQ ID NO: 46 includes the 45 amino acids of sequence SEQ ID NO: 45.

Thus the B peptide of the invention always has at least the 45 amino acids of sequence SEQ ID NO: 45 and at most 18 additional amino acids distributed on both sides of these 45 amino acids within the limit of sequence SEQ ID NO: 46.

The expression "the C peptide has at least the amino acid sequence SEQ ID NO: 127 and at most sequence SEQ ID NO: 128" signifies that the N-terminal end is delimited by the amino acid situated at one of positions 1 to 23 of SEQ ID NO: 128 and the C-terminal end is delimited by the amino acid situated at one of positions 54 to 57 of SEQ ID NO: 128.

Thus the C peptide has at least the 32 consecutive amino acids of sequence SEQ ID NO: 127 and at most the 57 consecutive amino acids of sequence SEQ ID NO: 128.

Sequence SEQ ID NO: 128 includes the 32 amino acids of sequence SEQ ID NO: 127.

Thus the C peptide of the invention always has at least the 32 amino acids of sequence SEQ ID NO: 127 and at most 25 additional amino acids distributed on both sides of these 32 amino acids within the limit of sequence SEQ ID NO: 128.

The expression "the D peptide has at least the amino acid sequence SEQ ID NO: 174 and at most sequence SEQ ID NO: 175" signifies that the N-terminal end is delimited by the amino acid situated at one of positions 1 to 4 of SEQ ID NO: 175 and the C-terminal end is delimited by the amino acid situated at one of positions 32 to 44 of SEQ ID NO: 175.

Thus the D peptide has at least the 29 consecutive amino acids of sequence SEQ ID NO: 174 and at most the 44 consecutive amino acids of sequence SEQ ID NO: 175.

Sequence SEQ ID NO: 175 includes the 29 amino acids of sequence SEQ ID NO: 174.

Thus the D peptide of the invention always has at least the 29 amino acids of sequence SEQ ID NO: 174 and at most 15 additional amino acids distributed on both sides of these 29 amino acids within the limit of sequence SEQ ID NO: 175.

The B and C peptides contain novel epitopes having a strong immunogenic power.

Another subject of the invention relates to the B' epitope, contained in the B peptide and situated between positions 1038 and 1047 of the viral polyprotein, which possesses the following amino acid sequence SEQ ID NO: 213:

$$GX_{18}X_{19}X_{20}X_{21}X_{22}X_{23}TSL$$

in which $X_{18}$ is L or V, $X_{19}$ is L or F, $X_{20}$ is G or S, $X_{21}$ is C or T, $X_{22}$ is I or V and $X_{23}$ is I or V.

According to one embodiment of the invention, the B' epitope is chosen from the following epitopes:

- the epitope of sequence SEQ ID NO: 214 which corresponds to sequence SEQ ID NO: 213 in which $X_{18}$ is L, $X_{19}$ is L, $X_{20}$ is G, $X_{21}$ is C, $X_{22}$ is I and $X_{23}$ is I,
- the epitope of sequence SEQ ID NO: 215 which corresponds to sequence SEQ ID NO: 213 in which $X_{18}$ is L, $X_{19}$ is F, $X_{20}$ is G, $X_{21}$ is C, $X_{22}$ is I and $X_{23}$ is I,
- the epitope of sequence SEQ ID NO: 216 which corresponds to sequence SEQ ID NO: 213 in which $X_{18}$ is V, $X_{19}$ is L, $X_{20}$ is G, $X_{21}$ is C, $X_{22}$ is V and $X_{23}$ is I,
- the epitope of sequence SEQ ID NO: 217 which corresponds to sequence SEQ ID NO: 213 in which $X_{18}$ is L, $X_{19}$ is V, $X_{20}$ is G, $X_{21}$ is C, $X_{22}$ is I and $X_{23}$ is I,
- the epitope of sequence SEQ ID NO: 218 which corresponds to sequence SEQ ID NO: 213 in which $X_{18}$ is L, $X_{19}$ is L, $X_{20}$ is G, $X_{21}$ is C, $X_{22}$ is I and $X_{23}$ is V,
- the epitope of sequence SEQ ID NO: 219 which corresponds to sequence SEQ ID NO: 213 in which $X_{18}$ is L, $X_{19}$ is F, $X_{20}$ is G, $X_{21}$ is C, $X_{22}$ is I and $X_{23}$ is V, and
- the epitope of sequence SEQ ID NO: 220 which corresponds to sequence SEQ ID NO: 213 in which $X_{18}$ is L, $X_{19}$ is F, $X_{20}$ is S, $X_{21}$ is T, $X_{22}$ is I and $X_{23}$ is I.

Preferably, the B' epitope possesses at least one of the following characteristics:

it has sequence SEQ ID NO: 214 and it is restricted to HLA-A2.

Another subject of the invention relates to the C' epitope, contained in the C peptide and situated between positions 1789 and 1821 of the viral polyprotein, which possesses the following amino acid sequence SEQ ID NO: 221:

$$SPLX_{52}X_{53}X_{54}X_{55}TL$$

in which $X_{52}$ is T, S or A, $X_{53}$ is T or I, $X_{54}$ is Q, S or G and $X_{55}$ is N, Q, H, S, Y or T.

According to one embodiment of the invention, the C' epitope is chosen from the following epitopes:

- the epitope of sequence SEQ ID NO: 222 which corresponds to sequence SEQ ID NO: 221 in which $X_{52}$ is T, $X_{53}$ is T, $X_{54}$ is Q and $X_{55}$ is N.
- the epitope of sequence SEQ ID NO: 223 which corresponds to sequence SEQ ID NO: 221 in which $X_{52}$ is T, $X_{53}$ is T, $X_{54}$ is S and $X_{55}$ is Q,
- the epitope of sequence SEQ ID NO: 224 which corresponds to sequence SEQ ID NO: 221 in which $X_{52}$ is T, $X_{53}$ is T, $X_{54}$ is G and $X_{55}$ is Q,
- the epitope of sequence SEQ ID NO: 225 which corresponds to sequence SEQ ID NO: 221 in which $X_{52}$ is T, $X_{53}$ is T, $X_{54}$ is Q and $X_{55}$ is H,
- the epitope of sequence SEQ ID NO: 226 which corresponds to sequence SEQ ID NO: 221 in which $X_{52}$ is T, $X_{53}$ is T, $X_{54}$ is Q and $X_{55}$ is S,
- the epitope of sequence SEQ ID NO: 227 which corresponds to sequence SEQ ID NO: 221 in which $X_{52}$ is T, $X_{53}$ is T, $X_{54}$ is Q and $X_{55}$ is Y,
- the epitope of sequence SEQ ID NO: 228 which corresponds to sequence SEQ ID NO: 221 in which $X_{52}$ is T, $X_{53}$ is T, $X_{54}$ is Q and $X_{55}$ is T,
- the epitope of sequence SEQ ID NO: 229 which corresponds to sequence SEQ ID NO: 221 in which $X_{52}$ is T, $X_{53}$ is I, $X_{54}$ is Q and $X_{55}$ is H,
- the epitope of sequence SEQ ID NO: 230 which corresponds to sequence SEQ ID NO: 221 in which $X_{52}$ is S, $X_{53}$ is T, $X_{54}$ is Q and $X_{55}$ is N,
- the epitope of sequence SEQ ID NO: 231 which corresponds to sequence SEQ ID NO: 221 in which $X_{52}$ is A, $X_{53}$ is T, $X_{54}$ is Q and $X_{55}$ is Y, and
- the epitope of sequence SEQ ID NO: 232 which corresponds to sequence SEQ ID NO: 221 in which $X_{52}$ is T, $X_{53}$ is T, $X_{54}$ is Q and $X_{55}$ is Q.

Preferably, the C' epitope possesses at least one of the following characteristics:

it has sequence SEQ ID NO: 222 and it is restricted to HLA-B7.

The compositions of the invention, apart from the A to D peptides, can also contain the B' and C' epitopes, which constitutes another subject of the invention.

The present invention also relates to the nucleotide sequences coding for any one of the A to D peptides as defined by sequences SEQ ID NO: 1 to 212 and B' and C' epitopes as defined by sequences SEQ ID NO: 213 to 232.

The peptides of the invention can be obtained by the genetic engineering technique which comprises the stages of:

culture of a microorganism or of eukaryotic cells transformed using a nucleotide sequence according to the invention and recovery of the peptide produced by said microorganism or said eukaryotic cells.

This technique is well known to a person skilled in the art. For more details concerning this, reference can be made to the following work: Recombinant DNA Technology I, Editors Ales Prokop, Raskesh K Bajpai; Annals of the New York Academy of Sciences, Volume 646, 1991.

The peptides of the invention can also be prepared by the standard peptide syntheses well known to a person skilled in the art.

The nucleotide sequences according to the invention can be prepared by chemical synthesis and genetic engineering using the techniques well known to a person skilled in the art and described for example in Sambrook J. et al., Molecular Cloning: A Laboratory Manual, 1989.

The nucleotide sequences of the invention can be inserted into expression vectors in order to obtain the compositions or peptides of the invention.

Thus, another subject of the invention is the expression vectors comprising a nucleotide sequence of the invention, as well as the means necessary for its expression.

As expression vector, there can be mentioned for example the plasmids, the viral vectors of the vaccine virus type, adenovirus, baculovirus, poxvirus, bacterial vectors of salmonella type, BCG.

By means necessary for the expression of a peptide is meant any means which make it possible to obtain the peptide, such as in particular a promoter, a transcription terminator, a replication origin and preferably a selection marker.

The vectors of the invention can also comprise sequences necessary for the screening of the peptides towards particular cell compartments. An example of screening can be screening towards the endoplasmic reticulum obtained using orientation sequences of the type of the leader sequence originating from the protein E3 of the adenovirus (Ciernik I. F., et al., The Journal of Immunology, 1999, 162, 3915-3925).

The expression vectors of the invention can comprise either a single nucleotide sequence coding for any one of the peptides of the invention, or at least two nucleotide sequences, it being understood that each nucleotide sequence codes for a peptide of different type.

According to one embodiment of the invention, the expression vectors include two nucleotide sequences coding for the A and B, A and C, A and D, B and C, B and D, or D and C peptides.

Preferably, the expression vectors include two nucleotide sequences coding for the A and B, A and C, B and D, or C and D peptides, the vectors comprising two sequences coding for the A and B, C and D, and B and D peptides being particularly preferred.

According to another embodiment, the expression vectors include three nucleotide sequences coding for the A, B and C, A, B and D, A, C and D, or B, C and D peptides.

According to yet another method, the expression vectors include four nucleotide sequences coding for the A to D peptides. Preferably, the vectors include three nucleotide sequences coding for the A, B and C, A, C and D, and B, C and D peptides. In this case, the order of the nucleotide sequences is relatively unimportant, as in the preceding combinations, such that the following combinations, given relative to the peptides, are comprised within the scope of the invention: A/B/C/D, A/B/D/C, A/C/B/D, A/C/D/B, A/D/B/C, A/D/C/B, B/A/C/D, B/A/D/C, B/C/A/D, B/C/D/A, B/D/A/C, B/D/C/A, C/A/B/D, C/A/D/B, C/B/A/D, C/B/D/A, C/D/A/B, C/D/B/A, D/A/B/C, D/A/C/B, D/B/A/C, D/B/C/A, D/C/A/B and D/C/B/A.

The expression vectors of the invention can also comprise at least one nucleotide sequence coding for any one of the B' and C' epitopes as defined previously, which constitutes another embodiment of the invention.

Thus, the vectors of the invention can comprise for example:

a nucleotide sequence coding for one of the following epitopes: B' and C', two nucleotide sequences coding for the B' and C' epitopes or several repetitive sequences coding for the B' epitope, the C' epitope or both.

The vectors of the invention can also comprise from two to four nucleotide sequences chosen from the sequences coding for the A, B, C, D peptides and the B' and C' epitopes, it being understood that:

the nucleotide sequence coding for the B peptide and the nucleotide sequence coding for the B' epitope are not present at the same time, and the nucleotide sequence coding for the C peptide and the nucleotide sequence coding for the C' epitope are not present at the same time.

Thus, for example, the vectors of the invention can comprise the following combinations, given relative to said peptides and epitopes: A/B', A/C', A'/D, B/C', B'/C, B'/D, C'/D, A/B'/C, A/B'/C', A/B/C', A/B'/D, A/C'/D, B'/C/D, B/C'/D, B'/C'/D, A/B'/C/D, A/B/C'/D and A/B'/C'/D.

Of course, as previously, the order of the nucleotide sequences in the expression vectors is relatively unimportant.

When the expression vectors of the invention include several nucleotide sequences, said sequences can be linked to each other directly, or via spacing or binding agents which are typically made up of small neutral molecules such as amino acids or amino acid mimetics which typically have a neutral charge under physiological conditions.

As spacing agents, there can be mentioned the Ala, Gly residues or other neutral spacing agents of non-polar amino acids or neutral polar amino acids.

These amino acid spacers have at least one or two residues and usually from 3 to 6 residues.

A subject of the invention is also the microorganisms and eukaryotic cells transformed by an expression vector of the invention.

When a composition of the invention containing at least two A to D peptides of the invention is to be obtained, the microorganisms or eukaryotic cells are transformed by an expression vector containing at least two nucleotide sequences, or they are cotransformed by at least two expression vectors containing a single nucleotide sequence, each vector coding for a peptide of different type.

According to one embodiment of the invention, the microorganisms and eukaryotic cells are cotransformed with:

two vectors coding respectively for the A and B, A and C, A and D, B and C, B and D, or C and D peptides, three vectors coding respectively for the A, B and C, A, B and D, A, C and D, or B, C and D peptides, or four vectors coding respectively for the A, B, C and D peptides.

Similarly, when a composition of the invention is to be obtained containing at least two B' and C' epitopes, or at least one B' or C' epitope and at least one A to D peptide, the microorganisms or eukaryotic cells are transformed by a single vector coding for the desired combination of epitopes or epitopes/peptides or by several vectors each coding for each constituent of the desired combination.

As examples of microorganisms which are appropriate for the purposes of the invention, there can be mentioned yeasts, such as those of the following families: *Saccharomyces, Schizosaccharomyces, Kluveromyces, Pichia, Hanseluna, Yarowia, Schwaniomyces, Zygosaccharomyces, Saccharomyces cerevisiae, Saccharomyces carlsbergensis* and *Kluveromyces lactis* being preferred; and bacteria, such as *E. coli* and those of the following families: *Lactobacillus, Lactococcus, Salmonella, Streptococcus, Bacillus* and *Streptomyces.*

As examples of eukaryotic cells, there can be mentioned cells originating from animals such as mammals, reptiles, insects and equivalent. The preferred eukaryotic cells are cells originating from the Chinese hamster (CHO cells), monkey (COS and Vero cells), baby hamster kidney (BHK cells), pig kidney (PK 15 cells) and rabbit kidney (RK13 cells, human osteosarcoma cell lines (143 B cells), human HeLa cell lines and human hepatoma cell lines (Hep G2 cell type), as well as insect cell lines (for example of *Spodoptera frugiperda*).

The host cells can be supplied in cultures in suspension or in vials, in tissue cultures, organ cultures and equivalent. The host cells can also be from transgenic animals.

The invention also relates to antibodies directed against one of the abovementioned peptides of the invention or against one of the peptide compositions of the invention as defined previously, or also against one of the epitopes of the invention.

The antibodies according to the invention are either polyclonal or monoclonal antibodies.

The abovementioned polyclonal antibodies can be obtained by immunization of an animal with at least one viral antigen of interest, followed by the recovery of the sought antibodies in purified form, by taking a sample of the serum of said animal, and separation of said antibodies from the other constituents of the serum, in particular by affinity chromatography on a column on which an antigen specifically recognized by the antibodies, in particular a viral antigen of interest, is fixed.

The monoclonal antibodies can be obtained by the hybridoma technique, the general principle of which is recalled hereafter.

Firstly, an animal, generally a mouse, (or cells in culture within the framework of in vitro immunizations) is immunized with a viral antigen of interest, the B lymphocytes of which are then capable of producing antibodies against said antigen. These antibody-producing lymphocytes are then fused with "immortal" myelomatous cells (murine in the example) in order to produce hybridomas. From the heterogeneous mixture of the cells thus obtained, a selection is then made of cells capable of producing a particular antibody and multiplying indefinitely. Each hybridoma is multiplied in clone form, each leading to the production of a monoclonal antibody the recognition properties of which vis-à-vis the viral antigen of interest can be tested for example in ELISA, by immunotransfer in one or two dimensions, in immunofluorescence, or using a biocaptor. The monoclonal antibodies thus selected are subsequently purified in particular according to the affinity chromatography technique described above.

The compositions of the invention, containing at least two A to D peptides or at least one of the B' and C' epitopes as described previously, are particularly effective for the inhibition, prevention and treatment of the virus or infection of patients carrying the virus belonging more particularly to the genotypes 1a, 1b and 4, in such a manner that its use for the preparation of a medicament constitutes another subject of the invention.

The present invention also relates to a pharmaceutical composition, in particular a vaccine, containing as active substance at least two different peptides chosen from the A to D peptides as defined previously, or at least two nucleotide sequences as described previously, placed under the control of elements necessary for a constitutive and/or inducible expression of said peptides, or at least one of the antibodies as defined previously, or also at least one of the B and C' epitopes as defined previously, or at least one of their nucleotide sequences, in combination with a pharmaceutically appropriate vehicle.

By elements necessary for a constitutive expression of the peptides, is meant a ubiquitous or specific promoter of the eukaryotic cells.

As elements necessary for an inducible expression of the peptides, there can be mentioned the elements of regulation of the operon of *E. coli* for resistance to tetracycline (Gossen M. and al, Proc Natl Acad Sci USA, 89: 5547-5551 (1992).

Of course, a person skilled in the art will easily determine the pharmaceutically appropriate vehicle and the quantity of peptides to be used as a function of the constituents of the pharmaceutical composition.

The invention also relates to a diagnostic composition for the detection and/or quantification of the hepatitis C virus comprising at least two different peptides chosen from the A to D peptides as defined previously, or at least one B' or C' epitope as defined previously, or at least one antibody as defined previously.

There also, a person skilled in the art will easily determine the quantity of peptides to be used as a function of the diagnostic technique used.

The invention also relates to a process for detection and/or quantification of the hepatitis C virus in a biological sample taken from an individual capable of being infected by said virus, such as plasma, serum or tissue, characterized in that it comprises stages consisting of:

bringing said biological sample into contact with at least one of the antibodies of the invention under conditions allowing the formation of a complex between the virus and the antibody, detecting and/or quantifying the formation of said complex by any appropriate means.

The processes of detection and/or quantification of the virus are implemented using standard techniques well known to a person skilled in the art and there can be mentioned, by way of illustration, blots, so-called sandwich techniques, competition techniques and PCR detection techniques, in particular so-called "real-time" techniques.

The invention also relates to the use of the compositions of the invention for the in vitro diagnosis of the hepatitis C virus in a biological sample.

Finally, the invention relates to the use of the compositions of the invention for the preparation of a vaccine composition.

BRIEF DESCRIPTION OF DRAWINGS

The present invention will be better understood using the following examples given only by way of illustration and non-limitatively, as well as using the attached FIGS. 1 to 14, in which:

FIG. 2 represents the alignments of the A peptides (SEQ ID NO:19) of the invention, FIGS. 3A and 3B represent the alignment of the B peptides of the invention.

FIG. 4 represents the alignments of the C peptides (SEQ ID NO:167) of the invention, FIG. 5 represents the alignments of the D peptides (SEQ ID NO:210) of the invention, FIG. 6 relates to the A peptide and shows a graph giving the specific lysis percentage of splenocytes of HLA-A2 transgenic mice according to the CTL test conditions after immunization of the mice by the A peptide of the invention, FIGS. 7A and 7B relate to the B peptide and show on the one hand a graph giving the specific lysis percentage of splenocytes of HLA-A2 transgenic mice according to the conditions of the CTL test after immunization of the mice by the B peptide of the invention (FIG. 7A) and on the other hand another graph giving the number of gamma-interferon-producing cells revealed by the ELISPOT method originating from the same transgenic mice and brought into contact with the ATL epitope of the prior art contained in the A peptide (FIG. 7B), FIGS. 8A and 8B relate to the C peptide and show on the one hand a graph giving the specific lysis percentage of splenocytes of HLA-A2 transgenic mice according to the CTL test conditions after immunization of the mice by the C peptide of the invention (FIG. 8A) and on the other hand another graph giving the number of gamma-interferon-producing cells revealed by the ELISPOT method originating from the same transgenic mice and brought into contact with the C peptide (FIG. 8B), FIGS. 9A and 9B relate to the D peptide and show on the one hand a graph giving the specific lysis percentage of splenocytes of HLA-A2 transgenic mice according to the CTL test conditions after immunization of the mice by the D peptide of the invention (FIG. 9A) and on the other hand another graph giving the number of gamma-interferon-producing cells revealed by the ELISPOT method originating from the same transgenic mice and brought into contact with the epitope ALY of the prior art contained in the D peptide (FIG. 9C)

EXAMPLE 1

Absence of Correlation Between the Binding Score and the Immunogenic Power of a Peptide-Epitope 1a: Test on Human Cells The ability of blood cells from 3 patients infected by the hepatitis C virus of genotype 1 and having an HLA of type HLA-A2+ to produce gamma-interferon cytokines and interleukin-10, in response to two peptides predicted by software developed by bioMerieux (Centre d'Immunologie de Pierre Fabre) to bind to the HLA-A2 molecule was tested.

The assay of these cytokines reflects the ability of the peptides to induce immune responses to cell mediation, either of type 1 (gamma interferon), or of type 2 (interleukin-10)

In order to do this, the FLAT (FLATCVNGV (SEQ ID NO:232)) and LLG (LLGCIITSL (SEQ ID NO:233)) epitopes included in the B peptide of the invention, which have equivalent binding scores (694 for FLAT and 619 for LLG) were used.

Mononucleated blood cells from 3 infected patients (200,000 cells per well) were incubated in an ELISPOT plate (Human IL10 Elispot Set, San Diego, Calif., USA) on which biotinylated antibodies specific to gamma interferon (BD kit) or interleukin-10 (purified mouse anti-human γ-IFN monoclonal antibody, BD, No. 554548) had been previously fixed, in the presence of the FLAT and LLG peptides.

After 48 hours of incubation at 37° C., a period during which the cells specific to the peptides will locally produce cytokines which will bind to the specific antibodies, anti-gamma interferon or anti-interleukin-10 antibodies, alkaline phosphatase coupled to avidine and the alkaline phosphatase substrate (NBT/BCIP) were added.

The violet-blue spots, which represent each gamma-interferon or interleukin-10-producing cell were counted, using Zeiss's ELISPOT automated reader (KS Elispot) and only considered positive when the number of spots per well was greater than 20.

Figure 1B:
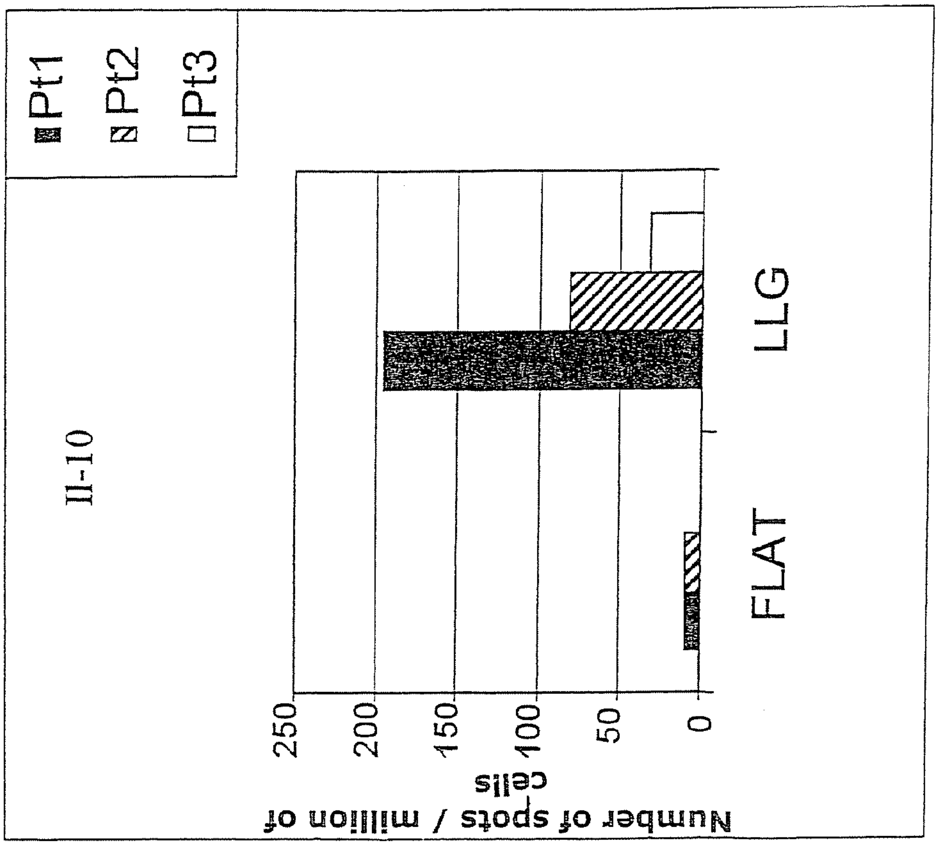
FIG. 1B represents the average production of interleukin-10 for 3 patients (Pt 1 to 3) infected by HCV strains of genotype 1 and having an HLA. A2+. This production is determined by the number of spots observed per million of blood cells brought into contact with the FLAT and LLG peptides.
Figure 1A:
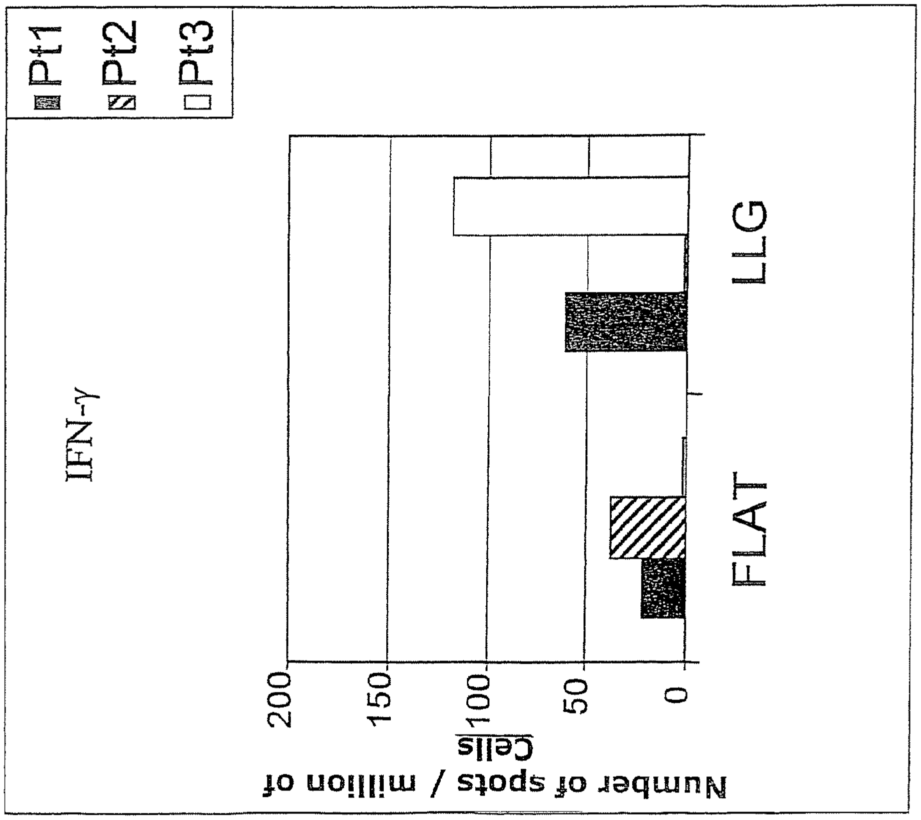
FIG. 1A represents the average production of gamma interferon for 3 patients (Pt 1 to 3) infected by HCV strains of genotype 1 and having an HLA. A2+. This production is determined by the number of spots observed per million of blood cells brought into contact with the FLAT (FLATCVNGV SEQ ID NO:232) and LLG (LLGCWTSL SEQ ID NO:233) peptides.

The results obtained are shown FIG. 1, in which Pt represents patient. They show that, despite an equivalent binding score on the HLA-A2 molecule, these two peptides do not induce equivalent responses.

In fact, the FLAT peptide induces little if any production of the two cytokines in the three patients, whereas the LLG peptide induces a significant production of gamma interferon in 2 of the 3 patients and of interleukin-10 in the three patients.

The results obtained also show that the peptides of the invention, as well as their combination was not evident with regard to the teachings of the prior art.

1b: Test on Murine Cells

Mice transgenic for the molecule HLA.A2.1 and devoid of murine class 1 molecules (Pascolo S., et al. (1997), J. Exp Med., 185, 2043-2051) were immunized with the FLL and ILA epitopes predicted as being class I epitopes restricted by the molecule HLA.A2.1. The FLL peptide has an average score (515) whereas the ILA peptide has a very high score (893).

In order to do this, the mice were immunized in the base of their tails with a peptide mixture containing one of the above epitopes (60 μM) and the T-helper peptide (Lone, Y. C. et al., (1998), J. Immunother. 21:283-294) (60 μM) emulsified in incomplete Freund's adjuvant (Sigma St Louis, Mo.). The mice received two injections with an interval of two weeks and the immune responses were analyzed two weeks after the last immunization as indicated in Example 1 (Elispot).

The results are shown in Table 1 below.

TABLE 1

| Epitope | Viral antigen | Score | Number of spots/$10^6$ cells[1*] |
|---|---|---|---|
| FLLLADARV (SEQ ID NO: 234) | E2 | 515 | 333; 215; 622 |
| ILAGYAGAGV (SEQ ID NO: 235) | NS4 | 893 | 5; 2; 0 |

[1]Gamma-interferon-producing cells

*Number of spots for three individual mice tested.

These results show that the score ascribed to a peptide does not reflect its immunogencity.

EXAMPLE 2

Demonstration of the Immunogenicity of the Peptides/Peptide Compositions/Epitopes of the Invention in Mice HLA-A2.1-transgenic mice were immunized either with the A peptide of sequence SEQ ID NO: 3, or with the B peptide of sequence SEQ ID NO: 47, or with the C peptide of sequence SEQ ID NO: 129, or with the D peptide of sequence SEQ ID NO: 176, or with the B' epitope of sequence SEQ ID NO: 214 or with the ATL and ALY epitopes of the prior art contained respectively in the A and D peptides (ATLGFGAYM (SEQ ID NO:237), amino acids 1260-1268 of the viral polyprotein and ALYDVVSTL (SEQ ID NO:238), amino acids 2594-2602 of the viral polyprotein).

In order to do this, 2 sub-cutaneous injections were administered into the base of the tail of each mouse, with an interval of 15 days, of a mixture containing 18 nmoles of peptide of the invention and 18 nmoles of the HBV core helper peptide in incomplete Freund's adjuvant (IFA, Brinster et al., Hepatology 2001) or containing 60 nmoles of epitope of the invention and 60 nmoles of the helper peptide in IFA.

The control mice received only the helper peptide in IFA.

Fifteen days after the 2nd injection, the cell response was analyzed by isolating the spleen cells (splenocytes) of mice and a CTL test and an ELISPOT test were carried out as follows:

For the CTL test, these splenocytes were cultured in 24-well plates in the presence of 5 μM of the peptide or epitope of interest and 10 U of recombinant murine interleukin-2 (Brinster et al., Hepatology 2001) per ml in alpha minimum essential medium (αMEM) for 5 days. On the 5th day, the restimulation stage was carried out, consisting of adding to the splenocytes in culture splenocytes of naïve mice in the presence of the peptide or epitope of interest over 2 days. On the 7th day, the CTL test itself was carried out, consisting of bringing together the splenocytes of the immunized mice after the 7 days of culture (effective cells) and EL4 S3-Rob HDD cells charged with 10 μM of the peptide or epitope of interest marked with $Cr^{51}$ (target cells). The specific cytotoxic activity of the effective cells was determined by measuring, after 4 hours of incubation with the target cells, the $Cr^{51}$ released following the lysis of the target cells using a γ-Cobra II (Packard, Rungis, France) counting device. The spontaneous and maximum release from wells containing either the medium alone, or the lysis buffer (HCl 1N) were determined. The specific percentage of cytotoxicity was calculated by the formula:

(release in the test−spontaneous release)/(maximum release−spontaneous release)×100. The peptide or epitope-specific lysis was determined by the difference between the percentage of specific lysis obtained in the presence or absence of the peptide or epitope.

The ELISPOT test was carried out by culturing the splenocytes for 48 hours in Multiscreen (Millipore) 96-well plates previously coated with anti-γ-interferon (γIFN) antibodies (10 μg/ml final). The splenocytes were cultured in the presence of 10 μM of peptide or epitope of interest and 10 U of recombinant murine interleukin-2 per ml in αMEM. For the positive control, the splenocytes were cultured in the presence of concanavalin A (5 μg/ml). For the negative control, the splenocytes were cultured either in the presence of a non-specific peptide belonging to the HCV capsid protein, of sequence DLMGYIPLV (SEQ ID NO:239) (also called irrelevant peptide), or in medium alone without peptide or epitope of interest. The wells were washed three times, respectively with PBS-Tween 0.05% then PBS, an operation followed by incubation for 2 hours with biotinylated anti-γ-IFN antibodies of mice. After washing, the wells were incubated for 1 hour with a streptavidin-horseradish peroxidase conjugate and the enzymatic activity was revealed by degradation of the AEC (aminoethylcarbazole) substrate. The spots obtained were counted using a Zeiss ELISpot reader (Zeiss microscope coupled with the KS-ELISpot software).

Figure 6:
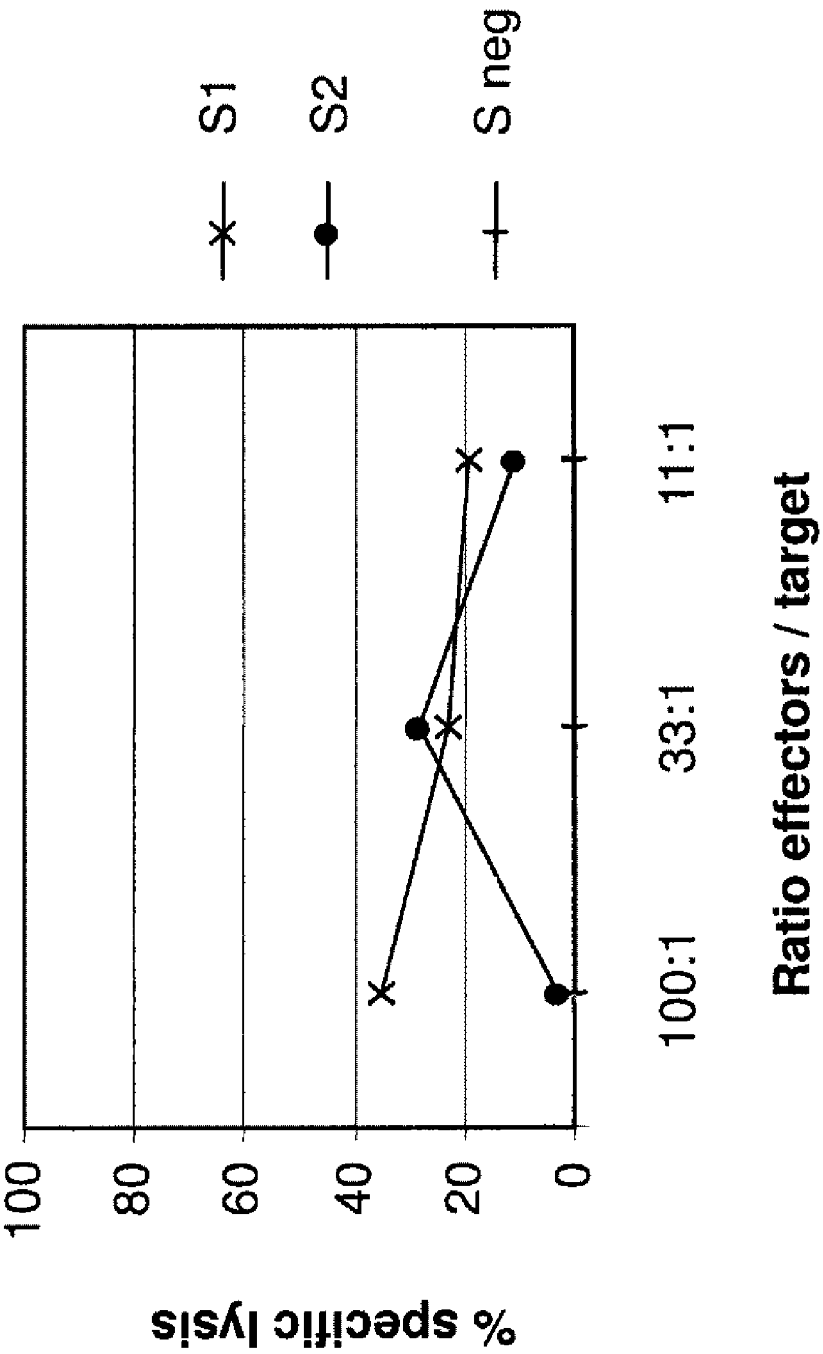
Figure 7A:
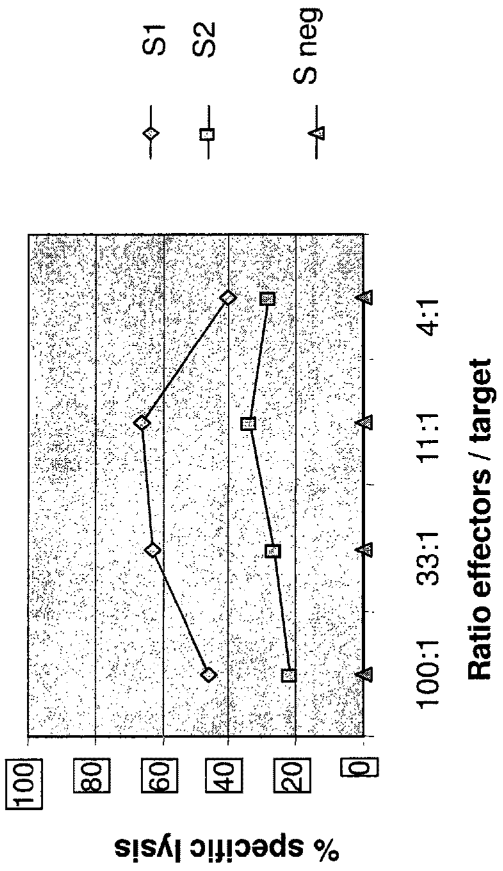
Figure 8A:
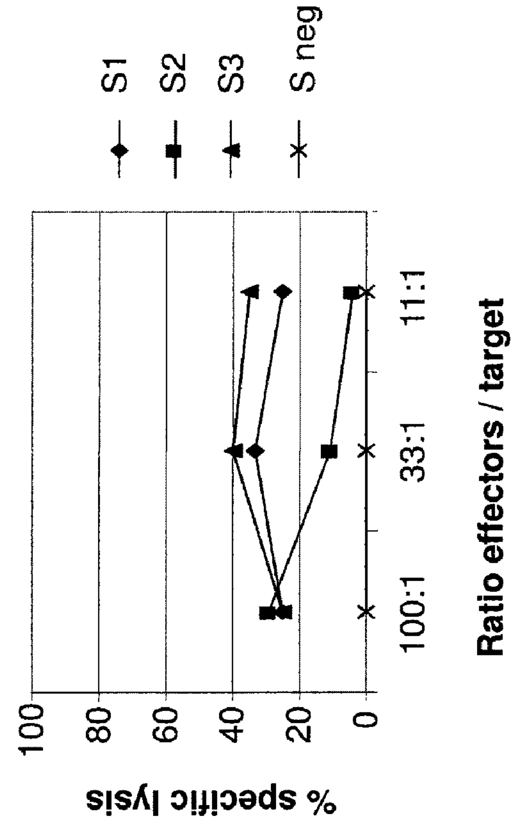
Figure 9A:
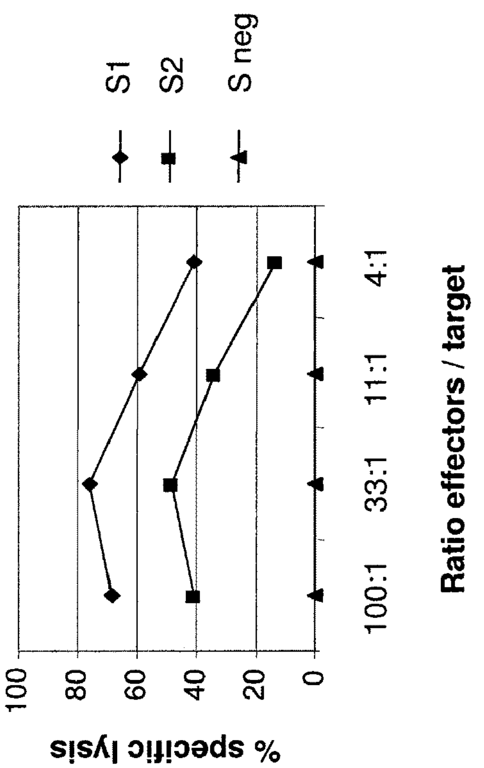
Figure 10:
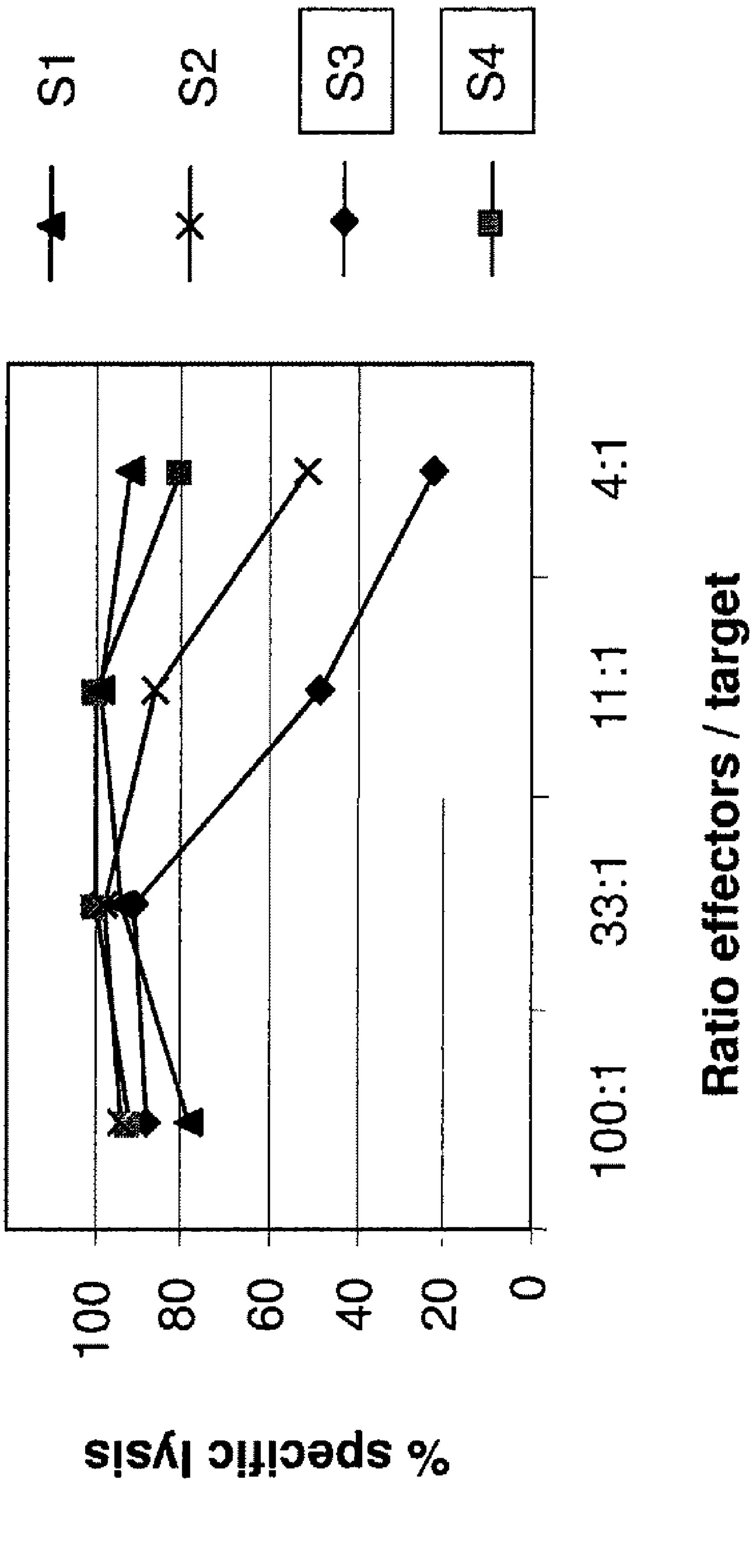
FIG. 10 is a graph giving the specific lysis percentage of splenocytes of HLA-A2 transgenic mice according to the CTL test conditions after immunization of the mice by the D peptide of the invention or after immunization with the ALY epitope.
Figure 11:
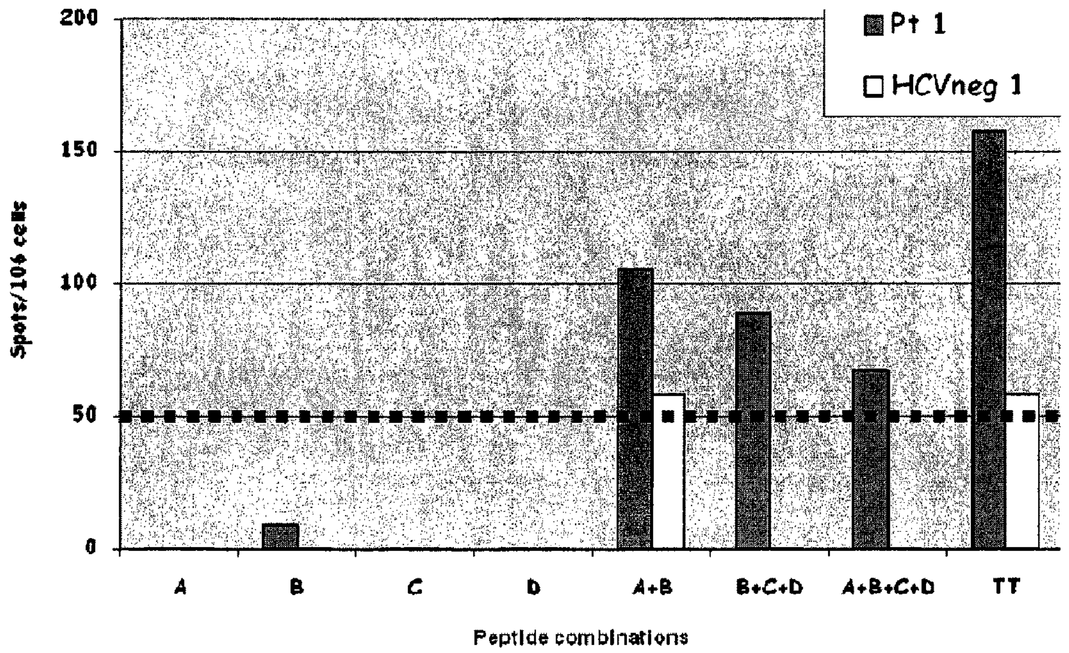
FIG. 11 is a graph representing the number of gamma-interferon-producing cells revealed by the ELISPOT method originating from an HCV-seropositive patient and brought into contact with the A, B, C and D peptides, as well as with the compositions A/B, B/C/D and A/B/C/D.
Figure 12:
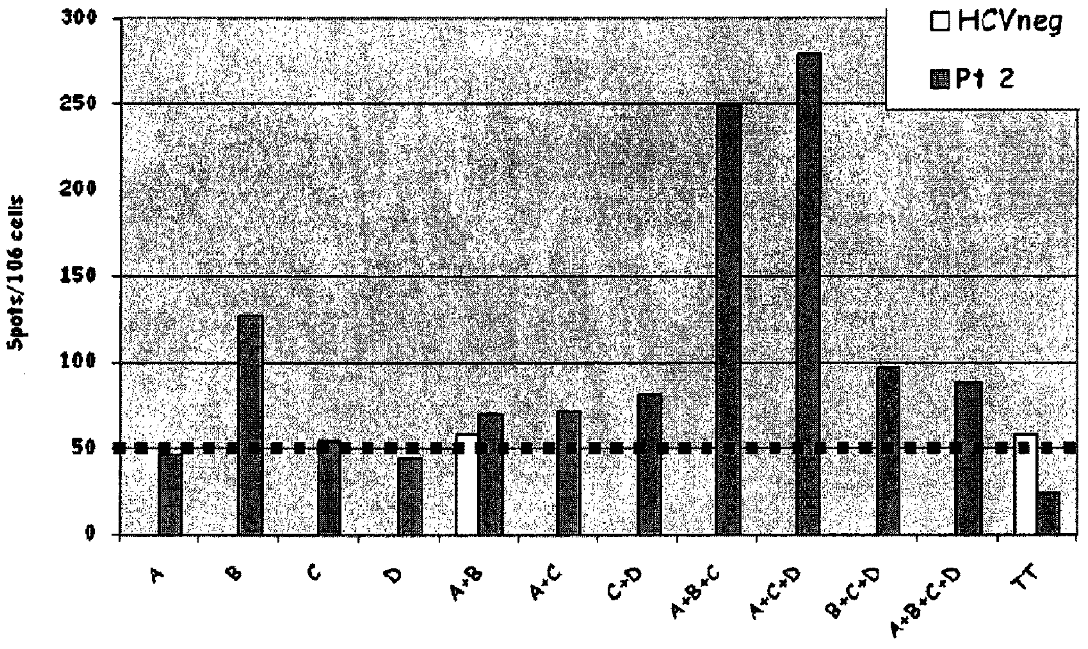
FIG. 12 is a graph representing the number of gamma-interferon-producing cells revealed by the ELISPOT method originating from another HCV-seropositive patient and brought into contact with the A, B, C and D peptides, as well as with the compositions A/B, A/C, C/D, A/B/C, A/C/D, B/C/D and A/B/C/D.
Figure 13:
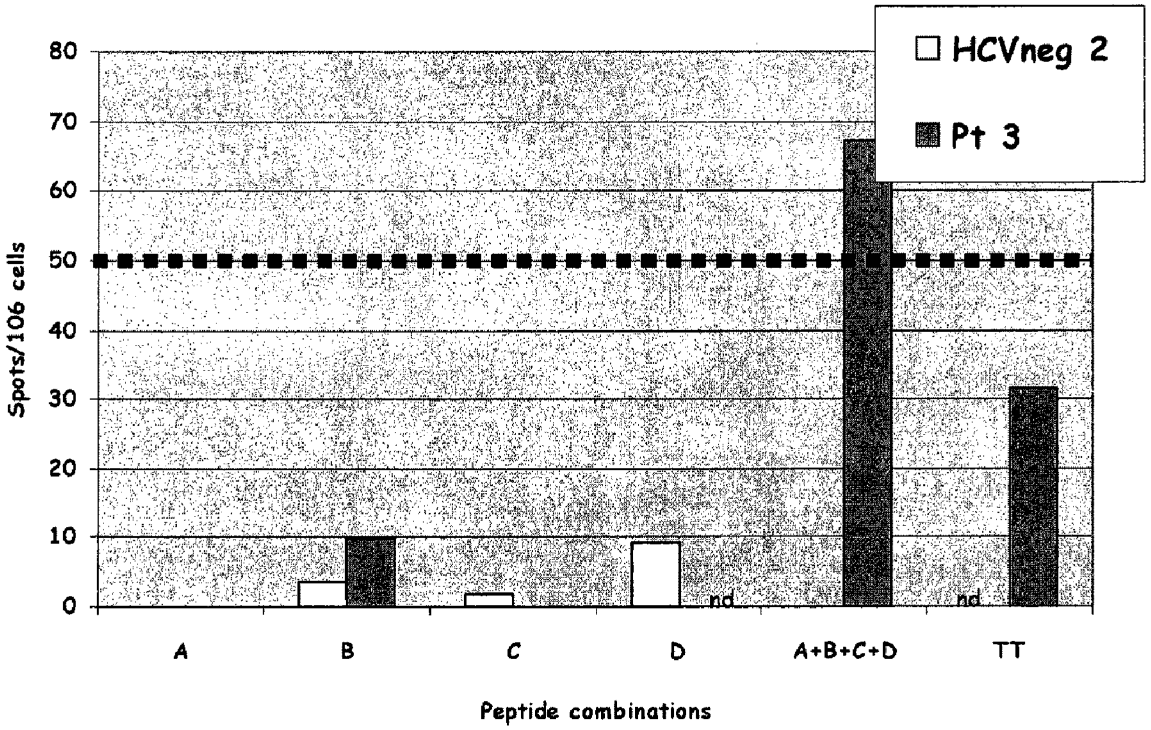
FIG. 13 is a graph representing the number of gamma-interferon-producing cells revealed by the ELISPOT method originating from another HCV-seropositive patient and brought into contact with the A, B, C and D peptides, as well as with the composition A/B/C/D.
Figure 14:
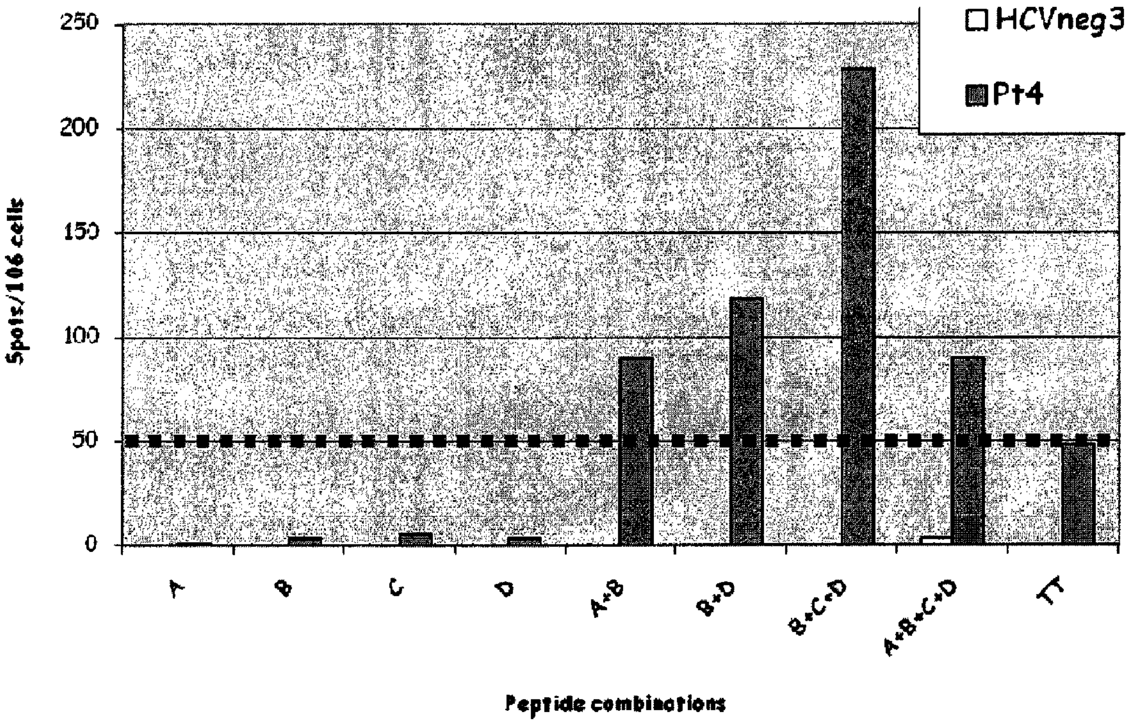
FIG. 14 is a graph representing the number of gamma-interferon-producing cells revealed by the ELISPOT method originating from another HCV-seropositive patient and brought into contact with the A, B, C and D peptides, as well as with the compositions A/B, B/D, B/C/D and A/B/C/D.

The results of the CTL tests are shown in FIGS. 6, 7A to 9A and 10 where S1 is mouse 1, S2 is mouse 2, S3 is mouse 3, S4 is mouse 4 and S neg is the control mouse and where:

FIG. 6 shows the specific lysis percentage, as a function of the effectors/target ratio, after injection of the A peptide taking the ATL epitope as target, FIG. 7A shows the specific lysis percentage, as a function of the effectors/target ratio, after injection of the B peptide taking the B' epitope as target, FIG. 8A shows the specific lysis percentage, as a function of the effectors/target ratio, after injection of the C peptide taking the C peptide as target, FIG. 9A shows the specific lysis percentage, as a function of the effectors/target ratio, after injection of the D peptide taking the ALY epitope as target, and FIG. 10 shows the specific lysis percentage, as a function of the effectors/target ratio, after injection of the D peptide taking the ALY epitope (mice S1 and S3) as target or the ALY epitope taking the ALY epitope (mice S3 and S4) as target.

The results as shown in FIGS. 6 to 9 show that the injection of each peptide induces a cytotoxic response against the corresponding epitopes such that:

(i) both said peptides and said epitopes have an immunogenic power, and (ii) the peptides of the invention are capable of inducing immune responses specific to epitopes present in the natural infection.

It is to be noted that FIG. 10 shows that the D peptide and the epitope have identical lysis effectiveness. It is therefore clear from this experience, with regard to the quantities of peptide and epitopes used (injection of 18 nmoles of the D peptide (mice S1 and S2) and injection of 60 nmoles of the ALY epitope (mice S3 and S4), taking the ALY epitope as target), that the peptides of the invention have the advantage that they are immunogenic at doses lower than the epitopes that they contain.

The CTL test was also repeated injecting the composition ABCD or the B peptide taking the B' epitope as target and injecting the composition ABCD or the C peptide taking the C peptide as target. The results are indicated in Table 3 below.

TABLE 3

| | | | Effectors/targets ratio | |
|---|---|---|---|---|
| | | | 100:1 | 33:1 |
| Injection ABCD | Target B' | S1 | 55 | 52 |
| | | S2 | 32 | 55 |
| | | S3 | 53 | 65 |
| Injection B | | S1 | 46 | 63 |
| | | S2 | 22 | 27 |
| Injection ABCD | Target C | S1 | 52 | 69 |
| | | S2 | 1 | 67 |
| Injection C | | S1 | 2 | 9 |
| | | S2 | 0 | 0 |

The results in the above table demonstrate that injection of the combination of the 4 A, B, C and D peptides induces a cytotoxic response more effective than injection of the peptides alone.

Figure 7B:
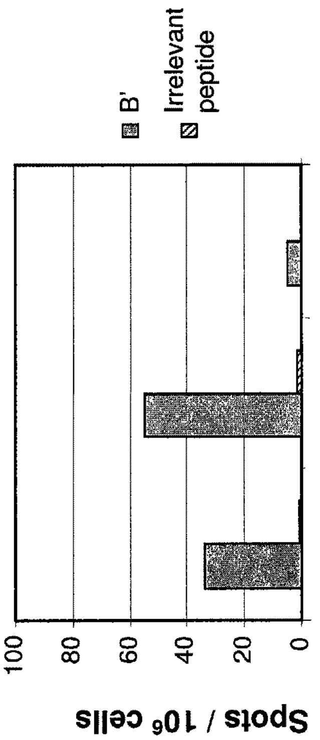

The results of the ELISPOT tests are shown in FIGS. 7B to 9B where S1, S2 S3 and S neg have the same definitions as previously and where:

FIG. 7B shows the number of spots relative to $10^6$ cells for mice having received the B peptide relative to the B' epitope target, as well as the number of spots for the irrelevant peptide.

Figure 8B:
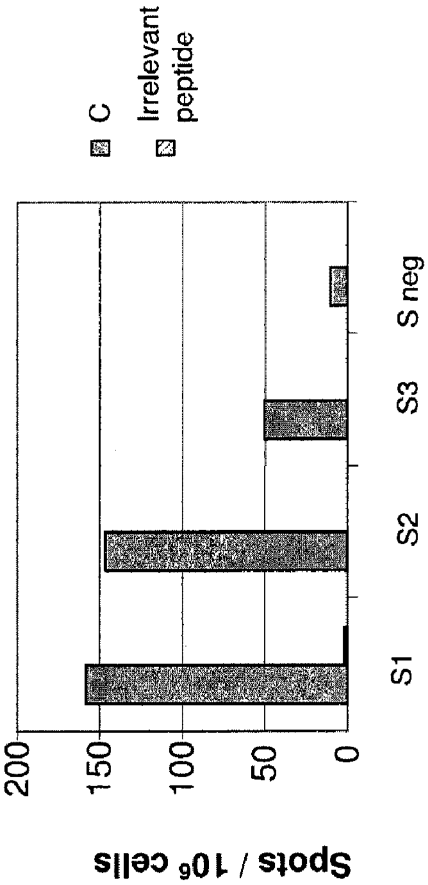

FIG. 8B shows the number of spots relative to $10^6$ cells for mice having received the C peptide relative to the C peptide target, as well as the number of spots for the irrelevant peptide.

Figure 9B:
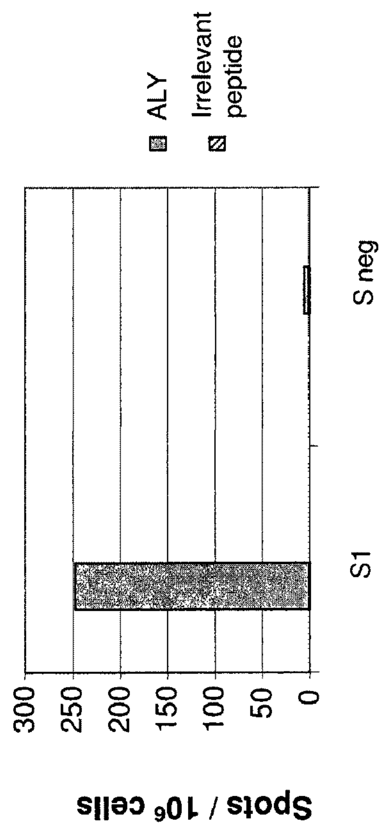

FIG. 9B shows the number of spots relative to $10^6$ cells for mice having received the D peptide relative to the ALY epitope target, as well as the number of spots for the irrelevant peptide.

The results shown in FIGS. 7B to 9B confirm the good immunogenic power of the peptides and epitopes of the invention.

EXAMPLE 3

Demonstration of the Immunogenicity of the Peptides/Peptide Compositions of the Invention in Humans Peripheral blood mononucleated cells from four patients chronically infected by the hepatitis C virus were purified by Ficoll gradient centrifugation. Two hundred thousand cells were pre-incubated at 37° C., 5% $CO_2$, overnight in polypropylene tubes in the presence of the A to D peptides, having the amino acid sequences as defined in Example 2 above, and their compositions, in culture medium comprising $RPMI_{1640}$ (Invitrogen Life technology, Cergy Pontoise, France) supplemented with 2 mM of L-Glutamine (Invitrogen Life Technology), 50 UI/ml of penicillin (Invitrogen Life Technology), 50 μg/ml of streptomycin (Invitrogen Life Technology) and 10% of fetal calf serum (Hyclone, Logan, Utah, USA) according to the following Table 4:

TABLE 4

| Patient | Genotype | Clinical status | Peptides/peptide compositions |
|---|---|---|---|
| 1 | 1b | Not treated | A, B, C, D, AB, BCD, ABCD |
| 2 | 1 | Not responsive to ribavirin M12 | A, B, C, D, AB, AC, CD, ABC, ACD, BCD, ABCD |
| 3 | 4f | Not treated | A, B, C, D, ABCD |
| 4 | 1 | Not responsive to γIFN + ribavirin M6 | A, B, C, D, AB, BD, BCD, ABCD |

The peptides, alone or in combination, were present in the following concentrations: A at 10 μM, B at 5 μM, C at 1 μM and D at μM.

The cells were then transferred to an ELISPOT plate made of PVDF (polyvinylidene fluoride) previously coated with anti-γIFN antibodies according to the manufacturer's (Diaclone, Besançon, France) recommendations and incubated for another 24 hours at 37° C., 5% $CO_2$. As previously, here cytokine-producing cells are sought, which will form blue spots which are revealed, after sequential incubation with a biotinylated anti-γIFN antibody and PAL coupled to streptavidin, by degradation of the BCIP/NBT (salt of 5-bromo-4-chloro-3-indolylphosphate p-toluidine/nitroblue tetrazolium chloride) substrate and which are counted using the Zeiss ELISPOT reader.

As positive control, the peptides/peptide compositions were replaced by tetanic toxin (TT) at 1 μg/ml.

This procedure was repeated starting with cells from HCV-seronegative patients.

The results are shown in FIGS. 11 to 14 giving the number of spots per million cells as a function of the peptides and their combinations (average of the triplicates) obtained with patients 1 to 4 respectively, and in which the dotted line represents the significance threshold of the test (50 spots), Pt is patient and HCVneg is an HCV-seronegative patient.

The results demonstrate that the peptide compositions of the invention have a strong immunogenic power.

The invention claimed is:

1. A pharmaceutical composition containing as active ingredient at least two nucleotide sequences coding for separate peptides chosen from A to D peptides, placed under the control of elements necessary for expression of nucleic acid sequences, in combination with a pharmaceutically appropriate vehicle, wherein the A peptide has at least the following amino acid sequence SEQ ID NO: 1:

$X_1AX_2QGYKVX_3VLNPSVX_4ATLX_5FGX_6YMSKAX_7GX_8$, in which $X_1$ is Y or H, $X_2$ is A, G or T, $X_3$ is R or L, $X_4$ is A or T, $X_5$ is G or S, $X_6$ is A, T or V, $X_7$ is H or Y and $X_8$ is I, T, M or V, and has at most the 46 amino acids as defined in the following sequence SEQ ID NO:2:

$SX_9X_{10}VPX_{11}X_{12}X_1AX_2QGYKVX_3VLNPSVX_4ATLX_5FGX_6YMSKAX_7GX_8X_{13}PX_{14}$
$X_{15}X_{16}X_{17}GV$, in which $X_1$ to $X_8$ are as defined above, and $X_9$ is T or N, $X_{10}$ is K or R, $X_{11}$ is A or V, $X_{12}$ is A or E, $X_{13}$ is E or D, $X_{14}$ is N or S, $X_{15}$ is I, L or V, $X_{16}$ is R or S and $X_{17}$ is T or S;

wherein the B peptide has at least the following amino acid sequence SEQ ID NO: 45:

$GX_{18}X_{19}X_{20}X_{21}X_{22}X_{23}TSLTGRDX_{24}NX_{25}X_{26}X_{27}GEX_{28}QX_{29}X_{30}STAX_{31}X_{32}X_{33}FLX_{34}$
$X_{35}X_{36}X_{37}NGX_{38}X_{39}WTVX_{40}$ in which $X_{18}$ is L or V, $X_{19}$ is L or F, $X_{20}$ is G or S, $X_{21}$ is C or T, $X_{22}$ is I or V, $X_{23}$ is I or V, $X_{24}$ is K, R or T, $X_{25}$ is Q or E, $X_{26}$ is V or N, $X_{27}$ is D, E or C, $X_{28}$ is V or A, $X_{29}$ is V, I, E or M, $X_{30}$ is L or V, $X_{31}$ is T, K or A, $X_{32}$ is Q or H, $X_{33}$ is S or T, $X_{34}$ is A or G, $X_{35}$ is T or S, $X_{36}$ is C or A, $X_{37}$ is V, I or T, $X_{38}$ is V or A, $X_{39}$ is C or M and $X_{40}$ is Y or F, and has at most the 63 amino acids as described in the following sequence SEQ ID NO:46:

$AX_{41}ITX_{42}YX_{43}X_{44}QTRGX_{18}X_{19}X_{20}X_{21}X_{22}X_{23}TSLTGRDX_{24}$ $NX_{25}X_{26}X_{27}GEX_{28}QX_{29}X_{30}STAX_{31}X_{32}X_{33}FLX_{34}X_{35}X_{36}X_{37}$ $NGX_{38}X_{39}WTVX_{40}HGAGX_{45}X_{46}X_{47}$ in which $X_{18}$ to $X_{40}$ are as defined above and $X_{41}$ is P, S or H, $X_{42}$ is A or T, $X_{43}$ is S, A, T or C, $X_{44}$ is Q or R, $X_{45}$ is S, T or A, $X_{46}$ is K or R and $X_{47}$ is T or I;

wherein the C peptide has at least the following amino acid sequence SEQ ID NO: 127:

$SX_{47}MX_{48}FTX_{49}X_{50}X_{51}TSPLX_{52}X_{53}X_{54}X_{55}TLX_{56}FNIX_{57}$ $GGWVAX_{58}QX_{59}$ in which $X_{47}$, is L or P, $X_{48}$ is A or S, $X_{49}$ is A or S, $X_{50}$ is A or S, $X_{51}$ is I or V, $X_{52}$ is T, S or A, $X_{53}$ is T or I, $X_{54}$ is Q, S or G, $X_{55}$ is N, Q, H, S, Y or T, $X_{56}$ is L or M, $X_{57}$ is L or W, $X_{58}$ is A or S and $X_{59}$ is L, P or I, and has at most the 57 amino acids as described in the following sequence SEQ ID NO:128:

$NFIX_{60}GX_{61}QYLAX_{62}LSTLPGNX_{63}AX_{64}X_{65}SX_{47}MX_{48}FTX_{49}X_{50}$ $X_{51}TSPLX_{52}X_{53}X_{54}X_{55}TLX_{56}FNIX_{57}GGWVAX_{58}QX_{59}X_{66}X_{67}X_{68}$ in which $X_{47}$, to $X_{59}$ are as defined above and $X_{60}$ is T or S, $X_{61}$ is I, T or V, $X_{62}$ is G or A, $X_{63}$ is P or L, $X_{64}$ is I or M, $X_{65}$ is A, V or R, $X_{66}$ is A or R, $X_{67}$ is P, A or D and $X_{68}$ is P, A or S; and wherein the D peptide has at least the following amino acid sequence SEQ ID NO: 174:

$X_{69}KX_{70}ARX_{71}IVX_{72}PX_{73}LGX_{74}RVCEKX_{75}ALX_{76}X_{77}VX_{78}X_{79}$ $X_{80}X_{81}$, in which $X_{69}$ is R or Q, $X_{70}$ is P or A, $X_{71}$ is L or F, $X_{72}$ is F or Y, $X_{73}$ is D or E, $X_{74}$ is V or S, $X_{75}$ is M or R, $X_{76}$ is Y or H, $X_{77}$ is D or N, $X_{78}$ is V or I, $X_{79}$ is S, T or K, $X_{80}$ is T, K, I or N and $X_{81}$ is L or T, and has at most the 44 amino acids as defined in the following sequence ID NO:175:

$KGGX_{69}KX_{70}ARX_{71}IVX_{72}PX_{73}LGX_{74}RVCEKX_{75}ALX_{76}X_{77}VX_{78}$ $X_{79}X_{80}X_{81}X_{82}X_{83}X_{84}VMGX_{85}X_{86}YX_{87}X_{88}Q$, in which $X_{69}$ to $X_{81}$ are as defined above and $X_{82}$ is P or A, $X_{83}$ is Q, L, H, R, K or P, $X_{84}$ is A, T, V or P, $X_{85}$ is P, S or A, $X_{86}$ is S or A, $X_{87}$ is G or R and $X_{88}$ is F or C.

2. Nucleotide sequences coding for any one of the following A to D peptides, wherein the A peptide has at least the following amino acid sequence SEQ ID NO: 1:

$X_{1}AX_{9}QGYKVX_{3}VLNPSVX_{4}ATLX_{5}FGX_{6}YMSKAX_{7}GX_{8}$, in which $X_1$ is Y or H, $X_2$ is A, G or T, $X_3$ is R or L, $X_4$ is A or T, $X_5$ is G or S, $X_6$ is A, T or V, $X_7$ is H or Y and $X_8$ is I, T, M or V, and has at most the 46 amino acids as defined in the following sequence SEQ ID NO:2:

$SX_{9}X_{10}VPX_{11}X_{12}X_{1}AX_{2}QGYKVX_{3}VLNPSVX_{4}ATLX_{5}FGX_{6}$ $YMSKAX_{7}GX_{8}X_{13}PX_{14}X_{15}X_{16}X_{17}GV$, in which $X_1$ to $X_8$ are as defined above, and $X_9$ is T or N, $X_{10}$ is K or R, $X_{11}$ is A or V, $X_{12}$ is A or E, $X_{13}$ is E or D, $X_{14}$ is N or S, $X_{15}$ is I, L or V, $X_{16}$ is R or S and $X_{17}$ is T or S;

wherein the B peptide has at least the following amino acid sequence SEQ ID NO: 45:

$GX_{18}X_{19}X_{20}X_{21}X_{22}X_{23}TSLTGRDX_{24}NX_{25}X_{26}X_{27}GEX_{28}QX_{29}$ $X_{30}STAX_{31}X_{32}X_{33}FLX_{34}X_{35}X_{36}X_{37}NGX_{38}X_{39}WTVX_{40}$ in which $X_{18}$ is L or V, $X_{19}$ is L or F, $X_{20}$ is G or S, $X_{21}$ is C or T, $X_{22}$ is I or V, $X_{23}$ is I or V, $X_{24}$ is K, R or T, $X_{25}$ is Q or E, $X_{26}$ is V or N, $X_{27}$ is D, E or C, $X_{28}$ is V or A, $X_{29}$ is V, I, E or M, $X_{30}$ is L or V, $X_{31}$ is T, K or A, $X_{32}$ is Q or H, $X_{33}$ is S or T, $X_{34}$ is A or G, $X_{35}$ is T or S, $X_{36}$ is C or A, $X_{37}$ is V, I or T, $X_{38}$ is V or A, $X_{39}$ is C or M and $X_{40}$ is Y or F, and has at most the 63 amino acids as described in the following sequence SEQ ID NO:46:

$AX_{41}ITX_{42}YX_{43}X_{44}QTRGX_{18}X_{19}X_{20}X_{21}X_{22}X_{23}TSLTGRDX_{24}$ $NN_{25}X_{26}X_{27}GEX_{28}QX_{29}X_{30}STAX_{31}X_{32}X_{33}FLX_{34}X_{35}X_{36}X_{37}$ $NGX_{38}X_{39}WTVX_{40}HGAGX_{45}X_{46}X_{47}$ in which $X_{18}$ to $X_{40}$ are as defined above and $X_{41}$ is P, S or H, $X_{42}$ is A or T, $X_{43}$ is S, A, T or C, $X_{44}$ is Q or R, $X_{45}$ is S, T or A, $X_{46}$ is K or R and $X_{47}$ is T or I;

wherein the C peptide has at least the following amino acid sequence SEQ ID NO: 127:

$SX_{47}MX_{48}FTX_{49}X_{50}X_{51}TSPLX_{52}X_{53}X_{54}X_{55}TLX_{56}FNIX_{57}$ $GGWVAX_{58}QX_{59}$ in which $X_{47}$, is L or P, $X_{48}$ is A or S, $X_{49}$ is A or S, $X_{50}$ is A or S, $X_{51}$ is I or V, $X_{52}$ is T, S or A, $X_{53}$ is T or I, $X_{54}$ is Q, S or G, $X_{55}$ is N, Q, H, S, Y or T, $X_{56}$ is L or M, $X_{57}$ is L or W, $X_{58}$ is A or S and $X_{59}$ is L, P or I, and has at most the 57 amino acids as described in the following sequence SEQ ID NO:128:

$NFIX_{60}GX_{61}QYLAX_{62}LSTLPGNX_{63}AX_{64}X_{65}SX_{47}MX_{48}$ $FTX_{49}X_{50}X_{51}TSPLX_{52}X_{53}X_{54}X_{55}TLX_{56}FNIX_{57}$ $GGWVAX_{58}QX_{59}X_{66}X_{67}X_{68}$ in which $X_{47}$, to $X_{59}$ are as defined above and $X_{60}$ is T or S, $X_{61}$ is I, T or V, $X_{62}$ is G or A, $X_{63}$ is P or L, $X_{64}$ is I or M, $X_{65}$ is A, V or R, $X_{66}$ is A or R, $X_{67}$ is P, A or D and $X_{68}$ is P, A or S; and wherein the D peptide has at least the following amino acid sequence SEQ ID NO: 174:

$X_{69}KX_{70}ARX_{71}IVX_{72}PX_{73}LGX_{74}RVCEKX_{75}ALX_{76}X_{77}VX_{78}X_{79}$

-continued $X_{80}X_{81}$, in which $X_{69}$ is R or Q, $X_{70}$ is P or A, $X_{71}$ is L or F, $X_{72}$ is F or Y, $X_{73}$ is D or E, $X_{74}$ is V or S, $X_{75}$ is M or R, $X_{76}$ is Y or H, $X_{77}$ is D or N, $X_{78}$ is V or I, $X_{79}$ is S, T or K, $X_{80}$ is T, K, I or N and $X_{81}$ is L or T, and has at most the 44 amino acids as defined in the following sequence ID NO:175:

$KGGX_{69}KX_{70}ARX_{71}WX_{72}PX_{73}LGX_{74}RVCEKX_{75}ALX_{76}X_{77}VX_{78}$ $X_{79}X_{80}X_{81}X_{82}X_{83}X_{84}VMGX_{85}X_{86}YX_{87}X_{88}Q$, in which $X_{69}$ to $X_{81}$ are as defined above and $X_{82}$ is P or A, $X_{83}$ is Q, L, H, R, K or P, $X_{84}$ is A, T, V or P, $X_{85}$ is P, S or A, $X_{86}$ is S or A, $X_{87}$ is G or R and $X_{88}$ is F or C.

3. The nucleotide sequences of claim 2, wherein the A peptide is chosen from the following peptides:

the peptides having at least sequence SEQ ID NO: 3 and at most sequence SEQ ID NO: 19, the peptides having at least sequence SEQ ID NO: 4 and at most a sequence chosen from:
i) sequence SEQ ID NO: 20,
ii) sequence SEQ ID NO: 24,
iii) sequence SEQ ID NO: 32 and
iv) sequence SEQ ID NO: 34, the peptides having at least sequence SEQ ID NO: 5 and at most a sequence chosen from:
i) sequence SEQ ID NO: 21,
ii) sequence SEQ ID NO: 28 and
iii) sequence SEQ ID NO: 36, the peptides having at least sequence SEQ ID NO: 6 and at most a sequence chosen from:
i) sequence SEQ ID NO: 22,
ii) sequence SEQ ID NO: 27 and
iii) sequence SEQ ID NO: 41, the peptides having at least sequence SEQ ID NO: 7 and at most a sequence chosen from:
i) sequence SEQ ID NO: 23 and
ii) sequence SEQ ID NO: 37, the peptides having at least sequence SEQ ID NO: 8 and at most sequence SEQ ID NO: 25, the peptides having at least sequence SEQ ID NO: 9 and at most sequence SEQ ID NO: 26, the peptides having at least sequence SEQ ID NO: 10 and at most sequence SEQ ID NO: 29, the peptides having at least sequence SEQ ID NO: 11 and at most sequence SEQ ID NO: 30, the peptides having at least sequence SEQ ID NO: 12 and at most sequence SEQ ID NO: 31, the peptides having at least sequence SEQ ID NO: 13 and at most sequence SEQ ID NO: 33, the peptides having at least sequence SEQ ID NO: 14 and at most a sequence chosen from:
i) sequence SEQ ID NO: 35 and
ii) sequence SEQ ID NO: 39, the peptides having at least sequence SEQ ID NO: 15 and at most sequence SEQ ID NO: 38, the peptides having at least sequence SEQ ID NO: 16 and at most a sequence chosen from:
i) sequence SEQ ID NO: 40 and
ii) sequence SEQ ID NO: 42, the peptides having at least sequence SEQ ID NO: 17 and at most sequence SEQ ID NO: 43, and the peptides having at least sequence SEQ ID NO: 18 and at most sequence SEQ ID NO: 44.

4. The nucleotide sequence of claim 3, wherein the A peptide is chosen from the peptides of sequences SEQ ID NO: 3 to 18.

5. The nucleotide sequences of claim 2, wherein the B peptide is chosen from:

the peptides having at least sequence SEQ ID NO: 47 and at most sequence SEQ ID NO: 81, the peptides having at least sequence SEQ ID NO: 48 and at most sequence SEQ ID NO: 82, the peptides having at least sequence SEQ ID NO: 49 and at most sequence SEQ ID NO: 83, the peptides having at least sequence SEQ ID NO: 50 and at most a sequence chosen from sequences SEQ ID NO: 84, SEQ ID NO: 90, SEQ ID NO: 105, SEQ ID NO: 107 and SEQ ID NO: 116, the peptides having at least sequence SEQ ID NO: 51 and at most a sequence chosen from sequences SEQ ID NO: 85 and SEQ ID NO: 124, the peptides having at least sequence SEQ ID NO: 52 and at most a sequence chosen from sequences SEQ ID NO: 86 and SEQ ID NO: 120, the peptides having at least sequence SEQ ID NO: 53 and at most sequence SEQ ID NO: 87, the peptides having at least sequence SEQ ID NO: 54 and at most a sequence chosen from sequences SEQ ID NO: 88 and SEQ ID NO: 117, the peptides having at least sequence SEQ ID NO: 55 and at most sequence SEQ ID NO: 89, the peptides having at least sequence SEQ ID NO: 56 and at most a sequence chosen from sequences SEQ ID NO: 91 and SEQ ID NO: 92, the peptides having at least sequence SEQ ID NO: 57 and at most sequence SEQ ID NO: 93, the peptides having at least sequence SEQ ID NO: 58 and at most a sequence chosen from sequences SEQ ID NO: 94 and SEQ ID NO: 110, the peptides having at least sequence SEQ ID NO: 59 and at most sequence SEQ ID NO: 95, the peptides having at least sequence SEQ ID NO: 60 and at most a sequence chosen from sequences SEQ ID NO: 96 and SEQ ID NO: 115, the peptides having at least sequence SEQ ID NO: 61 and at most sequence SEQ ID NO: 97, the peptides having at least sequence SEQ ID NO: 62 and at most a sequence chosen from sequences SEQ ID NO: 98 and SEQ ID NO: 109, the peptides having at least sequence SEQ ID NO: 63 and at most sequence SEQ ID NO: 99, the peptides having at least sequence SEQ ID NO: 64 and at most sequence SEQ ID NO: 100, the peptides having at least sequence SEQ ID NO: 65 and at most sequence SEQ ID NO: 101, the peptides having at least sequence SEQ ID NO: 66 and at most sequence SEQ ID NO: 102, the peptides having at least sequence SEQ ID NO: 67 and at most sequence SEQ ID NO: 103, the peptides having at least sequence SEQ ID NO: 68 and at most sequence SEQ ID NO: 104, the peptides having at least sequence SEQ ID NO: 69 and at most sequence SEQ ID NO: 106, the peptides having at least sequence SEQ ID NO: 70 and at most sequence SEQ ID NO: 108, the peptides having at least sequence SEQ ID NO: 71 and at most sequence SEQ ID NO: 111, the peptides having at least sequence SEQ ID NO: 72 and at most sequence SEQ ID NO: 112, the peptides having at least sequence SEQ ID NO: 73 and at most sequence SEQ ID NO: 113, the peptides having at least sequence SEQ ID NO: 74 and at most sequence SEQ ID NO: 114, the peptides having at least sequence SEQ ID NO: 75 and at most a sequence chosen from sequences SEQ ID NO: 118 and SEQ ID NO: 119, the peptides having at least sequence SEQ ID NO: 76 and at most sequence SEQ ID NO: 121, the peptides having at least sequence SEQ ID NO: 77 and at most sequence SEQ ID NO: 122, the peptides having at least sequence SEQ ID NO: 78 and at most sequence SEQ ID NO: 123, the peptides having at least sequence SEQ ID NO: 79 and at most sequence SEQ ID NO: 125, and the peptides having at least sequence SEQ ID NO: 80 and at most sequence SEQ ID NO: 126.

6. The nucleotide sequence of claim 5, wherein the B peptide is chosen from the peptides of sequences SEQ ID NO: 47 to 80.

7. The nucleotide sequence of claim 2, wherein the C peptide is chosen from:

the peptides having at least sequence SEQ ID NO: 129 and at most a sequence chosen from sequences SEQ ID NO: 147, SEQ ID NO: 153, SEQ ID NO: 162 and SEQ ID NO: 167, the peptides having at least sequence SEQ ID NO: 130 and at most a sequence chosen from sequences SEQ ID NO: 148 and SEQ ID NO: 150, the peptides having at least sequence SEQ ID NO: 131 and at most sequence SEQ ID NO: 149, the peptides having at least sequence SEQ ID NO: 132 and at most a sequence chosen from sequences SEQ ID NO: 151, SEQ ID NO: 155, SEQ ID NO: 168 and SEQ ID NO: 171, the peptides having at least sequence SEQ ID NO: 133 and at most sequence SEQ ID NO: 152, the peptides having at least sequence SEQ ID NO: 134 and at most a sequence chosen from sequences SEQ ID NO: 154 and SEQ ID NO: 169, the peptides having at least sequence SEQ ID NO: 135 and at most sequence SEQ ID NO: 156, the peptides having at least sequence SEQ ID NO: 136 and at most a sequence chosen from sequences SEQ ID NO: 157 and SEQ ID NO: 170, the peptides having at least sequence SEQ ID NO: 137 and at most sequence SEQ ID NO: 158, the peptides having at least sequence SEQ ID NO: 138 and at most sequence SEQ ID NO: 159, the peptides having at least sequence SEQ ID NO: 139 and at most sequence SEQ ID NO: 160, the peptides having at least sequence SEQ ID NO: 140 and at most sequence SEQ ID NO: 161, the peptides having at least sequence SEQ ID NO: 141 and at most sequence SEQ ID NO: 163, the peptides having at least sequence SEQ ID NO: 142 and at most sequence SEQ ID NO: 164, the peptides having at least sequence SEQ ID NO: 143 and at most sequence SEQ ID NO: 165, the peptides having at least sequence SEQ ID NO: 144 and at most sequence SEQ ID NO: 166, the peptides having at least sequence SEQ ID NO: 145 and at most sequence SEQ ID NO: 172, and the peptides having at least sequence SEQ ID NO: 146 and at most sequence SEQ ID NO: 173.

8. The nucleotide sequence of claim 7, wherein the C peptide is chosen from sequences SEQ ID NO: 129 to 146.

9. The nucleotide sequence of claim 2, wherein the D peptide is chosen from:

the peptides having at least sequence SEQ ID NO: 176 and at most a sequence chosen from:
i) sequence SEQ ID NO: 188,
ii) sequence SEQ ID NO: 192,
iii) sequence SEQ ID NO: 193,
iv) sequence SEQ ID NO: 194,
v) sequence SEQ ID NO: 201,
vi) sequence SEQ ID NO: 202,
vii) sequence SEQ ID NO: 203,
viii) sequence SEQ ID NO: 204,
ix) sequence SEQ ID NO: 205 and
x) sequence SEQ ID NO: 210, the peptides having at least sequence SEQ ID NO: 177 and at most a sequence chosen from:
i) sequence SEQ ID NO: 189 and
ii) sequence SEQ ID NO: 190, the peptides having at least sequence SEQ ID NO: 178 and at most sequence SEQ ID NO: 191, the peptides having at least sequence SEQ ID NO: 179 and at most sequence SEQ ID NO: 195, the peptides having at least sequence SEQ ID NO: 180 and at most a sequence chosen from:
i) sequence SEQ ID NO: 196 and
ii) sequence SEQ ID NO: 206, the peptides having at least sequence SEQ ID NO: 181 and at most sequence SEQ ID NO: 197, the peptides having at least sequence SEQ ID NO: 182 and at most a sequence chosen from:
i) sequence SEQ ID NO: 198 and
ii) sequence SEQ ID NO: 209, the peptides having at least sequence SEQ ID NO: 183 and at most a sequence chosen from:
i) sequence SEQ ID NO: 199 and
ii) sequence SEQ ID NO: 200, the peptides having at least sequence SEQ ID NO: 184 and at most sequence SEQ ID NO: 207, the peptides having at least sequence SEQ ID NO: 185 and at most sequence SEQ ID NO: 208, the peptides having at least sequence SEQ ID NO: 186 and at most sequence SEQ ID NO: 211, the peptides having at least sequence SEQ ID NO: 187 and at most sequence SEQ ID NO: 212.

10. The nucleotide sequence of claim 9, wherein the D peptide is chosen from the peptides of sequences SEQ ID NO: 176 to 187.

11. An expression vector comprising a nucleotide sequence according to claim 2, as well as the means for its expression.

12. An expression vector comprising a nucleotide sequence, wherein the nucleotide sequence codes for an A peptide as defined in claim 4, as well as the means for its expression.

13. An expression vector comprising a nucleotide sequence, wherein the nucleotide sequence codes for an B peptide as defined in claim 6, as well as the means for its expression.

14. An expression vector comprising a nucleotide sequence, wherein the nucleotide sequence codes for an C peptide as defined in claim 8, as well as the means for its expression.

15. An expression vector comprising a nucleotide sequence, wherein the nucleotide sequence codes for an D peptide as defined in claim 10, as well as the means for its expression.

16. An expression vector comprising at least two nucleotide sequences according to claim 2 coding for the A to D peptides, as well as the means for their expression, each nucleotide sequence coding for a different peptide.

17. The expression vector of claim 16, wherein the nucleotide sequences code for the A and B peptides, A and C peptides, A and D peptides, B and C peptides, B and D peptides, or C and D peptides.

18. An expression vector, comprising at least three nucleotide sequences according to claim 2 coding for the A to D peptides, as well as the means for their expression, each nucleotide sequence coding for a different peptide.

19. The expression vector of claim 18, wherein the nucleotide sequences code for the A, B and C peptides, A, B and D peptides, A, C and D peptides, or B, C and D peptides.

20. An expression vector, comprising four nucleotide sequences according to claim 2 coding for the A to D peptides, as well as the means for their expression, each nucleotide sequence coding for a different peptide.

21. An expression vector comprising two to four nucleotide sequences according to claim 2 chosen from those coding for the A to D peptides and a nucleotide sequence coding for the B' epitope (SEQ ID NO: 213) or C' epitope (SEQ ID NO: 221), provided that:

the nucleotide sequence coding for the B peptide and the nucleotide sequence coding for the B' epitope are not present at the same time; and the nucleotide sequence coding for the C peptide and the nucleotide sequence coding for the C' epitope are not present at the same time.

22. An isolated microorganism or a host cell transformed by the expression vector of claim 11.

23. An isolated microorganism or a host cell transformed by the expression vector of claim 16 or 18.

24. An isolated microorganism or a host cell transformed by the expression vector of claim 20 or 21.

25. An isolated microorganism or a host cell which is co-transformed with at least two expression vectors according to claim 11, each expression vector coding for a different peptide.

26. An isolated microorganism or host cell which is co-transformed with four expression vectors according to claim 11 coding respectively for the A, B, C and D peptides.

* * * * *

UNITED STATES PATENT AND TRADEMARK OFFICE

CERTIFICATE OF CORRECTION

PATENT NO. : 8,067,228 B2
APPLICATION NO. : 12/211385
DATED : November 29, 2011
INVENTOR(S) : Fournillier et al.

It is certified that error appears in the above-identified patent and that said Letters Patent is hereby corrected as shown below:

Column 165, Claim 2, Line 63, SEQ ID NO: 1, replace "$X_1AX_9$" with --$X_1AX_2$--.

Column 166, Claim 2, Line 31, SEQ ID NO: 46, replace "$NN_{25}$" with --$NX_{25}$--.

Signed and Sealed this
Nineteenth Day of February, 2013

Teresa Stanek Rea
*Acting Director of the United States Patent and Trademark Office*

SEQUENCE LISTING

<160> NUMBER OF SEQ ID NOS: 239

<210> SEQ ID NO 1
<211> LENGTH: 31
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (1)..(1)
<223> OTHER INFORMATION: Xaa = Y or H
<220> FEATURE:
<221> NAME/KEY: MISC_FEATURE
<222> LOCATION: (3)..(3)
<223> OTHER INFORMATION: Xaa = A, G, or T
<220> FEATURE:
<221> NAME/KEY: MISC_FEATURE
<222> LOCATION: (9)..(9)
<223> OTHER INFORMATION: Xaa = R or L
<220> FEATURE:
<221> NAME/KEY: MISC_FEATURE
<222> LOCATION: (16)..(16)
<223> OTHER INFORMATION: Xaa = A or T
<220> FEATURE:
<221> NAME/KEY: MISC_FEATURE
<222> LOCATION: (20)..(20)
<223> OTHER INFORMATION: Xaa = G or S
<220> FEATURE:
<221> NAME/KEY: MISC_FEATURE
<222> LOCATION: (23)..(23)
<223> OTHER INFORMATION: Xaa = A, T, or V
<220> FEATURE:
<221> NAME/KEY: MISC_FEATURE
<222> LOCATION: (29)..(29)
<223> OTHER INFORMATION: Xaa = H or Y
<220> FEATURE:
<221> NAME/KEY: MISC_FEATURE
<222> LOCATION: (31)..(31)
<223> OTHER INFORMATION: Xaa = I, T, M or V

<400> SEQUENCE: 1

```
Xaa Ala Xaa Gln Gly Tyr Lys Val Xaa Val Leu Asn Pro Ser Val Xaa
1               5                   10                  15

Ala Thr Leu Xaa Phe Gly Xaa Tyr Met Ser Lys Ala Xaa Gly Xaa
            20                  25                  30
```

<210> SEQ ID NO 2
<211> LENGTH: 46
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (2)..(2)
<223> OTHER INFORMATION: Xaa = T or N
<220> FEATURE:
<221> NAME/KEY: MISC_FEATURE
<222> LOCATION: (3)..(3)
<223> OTHER INFORMATION: Xaa = K or R
<220> FEATURE:
<221> NAME/KEY: MISC_FEATURE
<222> LOCATION: (6)..(6)
<223> OTHER INFORMATION: Xaa = A or V
<220> FEATURE:
<221> NAME/KEY: MISC_FEATURE
<222> LOCATION: (7)..(7)
<223> OTHER INFORMATION: Xaa = A or E
<220> FEATURE:
<221> NAME/KEY: MISC_FEATURE
<222> LOCATION: (8)..(8)
<223> OTHER INFORMATION: Xaa = Y or H
<220> FEATURE:

<221> NAME/KEY: MISC_FEATURE
<222> LOCATION: (10)..(10)
<223> OTHER INFORMATION: Xaa = A, G, or T
<220> FEATURE:
<221> NAME/KEY: MISC_FEATURE
<222> LOCATION: (16)..(16)
<223> OTHER INFORMATION: Xaa = R or L
<220> FEATURE:
<221> NAME/KEY: MISC_FEATURE
<222> LOCATION: (23)..(23)
<223> OTHER INFORMATION: Xaa = A or T
<220> FEATURE:
<221> NAME/KEY: MISC_FEATURE
<222> LOCATION: (27)..(27)
<223> OTHER INFORMATION: Xaa = G or S
<220> FEATURE:
<221> NAME/KEY: MISC_FEATURE
<222> LOCATION: (30)..(30)
<223> OTHER INFORMATION: Xaa = A, T, or V
<220> FEATURE:
<221> NAME/KEY: MISC_FEATURE
<222> LOCATION: (36)..(36)
<223> OTHER INFORMATION: Xaa = H or Y
<220> FEATURE:
<221> NAME/KEY: MISC_FEATURE
<222> LOCATION: (38)..(38)
<223> OTHER INFORMATION: Xaa = I, T, M or V
<220> FEATURE:
<221> NAME/KEY: MISC_FEATURE
<222> LOCATION: (39)..(39)
<223> OTHER INFORMATION: Xaa = E or D
<220> FEATURE:
<221> NAME/KEY: MISC_FEATURE
<222> LOCATION: (41)..(41)
<223> OTHER INFORMATION: Xaa = N or S
<220> FEATURE:
<221> NAME/KEY: MISC_FEATURE
<222> LOCATION: (42)..(42)
<223> OTHER INFORMATION: Xaa = I, L or V
<220> FEATURE:
<221> NAME/KEY: MISC_FEATURE
<222> LOCATION: (43)..(43)
<223> OTHER INFORMATION: Xaa = R or S
<220> FEATURE:
<221> NAME/KEY: MISC_FEATURE
<222> LOCATION: (44)..(44)
<223> OTHER INFORMATION: Xaa = T or S

<400> SEQUENCE: 2

```
Ser Xaa Xaa Val Pro Xaa Xaa Xaa Ala Xaa Gln Gly Tyr Lys Val Xaa
1               5                   10                  15

Val Leu Asn Pro Ser Val Xaa Ala Thr Leu Xaa Phe Gly Xaa Tyr Met
            20                  25                  30

Ser Lys Ala Xaa Gly Xaa Xaa Pro Xaa Xaa Xaa Xaa Gly Val
        35                  40                  45
```

<210> SEQ ID NO 3
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 3

```
Tyr Ala Ala Gln Gly Tyr Lys Val Arg Val Leu Asn Pro Ser Val Ala
1               5                   10                  15

Ala Thr Leu Gly Phe Gly Ala Tyr Met Ser Lys Ala His Gly Ile
            20                  25                  30
```

<210> SEQ ID NO 4
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 4

Tyr Ala Ala Gln Gly Tyr Lys Val Leu Val Leu Asn Pro Ser Val Ala
1 5 10 15

Ala Thr Leu Gly Phe Gly Ala Tyr Met Ser Lys Ala His Gly Ile
20 25 30

<210> SEQ ID NO 5
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 5

Tyr Ala Ala Gln Gly Tyr Lys Val Leu Val Leu Asn Pro Ser Val Ala
1 5 10 15

Ala Thr Leu Gly Phe Gly Ala Tyr Met Ser Lys Ala His Gly Val
20 25 30

<210> SEQ ID NO 6
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 6

Tyr Ala Ala Gln Gly Tyr Lys Val Leu Val Leu Asn Pro Ser Val Ala
1 5 10 15

Ala Thr Leu Gly Phe Gly Ala Tyr Met Ser Lys Ala His Gly Thr
20 25 30

<210> SEQ ID NO 7
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 7

Tyr Ala Ala Gln Gly Tyr Lys Val Leu Val Leu Asn Pro Ser Val Ala
1 5 10 15

Ala Thr Leu Gly Phe Gly Ala Tyr Met Ser Lys Ala Tyr Gly Thr
20 25 30

<210> SEQ ID NO 8
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 8

Tyr Ala Ala Gln Gly Tyr Lys Val Leu Val Leu Asn Pro Ser Val Ala
1 5 10 15

Ala Thr Leu Ser Phe Gly Ala Tyr Met Ser Lys Ala His Gly Thr
20 25 30

<210> SEQ ID NO 9
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 9

Tyr Ala Ala Gln Gly Tyr Lys Val Leu Val Leu Asn Pro Ser Val Ala
1 5 10 15

Ala Thr Leu Gly Phe Gly Ala Tyr Met Ser Lys Ala Tyr Gly Ile
20 25 30

<210> SEQ ID NO 10
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 10

Tyr Ala Ala Gln Gly Tyr Lys Val Leu Val Leu Asn Pro Ser Val Thr
1 5 10 15

Ala Thr Leu Gly Phe Gly Ala Tyr Met Ser Lys Ala His Gly Val
20 25 30

<210> SEQ ID NO 11
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 11

Tyr Ala Gly Gln Gly Tyr Lys Val Leu Val Leu Asn Pro Ser Val Ala
1 5 10 15

Ala Thr Leu Gly Phe Gly Ala Tyr Met Ser Lys Ala His Gly Ile
20 25 30

<210> SEQ ID NO 12
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 12

Tyr Ala Ala Gln Gly Tyr Lys Val Leu Val Leu Asn Pro Ser Val Ala
1 5 10 15

Ala Thr Leu Ser Phe Gly Ala Tyr Met Ser Lys Ala His Gly Ile
20 25 30

<210> SEQ ID NO 13
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 13

Tyr Ala Thr Gln Gly Tyr Lys Val Leu Val Leu Asn Pro Ser Val Ala
1 5 10 15

Ala Thr Leu Gly Phe Gly Ala Tyr Met Ser Lys Ala His Gly Thr
20 25 30

<210> SEQ ID NO 14
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 14

Tyr Ala Ala Gln Gly Tyr Lys Val Leu Val Leu Asn Pro Ser Val Ala
1 5 10 15

Ala Thr Leu Ser Phe Gly Ala Tyr Met Ser Lys Ala His Gly Val
20 25 30

<210> SEQ ID NO 15
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 15

Tyr Ala Thr Gln Gly Tyr Lys Val Leu Val Leu Asn Pro Ser Val Ala
1 5 10 15

Ala Thr Leu Ser Phe Gly Ala Tyr Met Ser Lys Ala Tyr Gly Met
20 25 30

<210> SEQ ID NO 16
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 16

Tyr Ala Ala Gln Gly Tyr Lys Val Leu Val Leu Asn Pro Ser Val Ala
1 5 10 15

Ala Thr Leu Ser Phe Gly Ala Tyr Met Ser Lys Ala Tyr Gly Val
20 25 30

<210> SEQ ID NO 17
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 17

Tyr Ala Ala Gln Gly Tyr Lys Val Leu Val Leu Asn Pro Ser Val Ala
1 5 10 15

Ala Thr Leu Gly Phe Gly Thr Tyr Met Ser Lys Ala Tyr Gly Thr
20 25 30

<210> SEQ ID NO 18
<211> LENGTH: 31
<212> TYPE: PRT
<213> ORGANISM: artificial sequence
<220> FEATURE:
<223> OTHER INFORMATION: anti-VHC immunogenic peptide

<400> SEQUENCE: 18

His Ala Ala Gln Gly Tyr Lys Val Leu Val Leu Asn Pro Ser Val Ala
1 5 10 15

Ala Thr Leu Gly Phe Gly Val Tyr Met Ser Lys Ala Tyr Gly Ile
20 25 30

<210> SEQ ID NO 19
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 19

Ser Thr Lys Val Pro Ala Ala Tyr Ala Ala Gln Gly Tyr Lys Val Arg
1 5 10 15

Val Leu Asn Pro Ser Val Ala Ala Thr Leu Gly Phe Gly Ala Tyr Met
20 25 30

Ser Lys Ala His Gly Ile Glu Pro Asn Ile Arg Thr Gly Val
35 40 45

<210> SEQ ID NO 20
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 20

Ser Thr Lys Val Pro Ala Ala Tyr Ala Ala Gln Gly Tyr Lys Val Leu
1 5 10 15

Val Leu Asn Pro Ser Val Ala Ala Thr Leu Gly Phe Gly Ala Tyr Met
20 25 30

Ser Lys Ala His Gly Ile Asp Pro Asn Ile Arg Thr Gly Val
35 40 45

<210> SEQ ID NO 21
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 21

Ser Thr Lys Val Pro Ala Ala Tyr Ala Ala Gln Gly Tyr Lys Val Leu
1 5 10 15

Val Leu Asn Pro Ser Val Ala Ala Thr Leu Gly Phe Gly Ala Tyr Met
20 25 30

Ser Lys Ala Tyr Gly Val Asp Pro Asn Val Arg Thr Gly Val
35 40 45

<210> SEQ ID NO 22
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 22

Ser Thr Lys Val Pro Ala Ala Tyr Ala Ala Gln Gly Tyr Lys Val Leu
1 5 10 15

Val Leu Asn Pro Ser Val Ala Ala Thr Leu Gly Phe Gly Ala Tyr Met
20 25 30

Ser Lys Ala His Gly Thr Asp Pro Asn Ile Arg Thr Gly Val
35 40 45

<210> SEQ ID NO 23
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 23

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala Tyr Gly Thr Asp Pro Asn Ile Arg Thr Gly Val
        35                  40                  45


<210> SEQ ID NO 24
<211> LENGTH: 46
<212> TYPE: PRT
<213> ORGANISM: Artificial Sequence
<220> FEATURE:
<223> OTHER INFORMATION: anti-VHC immunogenic peptide

<400> SEQUENCE: 24

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Ile Glu Pro Asn Ile Arg Thr Gly Val
        35                  40                  45


<210> SEQ ID NO 25
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 25

Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala His Gly Thr Asp Pro Asn Ile Arg Thr Gly Val
        35                  40                  45


<210> SEQ ID NO 26
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 26

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala Tyr Gly Ile Asp Pro Asn Val Arg Thr Gly Val
        35                  40                  45


<210> SEQ ID NO 27
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 27

Ser Thr Lys Val Pro Ala Ala Tyr Ala Ala Gln Gly Tyr Lys Val Leu
1               5                   10                  15
```

```
Val Leu Asn Pro Ser Val Ala Ala Thr Leu Gly Phe Gly Ala Tyr Met
            20                  25                  30

Ser Lys Ala His Gly Thr Glu Pro Asn Ile Arg Thr Gly Val
        35                  40                  45


<210> SEQ ID NO 28
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 28

Ser Asn Lys Val Pro Val Glu Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Val Asp Pro Asn Ile Arg Thr Gly Val
        35                  40                  45


<210> SEQ ID NO 29
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 29

Ser Thr Lys Val Pro Ala Ala Tyr Ala Ala Gln Gly Tyr Lys Val Leu
1               5                   10                  15

Val Leu Asn Pro Ser Val Thr Ala Thr Leu Gly Phe Gly Ala Tyr Met
            20                  25                  30

Ser Lys Ala His Gly Val Asp Pro Asn Ile Arg Thr Gly Val
        35                  40                  45


<210> SEQ ID NO 30
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 30

Ser Thr Lys Val Pro Ala Ala Tyr Ala Gly Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Ile Asp Pro Asn Ile Arg Thr Gly Val
        35                  40                  45


<210> SEQ ID NO 31
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 31

Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala His Gly Ile Asp Pro Asn Ile Arg Thr Gly Val
```

35 40 45

<210> SEQ ID NO 32
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 32

Ser Thr Arg Val Pro Ala Ala Tyr Ala Ala Gln Gly Tyr Lys Val Leu
1 5 10 15

Val Leu Asn Pro Ser Val Ala Ala Thr Leu Gly Phe Gly Ala Tyr Met
20 25 30

Ser Lys Ala His Gly Ile Asp Pro Asn Leu Arg Thr Gly Val
35 40 45

<210> SEQ ID NO 33
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 33

Ser Thr Lys Val Pro Ala Ala Tyr Ala Thr Gln Gly Tyr Lys Val Leu
1 5 10 15

Val Leu Asn Pro Ser Val Ala Ala Thr Leu Gly Phe Gly Ala Tyr Met
20 25 30

Ser Lys Ala His Gly Thr Asp Pro Asn Ile Arg Thr Gly Val
35 40 45

<210> SEQ ID NO 34
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 34

Ser Thr Lys Val Pro Ala Ala Tyr Ala Ala Gln Gly Tyr Lys Val Leu
1 5 10 15

Val Leu Asn Pro Ser Val Ala Ala Thr Leu Gly Phe Gly Ala Tyr Met
20 25 30

Ser Lys Ala His Gly Ile Asp Pro Asn Val Arg Thr Gly Val
35 40 45

<210> SEQ ID NO 35
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 35

Ser Thr Lys Val Pro Ala Ala Tyr Ala Ala Gln Gly Tyr Lys Val Leu
1 5 10 15

Val Leu Asn Pro Ser Val Ala Ala Thr Leu Ser Phe Gly Ala Tyr Met
20 25 30

Ser Lys Ala His Gly Val Asp Pro Ser Ile Arg Thr Gly Val
35 40 45

<210> SEQ ID NO 36

```
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 36

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Val Asp Pro Asn Ile Ser Thr Gly Val
        35                  40                  45


<210> SEQ ID NO 37
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 37

Ser Thr Lys Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala Tyr Gly Thr Asp Pro Asn Val Arg Thr Gly Val
        35                  40                  45


<210> SEQ ID NO 38
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 38

Ser Thr Lys Val Pro Ala Ala Tyr Ala Thr Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala Tyr Gly Met Asp Pro Asn Leu Arg Thr Gly Val
        35                  40                  45


<210> SEQ ID NO 39
<211> LENGTH: 46
<212> TYPE: PRT
<213> ORGANISM: Artificial Sequence
<220> FEATURE:
<223> OTHER INFORMATION: anti-VHC immunogenic peptide

<400> SEQUENCE: 39

Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala His Gly Val Asp Pro Asn Ile Arg Thr Gly Val
        35                  40                  45


<210> SEQ ID NO 40
<211> LENGTH: 46
<212> TYPE: PRT
<213> ORGANISM: artificial sequence
<220> FEATURE:
```

<223> OTHER INFORMATION: anti-VHC immunogenic peptide

<400> SEQUENCE: 40

```
Ser Thr Lys Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala Tyr Gly Val Asp Pro Asn Ile Arg Thr Gly Val
        35                  40                  45
```

<210> SEQ ID NO 41
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 41

```
Ser Thr Arg Val Pro Ala Ala Tyr Ala Ala Gln Gly Tyr Lys Val Leu
1               5                   10                  15

Val Leu Asn Pro Ser Val Ala Ala Thr Leu Gly Phe Gly Ala Tyr Met
            20                  25                  30

Ser Lys Ala His Gly Thr Asp Pro Asn Ile Arg Thr Gly Val
        35                  40                  45
```

<210> SEQ ID NO 42
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 42

```
Ser Thr Arg Val Pro Ala Ala Tyr Ala Ala Gln Gly Tyr Lys Val Leu
1               5                   10                  15

Val Leu Asn Pro Ser Val Ala Ala Thr Leu Ser Phe Gly Ala Tyr Met
            20                  25                  30

Ser Lys Ala Tyr Gly Val Asp Pro Asn Ile Arg Thr Gly Val
        35                  40                  45
```

<210> SEQ ID NO 43
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 43

```
Ser Thr Arg Val Pro Ala Ala Tyr Ala Ala Gln Gly Tyr Lys Val Leu
1               5                   10                  15

Val Leu Asn Pro Ser Val Ala Ala Thr Leu Gly Phe Gly Thr Tyr Met
            20                  25                  30

Ser Lys Ala Tyr Gly Thr Asp Pro Asn Ile Arg Thr Gly Val
        35                  40                  45
```

<210> SEQ ID NO 44
<211> LENGTH: 46
<212> TYPE: PRT
<213> ORGANISM: artificial sequence
<220> FEATURE:
<223> OTHER INFORMATION: anti-VHC immunogenic peptide

<400> SEQUENCE: 44

```
Ser Thr Lys Val Pro Ala Ala His Ala Ala Gln Gly Tyr Lys Val Leu
1               5                   10                  15

Val Leu Asn Pro Ser Val Ala Ala Thr Leu Gly Phe Gly Val Tyr Met
            20                  25                  30

Ser Lys Ala Tyr Gly Ile Asp Pro Asn Ile Arg Ser Gly Val
        35                  40                  45
```

<210> SEQ ID NO 45
<211> LENGTH: 45
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (2)..(2)
<223> OTHER INFORMATION: Xaa = L or V
<220> FEATURE:
<221> NAME/KEY: MISC_FEATURE
<222> LOCATION: (3)..(3)
<223> OTHER INFORMATION: Xaa = L or F
<220> FEATURE:
<221> NAME/KEY: MISC_FEATURE
<222> LOCATION: (4)..(4)
<223> OTHER INFORMATION: Xaa = G or S
<220> FEATURE:
<221> NAME/KEY: MISC_FEATURE
<222> LOCATION: (5)..(5)
<223> OTHER INFORMATION: Xaa = C or T
<220> FEATURE:
<221> NAME/KEY: MISC_FEATURE
<222> LOCATION: (6)..(6)
<223> OTHER INFORMATION: Xaa = I or V
<220> FEATURE:
<221> NAME/KEY: MISC_FEATURE
<222> LOCATION: (7)..(7)
<223> OTHER INFORMATION: Xaa = I or V
<220> FEATURE:
<221> NAME/KEY: MISC_FEATURE
<222> LOCATION: (15)..(15)
<223> OTHER INFORMATION: Xaa = K, R or T
<220> FEATURE:
<221> NAME/KEY: MISC_FEATURE
<222> LOCATION: (17)..(17)
<223> OTHER INFORMATION: Xaa = Q or E
<220> FEATURE:
<221> NAME/KEY: MISC_FEATURE
<222> LOCATION: (18)..(18)
<223> OTHER INFORMATION: Xaa = V or N
<220> FEATURE:
<221> NAME/KEY: MISC_FEATURE
<222> LOCATION: (19)..(19)
<223> OTHER INFORMATION: Xaa = D, E or C
<220> FEATURE:
<221> NAME/KEY: MISC_FEATURE
<222> LOCATION: (22)..(22)
<223> OTHER INFORMATION: Xaa = V or A
<220> FEATURE:
<221> NAME/KEY: MISC_FEATURE
<222> LOCATION: (24)..(24)
<223> OTHER INFORMATION: Xaa = V, I, E or M
<220> FEATURE:
<221> NAME/KEY: MISC_FEATURE
<222> LOCATION: (25)..(25)
<223> OTHER INFORMATION: Xaa = L or V
<220> FEATURE:
<221> NAME/KEY: MISC_FEATURE
<222> LOCATION: (29)..(29)
<223> OTHER INFORMATION: Xaa = T, K or A
<220> FEATURE:
<221> NAME/KEY: MISC_FEATURE
<222> LOCATION: (30)..(30)
<223> OTHER INFORMATION: Xaa = Q or H
<220> FEATURE:
<221> NAME/KEY: MISC_FEATURE
<222> LOCATION: (31)..(31)
<223> OTHER INFORMATION: Xaa = S or T
<220> FEATURE:
<221> NAME/KEY: MISC_FEATURE
<222> LOCATION: (34)..(34)
<223> OTHER INFORMATION: Xaa = A or G
<220> FEATURE:
<221> NAME/KEY: MISC_FEATURE
<222> LOCATION: (35)..(35)
<223> OTHER INFORMATION: Xaa = T or S
<220> FEATURE:
<221> NAME/KEY: MISC_FEATURE
<222> LOCATION: (36)..(36)
<223> OTHER INFORMATION: Xaa = C or A
<220> FEATURE:
<221> NAME/KEY: MISC_FEATURE
<222> LOCATION: (37)..(37)
<223> OTHER INFORMATION: Xaa = V, I or T
<220> FEATURE:
<221> NAME/KEY: MISC_FEATURE
<222> LOCATION: (40)..(40)
<223> OTHER INFORMATION: Xaa = V or A
<220> FEATURE:
<221> NAME/KEY: MISC_FEATURE
<222> LOCATION: (41)..(41)
<223> OTHER INFORMATION: Xaa = C or M
<220> FEATURE:
<221> NAME/KEY: MISC_FEATURE
<222> LOCATION: (45)..(45)
<223> OTHER INFORMATION: Xaa = Y or F

<400> SEQUENCE: 45

```
Gly Xaa Xaa Xaa Xaa Xaa Xaa Thr Ser Leu Thr Gly Arg Asp Xaa Asn
1               5                   10                  15

Xaa Xaa Xaa Gly Glu Xaa Gln Xaa Xaa Ser Thr Ala Xaa Xaa Xaa Phe
            20                  25                  30

Leu Xaa Xaa Xaa Xaa Asn Gly Xaa Xaa Trp Thr Val Xaa
        35                  40                  45
```

<210> SEQ ID NO 46
<211> LENGTH: 63
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (2)..(2)
<223> OTHER INFORMATION: Xaa = P, S, or H
<220> FEATURE:
<221> NAME/KEY: MISC_FEATURE
<222> LOCATION: (5)..(5)
<223> OTHER INFORMATION: Xaa = A or T
<220> FEATURE:
<221> NAME/KEY: MISC_FEATURE
<222> LOCATION: (7)..(7)
<223> OTHER INFORMATION: Xaa = S, A, T or C
<220> FEATURE:
<221> NAME/KEY: MISC_FEATURE
<222> LOCATION: (8)..(8)
<223> OTHER INFORMATION: Xaa = Q or R
<220> FEATURE:
<221> NAME/KEY: MISC_FEATURE
<222> LOCATION: (13)..(13)
<223> OTHER INFORMATION: Xaa = L or V
<220> FEATURE:
<221> NAME/KEY: MISC_FEATURE
<222> LOCATION: (14)..(14)
<223> OTHER INFORMATION: Xaa = L or F
<220> FEATURE:
<221> NAME/KEY: MISC_FEATURE
<222> LOCATION: (15)..(15)
<223> OTHER INFORMATION: Xaa = G or S
<220> FEATURE:
<221> NAME/KEY: MISC_FEATURE
<222> LOCATION: (16)..(16)
<223> OTHER INFORMATION: Xaa = C or T
<220> FEATURE:

<221> NAME/KEY: MISC_FEATURE
<222> LOCATION: (17)..(17)
<223> OTHER INFORMATION: Xaa = I or V
<220> FEATURE:
<221> NAME/KEY: MISC_FEATURE
<222> LOCATION: (18)..(18)
<223> OTHER INFORMATION: Xaa = I or V
<220> FEATURE:
<221> NAME/KEY: MISC_FEATURE
<222> LOCATION: (26)..(26)
<223> OTHER INFORMATION: Xaa = K, R or T
<220> FEATURE:
<221> NAME/KEY: MISC_FEATURE
<222> LOCATION: (28)..(28)
<223> OTHER INFORMATION: Xaa = Q or E
<220> FEATURE:
<221> NAME/KEY: MISC_FEATURE
<222> LOCATION: (29)..(29)
<223> OTHER INFORMATION: Xaa = V or N
<220> FEATURE:
<221> NAME/KEY: MISC_FEATURE
<222> LOCATION: (30)..(30)
<223> OTHER INFORMATION: Xaa = D, E or C
<220> FEATURE:
<221> NAME/KEY: MISC_FEATURE
<222> LOCATION: (33)..(33)
<223> OTHER INFORMATION: Xaa = V or A
<220> FEATURE:
<221> NAME/KEY: MISC_FEATURE
<222> LOCATION: (35)..(35)
<223> OTHER INFORMATION: Xaa = V, I, E or M
<220> FEATURE:
<221> NAME/KEY: MISC_FEATURE
<222> LOCATION: (36)..(36)
<223> OTHER INFORMATION: Xaa = L or V
<220> FEATURE:
<221> NAME/KEY: MISC_FEATURE
<222> LOCATION: (40)..(40)
<223> OTHER INFORMATION: Xaa =T, K or A
<220> FEATURE:
<221> NAME/KEY: MISC_FEATURE
<222> LOCATION: (41)..(41)
<223> OTHER INFORMATION: Xaa = Q or H
<220> FEATURE:
<221> NAME/KEY: MISC_FEATURE
<222> LOCATION: (42)..(42)
<223> OTHER INFORMATION: Xaa = S or T
<220> FEATURE:
<221> NAME/KEY: MISC_FEATURE
<222> LOCATION: (45)..(45)
<223> OTHER INFORMATION: Xaa = A or G
<220> FEATURE:
<221> NAME/KEY: MISC_FEATURE
<222> LOCATION: (46)..(46)
<223> OTHER INFORMATION: Xaa = T or S
<220> FEATURE:
<221> NAME/KEY: MISC_FEATURE
<222> LOCATION: (47)..(47)
<223> OTHER INFORMATION: Xaa = C or A
<220> FEATURE:
<221> NAME/KEY: MISC_FEATURE
<222> LOCATION: (48)..(48)
<223> OTHER INFORMATION: Xaa = V, I or T
<220> FEATURE:
<221> NAME/KEY: MISC_FEATURE
<222> LOCATION: (51)..(51)
<223> OTHER INFORMATION: Xaa = V or A
<220> FEATURE:
<221> NAME/KEY: MISC_FEATURE
<222> LOCATION: (52)..(52)
<223> OTHER INFORMATION: Xaa = C or M
<220> FEATURE:
<221> NAME/KEY: MISC_FEATURE
<222> LOCATION: (56)..(56)
<223> OTHER INFORMATION: Xaa = Y or F
<220> FEATURE:
<221> NAME/KEY: MISC_FEATURE
<222> LOCATION: (61)..(61)
<223> OTHER INFORMATION: Xaa = S, T or A
<220> FEATURE:

```
<221> NAME/KEY: MISC_FEATURE
<222> LOCATION: (62)..(62)
<223> OTHER INFORMATION: Xaa = K or R
<220> FEATURE:
<221> NAME/KEY: MISC_FEATURE
<222> LOCATION: (63)..(63)
<223> OTHER INFORMATION: Xaa = T or I

<400> SEQUENCE: 46

Ala Xaa Ile Thr Xaa Tyr Xaa Xaa Gln Thr Arg Gly Xaa Xaa Xaa Xaa
1               5                   10                  15

Xaa Xaa Thr Ser Leu Thr Gly Arg Asp Xaa Asn Xaa Xaa Xaa Gly Glu
            20                  25                  30

Xaa Gln Xaa Xaa Ser Thr Ala Xaa Xaa Xaa Phe Leu Xaa Xaa Xaa Xaa
        35                  40                  45

Asn Gly Xaa Xaa Trp Thr Val Xaa His Gly Ala Gly Xaa Xaa Xaa
    50                  55                  60


<210> SEQ ID NO 47
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 47

Gly Leu Leu Gly Cys Ile Ile Thr Ser Leu Thr Gly Arg Asp Lys Asn
1               5                   10                  15

Gln Val Asp Gly Glu Val Gln Val Leu Ser Thr Ala Thr Gln Ser Phe
            20                  25                  30

Leu Ala Thr Cys Val Asn Gly Val Cys Trp Thr Val Tyr
        35                  40                  45


<210> SEQ ID NO 48
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 48

Gly Leu Leu Gly Cys Ile Ile Thr Ser Leu Thr Gly Arg Asp Lys Asn
1               5                   10                  15

Gln Val Glu Gly Glu Val Gln Ile Val Ser Thr Ala Ala Gln Thr Phe
            20                  25                  30

Leu Ala Thr Cys Ile Asn Gly Val Cys Trp Thr Val Tyr
        35                  40                  45


<210> SEQ ID NO 49
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 49

Gly Leu Leu Gly Cys Ile Ile Thr Ser Leu Thr Gly Arg Asp Lys Asn
1               5                   10                  15

Gln Val Glu Gly Glu Val Gln Ile Val Ser Thr Ala Thr Gln Thr Phe
            20                  25                  30

Leu Ala Thr Cys Ile Asn Gly Val Cys Trp Thr Val Tyr
        35                  40                  45
```

<210> SEQ ID NO 50
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 50

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Val Asn Gly Val Cys Trp Thr Val Tyr
35 40 45

<210> SEQ ID NO 51
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 51

Gly Leu Leu Gly Cys Ile Ile Thr Ser Leu Thr Gly Arg Asp Arg Asn
1 5 10 15

Gln Val Glu Gly Glu Val Gln Val Val Ser Thr Ala Thr Gln Ser Phe
20 25 30

Leu Ala Thr Cys Val Asn Gly Val Cys Trp Thr Val Tyr
35 40 45

<210> SEQ ID NO 52
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 52

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Ile Asn Gly Val Cys Trp Thr Val Tyr
35 40 45

<210> SEQ ID NO 53
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 53

Gly Leu Phe Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Val Asn Gly Val Cys Trp Thr Val Tyr
35 40 45

<210> SEQ ID NO 54
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 54

Gly Val Leu Gly Cys Val Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Ile Asn Gly Val Cys Trp Thr Val Tyr
35 40 45

<210> SEQ ID NO 55
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 55

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Val Asn Gly Ala Cys Trp Thr Val Phe
35 40 45

<210> SEQ ID NO 56
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 56

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Ile Asn Gly Val Cys Trp Thr Val Phe
35 40 45

<210> SEQ ID NO 57
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 57

Gly Val Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Ile Asn Gly Val Cys Trp Thr Val Tyr
35 40 45

<210> SEQ ID NO 58
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 58

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Phe
        35                  40                  45

<210> SEQ ID NO 59
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 59

Gly Leu Leu Gly Cys Ile Val Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Ala Cys Trp Thr Val Phe
        35                  40                  45

<210> SEQ ID NO 60
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 60

Gly Val Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Phe
        35                  40                  45

<210> SEQ ID NO 61
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 61

Gly Leu Leu Gly Cys Ile Ile Thr Ser Leu Thr Gly Arg Asp Lys Asn
1               5                   10                  15

Gln Val Asp Gly Glu Val Gln Val Leu Ser Thr Ala Thr Gln Ser Phe
            20                  25                  30

Leu Ala Thr Cys Ile Asn Gly Val Cys Trp Thr Val Tyr
        35                  40                  45

<210> SEQ ID NO 62
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 62

Gly Leu Leu Gly Cys Ile Ile Thr Ser Leu Thr Gly Arg Asp Lys Asn
1               5                   10                  15

```
Gln Val Glu Gly Glu Val Gln Val Val Ser Thr Ala Thr Gln Ser Phe
            20                  25                  30

Leu Ala Thr Cys Val Asn Gly Ala Cys Trp Thr Val Tyr
        35                  40                  45


<210> SEQ ID NO 63
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 63

Gly Val Leu Gly Cys Ile Ile Thr Ser Leu Thr Gly Arg Asp Lys Asn
1               5                   10                  15

Gln Val Glu Gly Glu Val Gln Val Val Ser Thr Ala Thr His Ser Phe
            20                  25                  30

Leu Ala Thr Cys Ile Asn Gly Val Cys Trp Thr Val Tyr
        35                  40                  45


<210> SEQ ID NO 64
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 64

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Ala Cys Trp Thr Val Tyr
        35                  40                  45


<210> SEQ ID NO 65
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 65

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Ser Cys Val Asn Gly Val Cys Trp Thr Val Tyr
        35                  40                  45


<210> SEQ ID NO 66
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 66

Gly Leu Leu Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Thr Asn Gly Val Cys Trp Thr Val Tyr
```

35 40 45

<210> SEQ ID NO 67
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 67

Gly Val Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Val Asn Gly Val Cys Trp Thr Val Tyr
35 40 45

<210> SEQ ID NO 68
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 68

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Lys Gln Ser Phe
20 25 30

Leu Ala Thr Cys Val Asn Gly Val Cys Trp Thr Val Tyr
35 40 45

<210> SEQ ID NO 69
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 69

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Lys Gln Ser Phe
20 25 30

Leu Ala Thr Cys Val Asn Gly Ala Cys Trp Thr Val Tyr
35 40 45

<210> SEQ ID NO 70
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 70

Gly Leu Leu Gly Cys Ile Ile Thr Ser Leu Thr Gly Arg Asp Lys Asn
1 5 10 15

Gln Val Glu Gly Glu Val Gln Val Val Ser Thr Ala Thr Gln Thr Phe
20 25 30

Leu Ala Thr Cys Val Asn Gly Val Cys Trp Thr Val Phe
35 40 45

<210> SEQ ID NO 71

<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 71

Gly Leu Leu Gly Cys Ile Ile Thr Ser Leu Thr Gly Arg Asp Lys Asn
1 5 10 15

Gln Val Glu Gly Glu Val Gln Glu Val Ser Thr Ala Thr Gln Ser Phe
20 25 30

Leu Ala Thr Cys Val Asn Gly Val Cys Trp Thr Val Tyr
35 40 45

<210> SEQ ID NO 72
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 72

Gly Leu Phe Gly Cys Ile Val Thr Ser Leu Thr Gly Arg Asp Lys Asn
1 5 10 15

Gln Val Glu Gly Glu Ala Gln Val Val Ser Thr Ala Thr Gln Ser Phe
20 25 30

Leu Ala Thr Cys Val Asn Gly Val Cys Trp Thr Val Tyr
35 40 45

<210> SEQ ID NO 73
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 73

Gly Leu Phe Gly Cys Ile Ile Thr Ser Leu Thr Gly Arg Asp Lys Asn
1 5 10 15

Gln Val Glu Gly Glu Val Gln Val Val Ser Thr Ala Thr Gln Ser Phe
20 25 30

Leu Ala Thr Cys Ile Asn Gly Val Cys Trp Thr Val Tyr
35 40 45

<210> SEQ ID NO 74
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 74

Gly Leu Phe Gly Cys Ile Val Thr Ser Leu Thr Gly Arg Asp Lys Asn
1 5 10 15

Gln Val Glu Gly Glu Ala Gln Val Val Ser Thr Ala Thr Gln Ser Phe
20 25 30

Leu Ala Thr Cys Val Asn Gly Ala Cys Trp Thr Val Tyr
35 40 45

<210> SEQ ID NO 75
<211> LENGTH: 45
<212> TYPE: PRT
<213> ORGANISM: artificial sequence
<220> FEATURE:

<223> OTHER INFORMATION: anti-VHC immunogenic peptide

<400> SEQUENCE: 75

```
Gly Leu Leu Gly Cys Ile Val Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Val Asn Gly Val Cys Trp Thr Val Phe
        35                  40                  45
```

<210> SEQ ID NO 76
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 76

```
Gly Leu Phe Gly Cys Ile Ile Thr Ser Leu Thr Gly Arg Asp Arg Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Tyr
        35                  40                  45
```

<210> SEQ ID NO 77
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 77

```
Gly Leu Phe Gly Cys Ile Ile Thr Ser Leu Thr Gly Arg Asp Lys Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Tyr
        35                  40                  45
```

<210> SEQ ID NO 78
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 78

```
Gly Leu Leu Gly Cys Ile Ile Thr Ser Leu Thr Gly Arg Asp Arg Asn
1               5                   10                  15

Gln Val Glu Gly Glu Val Gln Val Val Ser Thr Ala Thr Gln Ser Phe
            20                  25                  30

Leu Ala Thr Cys Ile Asn Gly Val Cys Trp Thr Val Phe
        35                  40                  45
```

<210> SEQ ID NO 79
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 79

```
Gly Leu Leu Gly Cys Ile Ile Thr Ser Leu Thr Gly Arg Asp Arg Asn
1               5                   10                  15

Gln Val Glu Gly Glu Val Gln Met Val Ser Thr Ala Thr Gln Ser Phe
            20                  25                  30

Leu Ala Thr Cys Val Asn Gly Val Cys Trp Thr Val Tyr
        35                  40                  45


<210> SEQ ID NO 80
<211> LENGTH: 45
<212> TYPE: PRT
<213> ORGANISM: artificial sequence
<220> FEATURE:
<223> OTHER INFORMATION: anti-VHC immunogenic peptide

<400> SEQUENCE: 80

Gly Leu Phe Ser Thr Ile Ile Thr Ser Leu Thr Gly Arg Asp Thr Asn
1               5                   10                  15

Glu Asn Cys Gly Glu Val Gln Val Leu Ser Thr Ala Thr Gln Ser Phe
            20                  25                  30

Leu Gly Thr Ala Val Asn Gly Val Met Trp Thr Val Tyr
        35                  40                  45


<210> SEQ ID NO 81
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 81

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60


<210> SEQ ID NO 82
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 82

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Ala Gln Thr Phe Leu Ala Thr Cys Ile
        35                  40                  45

Asn Gly Val Cys Trp Thr Val Tyr His Gly Ala Gly Thr Arg Thr
    50                  55                  60


<210> SEQ ID NO 83
<211> LENGTH: 63
<212> TYPE: PRT
<213> ORGANISM: artificial sequence
<220> FEATURE:
<223> OTHER INFORMATION: anti-VHC immunogenic peptide
```

<400> SEQUENCE: 83

Ala Pro Ile Thr Ala Tyr Thr Gln Gln Thr Arg Gly Leu Leu Gly Cys
1 5 10 15

Ile Ile Thr Ser Leu Thr Gly Arg Asp Lys Asn Gln Val Glu Gly Glu
20 25 30

Val Gln Ile Val Ser Thr Ala Thr Gln Thr Phe Leu Ala Thr Cys Ile
35 40 45

Asn Gly Val Cys Trp Thr Val Tyr His Gly Ala Gly Thr Arg Thr
50 55 60

<210> SEQ ID NO 84
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 84

Ala Pro Ile Thr Ala Tyr Ser Gln Gln Thr Arg Gly Leu Leu Gly Cys
1 5 10 15

Ile Ile Thr Ser Leu Thr Gly Arg Asp Lys Asn Gln Val Glu Gly Glu
20 25 30

Val Gln Val Val Ser Thr Ala Thr Gln Ser Phe Leu Ala Thr Cys Val
35 40 45

Asn Gly Val Cys Trp Thr Val Tyr His Gly Ala Gly Ser Lys Thr
50 55 60

<210> SEQ ID NO 85
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 85

Ala Pro Ile Thr Ala Tyr Ser Gln Gln Thr Arg Gly Leu Leu Gly Cys
1 5 10 15

Ile Ile Thr Ser Leu Thr Gly Arg Asp Arg Asn Gln Val Glu Gly Glu
20 25 30

Val Gln Val Val Ser Thr Ala Thr Gln Ser Phe Leu Ala Thr Cys Val
35 40 45

Asn Gly Val Cys Trp Thr Val Tyr His Gly Ala Gly Ser Lys Thr
50 55 60

<210> SEQ ID NO 86
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 86

Ala Pro Ile Thr Ala Tyr Ser Gln Gln Thr Arg Gly Leu Leu Gly Cys
1 5 10 15

Ile Ile Thr Ser Leu Thr Gly Arg Asp Lys Asn Gln Val Glu Gly Glu
20 25 30

Val Gln Val Val Ser Thr Ala Thr Gln Ser Phe Leu Ala Thr Cys Ile
35 40 45

Asn Gly Val Cys Trp Thr Val Tyr His Gly Ala Gly Ser Lys Thr
50 55 60

<210> SEQ ID NO 87
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 87

```
Ala Pro Ile Thr Ala Tyr Ser Gln Gln Thr Arg Gly Leu Phe Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60
```

<210> SEQ ID NO 88
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 88

```
Ala Pro Ile Thr Ala Tyr Ser Gln Gln Thr Arg Gly Val Leu Gly Cys
1               5                   10                  15

Val Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60
```

<210> SEQ ID NO 89
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 89

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Phe His Gly Ala Gly Ser Lys Thr
    50                  55                  60
```

<210> SEQ ID NO 90
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 90

```
Ala Pro Ile Thr Ala Tyr Ser Arg Gln Thr Arg Gly Leu Leu Gly Cys
1               5                   10                  15

Ile Ile Thr Ser Leu Thr Gly Arg Asp Lys Asn Gln Val Glu Gly Glu
```

-continued

```
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60


<210> SEQ ID NO 91
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 91

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Phe His Gly Ala Gly Ala Lys Thr
    50                  55                  60


<210> SEQ ID NO 92
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 92

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Phe His Gly Ala Gly Ser Lys Thr
    50                  55                  60


<210> SEQ ID NO 93
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 93

Ala Pro Ile Thr Ala Tyr Ser Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60


<210> SEQ ID NO 94
<211> LENGTH: 63
<212> TYPE: PRT
<213> ORGANISM: artificial sequence
<220> FEATURE:
```

<223> OTHER INFORMATION: anti-VHC immunogenic peptide

<400> SEQUENCE: 94

```
Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60
```

<210> SEQ ID NO 95
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 95

```
Ala Pro Ile Thr Ala Tyr Ser Gln Gln Thr Arg Gly Leu Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Phe His Gly Ala Gly Ser Lys Thr
    50                  55                  60
```

<210> SEQ ID NO 96
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 96

```
Ala Pro Ile Thr Ala Tyr Ala Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60
```

<210> SEQ ID NO 97
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 97

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Asp Gly Glu
            20                  25                  30

Val Gln Val Leu Ser Thr Ala Thr Gln Ser Phe Leu Ala Thr Cys Ile
        35                  40                  45

Asn Gly Val Cys Trp Thr Val Tyr His Gly Ala Gly Ser Lys Thr
```

50 55 60

<210> SEQ ID NO 98
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 98

Ala Pro Ile Thr Ala Tyr Ser Gln Gln Thr Arg Gly Leu Leu Gly Cys
1 5 10 15

Ile Ile Thr Ser Leu Thr Gly Arg Asp Lys Asn Gln Val Glu Gly Glu
20 25 30

Val Gln Val Val Ser Thr Ala Thr Gln Ser Phe Leu Ala Thr Cys Val
35 40 45

Asn Gly Ala Cys Trp Thr Val Tyr His Gly Ala Gly Ser Lys Thr
50 55 60

<210> SEQ ID NO 99
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 99

Ala Pro Ile Thr Ala Tyr Ser Gln Gln Thr Arg Gly Val Leu Gly Cys
1 5 10 15

Ile Ile Thr Ser Leu Thr Gly Arg Asp Lys Asn Gln Val Glu Gly Glu
20 25 30

Val Gln Val Val Ser Thr Ala Thr His Ser Phe Leu Ala Thr Cys Ile
35 40 45

Asn Gly Val Cys Trp Thr Val Tyr His Gly Ala Gly Ser Lys Thr
50 55 60

<210> SEQ ID NO 100
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 100

Ala Pro Ile Thr Ala Tyr Ser Gln Gln Thr Arg Gly Leu Leu Gly Cys
1 5 10 15

Ile Ile Thr Ser Leu Thr Gly Arg Asp Lys Asn Gln Val Glu Gly Glu
20 25 30

Val Gln Val Val Ser Thr Ala Thr Gln Ser Phe Leu Ala Thr Cys Ile
35 40 45

Asn Gly Ala Cys Trp Thr Val Tyr His Gly Ala Gly Ser Lys Thr
50 55 60

<210> SEQ ID NO 101
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 101

Ala Pro Ile Thr Ala Tyr Ser Gln Gln Thr Arg Gly Leu Leu Gly Cys
1 5 10 15

```
Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Ser Cys Val
        35                  40                  45

Asn Gly Val Cys Trp Thr Val Tyr His Gly Ala Gly Ser Lys Thr
    50                  55                  60


<210> SEQ ID NO 102
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 102

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Thr
        35                  40                  45

Asn Gly Val Cys Trp Thr Val Tyr His Gly Ala Gly Ser Lys Thr
    50                  55                  60


<210> SEQ ID NO 103
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 103

Ala Pro Ile Thr Ala Tyr Ser Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60


<210> SEQ ID NO 104
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 104

Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Lys Ser Phe Leu Ala Thr Cys Val
        35                  40                  45

Asn Gly Val Cys Trp Thr Val Tyr His Gly Ala Gly Ser Lys Thr
    50                  55                  60


<210> SEQ ID NO 105
<211> LENGTH: 63
<212> TYPE: PRT
```

<213> ORGANISM: artificial sequence
<220> FEATURE:
<223> OTHER INFORMATION: anti-VHC immunogenic peptide

<400> SEQUENCE: 105

```
Ala Pro Ile Thr Ala Tyr Cys Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60
```

<210> SEQ ID NO 106
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 106

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Lys Gln Ser Phe Leu Ala Thr Cys Val
        35                  40                  45

Asn Gly Ala Cys Trp Thr Val Tyr His Gly Ala Gly Ser Lys Thr
    50                  55                  60
```

<210> SEQ ID NO 107
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 107

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Thr Lys Thr
    50                  55                  60
```

<210> SEQ ID NO 108
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 108

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Thr Phe Leu Ala Thr Cys Val
        35                  40                  45
```

```
Asn Gly Val Cys Trp Thr Val Phe His Gly Ala Gly Ser Lys Thr
    50                  55                  60
```

<210> SEQ ID NO 109
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 109

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Ala Cys Trp Thr Val Tyr His Gly Ala Gly Thr Lys Thr
    50                  55                  60
```

<210> SEQ ID NO 110
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 110

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Thr Lys Thr
    50                  55                  60
```

<210> SEQ ID NO 111
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 111

```
Ala Pro Ile Thr Ala Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Glu Val Ser Thr Ala Thr Gln Ser Phe Leu Ala Thr Cys Val
        35                  40                  45

Asn Gly Val Cys Trp Thr Val Tyr His Gly Ala Gly Ser Lys Ile
    50                  55                  60
```

<210> SEQ ID NO 112
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 112

```
Ala Pro Ile Thr Ala Tyr Ser Gln Gln Thr Arg Gly Leu Phe Gly Cys
1               5                   10                  15

Ile Val Thr Ser Leu Thr Gly Arg Asp Lys Asn Gln Val Glu Gly Glu
            20                  25                  30

Ala Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr
    50                  55                  60


<210> SEQ ID NO 113
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 113

Ala Pro Ile Thr Ala Tyr Ser Gln Gln Thr Arg Gly Leu Phe Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60


<210> SEQ ID NO 114
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 114

Ala Pro Ile Thr Ala Tyr Ser Gln Gln Thr Arg Gly Leu Ala Gly Cys
1               5                   10                  15

Ile Val Thr Ser Leu Thr Gly Arg Asp Lys Asn Gln Val Glu Gly Glu
            20                  25                  30

Ala Gln Val Val Ser Thr Ala Thr Gln Ser Phe Leu Ala Thr Cys Val
        35                  40                  45

Asn Gly Ala Cys Trp Thr Val Tyr His Gly Ala Gly Ser Lys Thr
    50                  55                  60


<210> SEQ ID NO 115
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 115

Ala Pro Ile Thr Ala Tyr Ser Gln Gln Thr Arg Gly Val Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60


<210> SEQ ID NO 116
```

<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 116

```
Ala Pro Ile Thr Thr Tyr Ser Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Thr Lys Thr
    50                  55                  60
```

<210> SEQ ID NO 117
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 117

```
Ala Ser Ile Thr Ala Tyr Ser Gln Gln Thr Arg Gly Val Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60
```

<210> SEQ ID NO 118
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 118

```
Ala Ser Ile Thr Ala Tyr Ser Gln Gln Thr Arg Gly Leu Leu Gly Cys
1               5                   10                  15

Ile Val Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60
```

<210> SEQ ID NO 119
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 119

```
Ala Pro Ile Thr Ala Tyr Ala Gln Gln Thr Arg Gly Leu Leu Gly Cys
1               5                   10                  15

Ile Val Thr Ser Leu Thr Gly Arg Asp Lys Asn Gln Val Glu Gly Glu
            20                  25                  30
```

```
Val Gln Val Val Ser Thr Ala Thr Gln Ser Phe Leu Ala Thr Cys Val
        35                  40                  45

Asn Gly Val Cys Trp Thr Val Phe His Gly Ala Gly Ser Lys Thr
    50                  55                  60


<210> SEQ ID NO 120
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 120

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60


<210> SEQ ID NO 121
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 121

Ala Pro Ile Thr Ala Tyr Ala Gln Gln Thr Arg Gly Leu Phe Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60


<210> SEQ ID NO 122
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 122

Ala Pro Ile Thr Ala Tyr Ala Gln Gln Thr Arg Gly Leu Phe Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr
    50                  55                  60


<210> SEQ ID NO 123
<211> LENGTH: 63
<212> TYPE: PRT
<213> ORGANISM: artificial sequence
<220> FEATURE:
<223> OTHER INFORMATION: anti-VHC immunogenic peptide
```

<400> SEQUENCE: 123

Ala Pro Ile Thr Ala Tyr Ser Gln Gln Thr Arg Gly Leu Leu Gly Cys
1 5 10 15

Ile Ile Thr Ser Leu Thr Gly Arg Asp Arg Asn Gln Val Glu Gly Glu
20 25 30

Val Gln Val Val Ser Thr Ala Thr Gln Ser Phe Leu Ala Thr Cys Ile
35 40 45

Asn Gly Val Cys Trp Thr Val Phe His Gly Ala Gly Ser Lys Thr
50 55 60

<210> SEQ ID NO 124
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 124

Ala Pro Ile Thr Ala Tyr Ser Gln Gln Thr Arg Gly Leu Leu Gly Cys
1 5 10 15

Ile Ile Thr Ser Leu Thr Gly Arg Asp Arg Asn Gln Val Glu Gly Glu
20 25 30

Val Gln Val Val Ser Thr Ala Thr Gln Ser Phe Leu Ala Thr Cys Val
35 40 45

Asn Gly Val Cys Trp Thr Val Tyr His Gly Ala Gly Ala Lys Thr
50 55 60

<210> SEQ ID NO 125
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 125

Ala His Ile Thr Ala Tyr Ser Gln Gln Thr Arg Gly Leu Leu Gly Cys
1 5 10 15

Ile Ile Thr Ser Leu Thr Gly Arg Asp Arg Asn Gln Val Glu Gly Glu
20 25 30

Val Gln Met Val Ser Thr Ala Thr Gln Ser Phe Leu Ala Thr Cys Val
35 40 45

Asn Gly Val Cys Trp Thr Val Tyr His Gly Ala Gly Ser Lys Thr
50 55 60

<210> SEQ ID NO 126
<211> LENGTH: 63
<212> TYPE: PRT
<213> ORGANISM: artificial sequence
<220> FEATURE:
<223> OTHER INFORMATION: anti-VHC immunogenic peptide

<400> SEQUENCE: 126

Ala Pro Ile Thr Ala Tyr Ser Gln Gln Thr Arg Gly Leu Phe Ser Thr
1 5 10 15

Ile Ile Thr Ser Leu Thr Gly Arg Asp Thr Asn Glu Asn Cys Gly Glu
20 25 30

Val Gln Val Leu Ser Thr Ala Thr Gln Ser Phe Leu Gly Thr Cys Val
35 40 45

Asn Gly Val Met Trp Thr Val Tyr His Gly Ala Gly Ala Lys Thr
50 55 60

<210> SEQ ID NO 127
<211> LENGTH: 32
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (2)..(2)
<223> OTHER INFORMATION: Xaa = L or P
<220> FEATURE:
<221> NAME/KEY: MISC_FEATURE
<222> LOCATION: (4)..(4)
<223> OTHER INFORMATION: Xaa = A or S
<220> FEATURE:
<221> NAME/KEY: MISC_FEATURE
<222> LOCATION: (7)..(7)
<223> OTHER INFORMATION: Xaa = A or S
<220> FEATURE:
<221> NAME/KEY: MISC_FEATURE
<222> LOCATION: (8)..(8)
<223> OTHER INFORMATION: Xaa = A or S
<220> FEATURE:
<221> NAME/KEY: MISC_FEATURE
<222> LOCATION: (9)..(9)
<223> OTHER INFORMATION: Xaa = I or V
<220> FEATURE:
<221> NAME/KEY: MISC_FEATURE
<222> LOCATION: (14)..(14)
<223> OTHER INFORMATION: Xaa = T, S or A
<220> FEATURE:
<221> NAME/KEY: MISC_FEATURE
<222> LOCATION: (15)..(15)
<223> OTHER INFORMATION: Xaa = T or I
<220> FEATURE:
<221> NAME/KEY: MISC_FEATURE
<222> LOCATION: (16)..(16)
<223> OTHER INFORMATION: Xaa = Q, S or G
<220> FEATURE:
<221> NAME/KEY: MISC_FEATURE
<222> LOCATION: (17)..(17)
<223> OTHER INFORMATION: Xaa = N, Q, H, S, Y or T
<220> FEATURE:
<221> NAME/KEY: MISC_FEATURE
<222> LOCATION: (20)..(20)
<223> OTHER INFORMATION: Xaa = L or M
<220> FEATURE:
<221> NAME/KEY: MISC_FEATURE
<222> LOCATION: (24)..(24)
<223> OTHER INFORMATION: Xaa = L or W
<220> FEATURE:
<221> NAME/KEY: MISC_FEATURE
<222> LOCATION: (30)..(30)
<223> OTHER INFORMATION: Xaa = A or S
<220> FEATURE:
<221> NAME/KEY: MISC_FEATURE
<222> LOCATION: (32)..(32)
<223> OTHER INFORMATION: Xaa = L, P or I

<400> SEQUENCE: 127

```
Ser Xaa Met Xaa Phe Thr Xaa Xaa Xaa Thr Ser Pro Leu Xaa Xaa Xaa
1               5                   10                  15

Xaa Thr Leu Xaa Phe Asn Ile Xaa Gly Gly Trp Val Ala Xaa Gln Xaa
            20                  25                  30
```

<210> SEQ ID NO 128
<211> LENGTH: 57
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (4)..(4)
<223> OTHER INFORMATION: Xaa = T or S
<220> FEATURE:

<221> NAME/KEY: MISC_FEATURE
<222> LOCATION: (6)..(6)
<223> OTHER INFORMATION: Xaa = I, T or V
<220> FEATURE:
<221> NAME/KEY: MISC_FEATURE
<222> LOCATION: (11)..(11)
<223> OTHER INFORMATION: Xaa =G or A
<220> FEATURE:
<221> NAME/KEY: MISC_FEATURE
<222> LOCATION: (19)..(19)
<223> OTHER INFORMATION: Xaa = P or L
<220> FEATURE:
<221> NAME/KEY: MISC_FEATURE
<222> LOCATION: (21)..(21)
<223> OTHER INFORMATION: Xaa = I or M
<220> FEATURE:
<221> NAME/KEY: MISC_FEATURE
<222> LOCATION: (22)..(22)
<223> OTHER INFORMATION: Xaa = A, V or R
<220> FEATURE:
<221> NAME/KEY: MISC_FEATURE
<222> LOCATION: (24)..(24)
<223> OTHER INFORMATION: Xaa = L or P
<220> FEATURE:
<221> NAME/KEY: MISC_FEATURE
<222> LOCATION: (26)..(26)
<223> OTHER INFORMATION: Xaa = A or S
<220> FEATURE:
<221> NAME/KEY: MISC_FEATURE
<222> LOCATION: (29)..(29)
<223> OTHER INFORMATION: Xaa = A or S
<220> FEATURE:
<221> NAME/KEY: MISC_FEATURE
<222> LOCATION: (30)..(30)
<223> OTHER INFORMATION: Xaa = A or S
<220> FEATURE:
<221> NAME/KEY: MISC_FEATURE
<222> LOCATION: (31)..(31)
<223> OTHER INFORMATION: Xaa = I or V
<220> FEATURE:
<221> NAME/KEY: MISC_FEATURE
<222> LOCATION: (36)..(36)
<223> OTHER INFORMATION: Xaa = T, S or A
<220> FEATURE:
<221> NAME/KEY: MISC_FEATURE
<222> LOCATION: (37)..(37)
<223> OTHER INFORMATION: Xaa = T or I
<220> FEATURE:
<221> NAME/KEY: MISC_FEATURE
<222> LOCATION: (38)..(38)
<223> OTHER INFORMATION: Xaa = Q, S or G
<220> FEATURE:
<221> NAME/KEY: MISC_FEATURE
<222> LOCATION: (39)..(39)
<223> OTHER INFORMATION: Xaa = N, Q, H, S, Y or T
<220> FEATURE:
<221> NAME/KEY: MISC_FEATURE
<222> LOCATION: (42)..(42)
<223> OTHER INFORMATION: Xaa = L or M
<220> FEATURE:
<221> NAME/KEY: MISC_FEATURE
<222> LOCATION: (46)..(46)
<223> OTHER INFORMATION: Xaa = L or W
<220> FEATURE:
<221> NAME/KEY: MISC_FEATURE
<222> LOCATION: (52)..(52)
<223> OTHER INFORMATION: Xaa = A or S
<220> FEATURE:
<221> NAME/KEY: MISC_FEATURE
<222> LOCATION: (54)..(54)
<223> OTHER INFORMATION: Xaa = L, P or I
<220> FEATURE:
<221> NAME/KEY: MISC_FEATURE
<222> LOCATION: (55)..(55)
<223> OTHER INFORMATION: Xaa = A or R
<220> FEATURE:
<221> NAME/KEY: MISC_FEATURE
<222> LOCATION: (56)..(56)
<223> OTHER INFORMATION: Xaa = P, A or D
<220> FEATURE:

<221> NAME/KEY: MISC_FEATURE
<222> LOCATION: (57)..(57)
<223> OTHER INFORMATION: Xaa = P, A or S

<400> SEQUENCE: 128

```
Asn Phe Ile Xaa Gly Xaa Gln Tyr Leu Ala Xaa Leu Ser Thr Leu Pro
1               5                   10                  15

Gly Asn Xaa Ala Xaa Xaa Ser Xaa Met Xaa Phe Thr Xaa Xaa Xaa Thr
            20                  25                  30

Ser Pro Leu Xaa Xaa Xaa Xaa Thr Leu Xaa Phe Asn Ile Xaa Gly Gly
        35                  40                  45

Trp Val Ala Xaa Gln Xaa Xaa Xaa Xaa
    50                  55
```

<210> SEQ ID NO 129
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 129

```
Ser Leu Met Ala Phe Thr Ala Ser Ile Thr Ser Pro Leu Thr Thr Gln
1               5                   10                  15

Asn Thr Leu Leu Phe Asn Ile Leu Gly Gly Trp Val Ala Ala Gln Leu
            20                  25                  30
```

<210> SEQ ID NO 130
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 130

```
Ser Leu Met Ala Phe Thr Ala Ala Val Thr Ser Pro Leu Thr Thr Ser
1               5                   10                  15

Gln Thr Leu Leu Phe Asn Ile Leu Gly Gly Trp Val Ala Ala Gln Leu
            20                  25                  30
```

<210> SEQ ID NO 131
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 131

```
Ser Leu Met Ala Phe Thr Ala Ala Val Thr Ser Pro Leu Thr Thr Gly
1               5                   10                  15

Gln Thr Leu Leu Phe Asn Ile Leu Gly Gly Trp Val Ala Ala Gln Leu
            20                  25                  30
```

<210> SEQ ID NO 132
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 132

```
Ser Leu Met Ala Phe Thr Ala Ser Ile Thr Ser Pro Leu Thr Thr Gln
1               5                   10                  15

His Thr Leu Leu Phe Asn Ile Leu Gly Gly Trp Val Ala Ala Gln Leu
```

20 25 30

<210> SEQ ID NO 133
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 133

Ser Leu Met Ala Phe Thr Ala Ser Ile Thr Ser Pro Leu Thr Thr Gln
1 5 10 15

Ser Thr Leu Leu Phe Asn Ile Leu Gly Gly Trp Val Ala Ala Gln Leu
20 25 30

<210> SEQ ID NO 134
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 134

Ser Leu Met Ala Phe Thr Ala Ser Ile Thr Ser Pro Leu Thr Thr Gln
1 5 10 15

Tyr Thr Leu Leu Phe Asn Ile Leu Gly Gly Trp Val Ala Ala Gln Leu
20 25 30

<210> SEQ ID NO 135
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 135

Ser Leu Met Ala Phe Thr Ala Ser Val Thr Ser Pro Leu Thr Thr Gln
1 5 10 15

Asn Thr Leu Leu Phe Asn Ile Leu Gly Gly Trp Val Ala Ala Gln Leu
20 25 30

<210> SEQ ID NO 136
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 136

Ser Leu Met Ala Phe Thr Ala Ser Val Thr Ser Pro Leu Thr Thr Gln
1 5 10 15

Ser Thr Leu Leu Phe Asn Ile Leu Gly Gly Trp Val Ala Ala Gln Leu
20 25 30

<210> SEQ ID NO 137
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 137

Ser Leu Met Ala Phe Thr Ala Ser Ile Thr Ser Pro Leu Thr Thr Gln
1 5 10 15

Thr Thr Leu Met Phe Asn Ile Leu Gly Gly Trp Val Ala Ala Gln Leu 20 25 30

<210> SEQ ID NO 138
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 138

Ser Leu Met Ala Phe Thr Ala Ser Val Thr Ser Pro Leu Thr Thr Gln
1 5 10 15

Tyr Thr Leu Leu Phe Asn Ile Leu Gly Gly Trp Val Ala Ala Gln Ile
20 25 30

<210> SEQ ID NO 139
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 139

Ser Pro Met Ala Phe Thr Ala Ser Ile Thr Ser Pro Leu Thr Thr Gln
1 5 10 15

His Thr Leu Leu Phe Asn Ile Leu Gly Gly Trp Val Ala Ala Gln Leu
20 25 30

<210> SEQ ID NO 140
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 140

Ser Leu Met Ala Phe Thr Ala Ser Ile Thr Ser Pro Leu Thr Ile Gln
1 5 10 15

His Thr Leu Leu Phe Asn Ile Leu Gly Gly Trp Val Ala Ala Gln Pro
20 25 30

<210> SEQ ID NO 141
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 141

Ser Leu Met Ala Phe Thr Ser Ser Ile Thr Ser Pro Leu Thr Thr Gln
1 5 10 15

Ser Thr Leu Leu Phe Asn Ile Leu Gly Gly Trp Val Ala Ala Gln Leu
20 25 30

<210> SEQ ID NO 142
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 142

Ser Leu Met Ala Phe Thr Ala Ser Ile Thr Ser Pro Leu Ser Thr Gln
1 5 10 15

Asn Thr Leu Leu Phe Asn Ile Trp Gly Gly Trp Val Ala Ala Gln Leu

```
            20                  25                  30


<210> SEQ ID NO 143
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 143

Ser Leu Met Ala Phe Thr Ala Ser Ile Thr Ser Pro Leu Thr Thr Gln
1               5                   10                  15

Asn Thr Leu Met Phe Asn Ile Leu Gly Gly Trp Val Ala Ala Gln Leu
            20                  25                  30


<210> SEQ ID NO 144
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 144

Ser Leu Met Ala Phe Thr Ala Ser Ile Thr Ser Pro Leu Thr Thr Gln
1               5                   10                  15

His Thr Leu Met Phe Asn Ile Leu Gly Gly Trp Val Ala Ala Gln Leu
            20                  25                  30


<210> SEQ ID NO 145
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 145

Ser Leu Met Ala Phe Thr Ala Ser Ile Thr Ser Pro Leu Ala Thr Gln
1               5                   10                  15

Tyr Thr Leu Leu Phe Asn Ile Leu Gly Gly Trp Val Ala Ala Gln Leu
            20                  25                  30


<210> SEQ ID NO 146
<211> LENGTH: 32
<212> TYPE: PRT
<213> ORGANISM: artificial sequence
<220> FEATURE:
<223> OTHER INFORMATION: anti-VHC immunogenic peptide

<400> SEQUENCE: 146

Ser Leu Met Ser Phe Thr Ala Ala Val Thr Ser Pro Leu Thr Thr Gln
1               5                   10                  15

Gln Thr Leu Leu Phe Asn Ile Leu Gly Gly Trp Val Ala Ser Gln Ile
            20                  25                  30


<210> SEQ ID NO 147
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 147

Asn Phe Ile Thr Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
```

```
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Pro
    50                  55


<210> SEQ ID NO 148
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 148

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ala Val Thr
            20                  25                  30

Ser Pro Leu Thr Thr Ser Gln Thr Leu Leu Phe Asn Ile Leu Gly Gly
        35                  40                  45

Trp Val Ala Ala Gln Leu Ala Ala Pro
    50                  55


<210> SEQ ID NO 149
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 149

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ala Val Thr
            20                  25                  30

Ser Pro Leu Thr Thr Gly Gln Thr Leu Leu Phe Asn Ile Leu Gly Gly
        35                  40                  45

Trp Val Ala Ala Gln Leu Ala Ala Pro
    50                  55


<210> SEQ ID NO 150
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 150

Asn Phe Ile Ser Gly Thr Gln Tyr Leu Ala Gly Leu Ser Thr Leu Pro
1               5                   10                  15

Gly Asn Pro Ala Ile Ala Ser Leu Met Ala Phe Thr Ala Ala Val Thr
            20                  25                  30

Ser Pro Leu Thr Thr Ser Gln Thr Leu Leu Phe Asn Ile Leu Gly Gly
        35                  40                  45

Trp Val Ala Ala Gln Leu Ala Ala Pro
    50                  55


<210> SEQ ID NO 151
<211> LENGTH: 57
<212> TYPE: PRT
<213> ORGANISM: artificial sequence
<220> FEATURE:
```

<223> OTHER INFORMATION: anti-VHC immunogenic peptide

<400> SEQUENCE: 151

Asn Phe Ile Ser Gly Ile Gln Tyr Leu Ala Gly Leu Ser Thr Leu Pro
1 5 10 15

Gly Asn Pro Ala Ile Ala Ser Leu Met Ala Phe Thr Ala Ser Ile Thr
20 25 30

Ser Pro Leu Thr Thr Gln His Thr Leu Leu Phe Asn Ile Leu Gly Gly
35 40 45

Trp Val Ala Ala Gln Leu Ala Pro Pro
50 55

<210> SEQ ID NO 152
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 152

Asn Phe Ile Ser Gly Ile Gln Tyr Leu Ala Gly Leu Ser Thr Leu Pro
1 5 10 15

Gly Asn Pro Ala Ile Ala Ser Leu Met Ala Phe Thr Ala Ser Ile Thr
20 25 30

Ser Pro Leu Thr Thr Gln Ser Thr Leu Leu Phe Asn Ile Leu Gly Gly
35 40 45

Trp Val Ala Ala Gln Leu Ala Pro Pro
50 55

<210> SEQ ID NO 153
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 153

Asn Phe Ile Ser Gly Ile Gln Tyr Leu Ala Gly Leu Ser Thr Leu Pro
1 5 10 15

Gly Asn Pro Ala Ile Ala Ser Leu Met Ala Phe Thr Ala Ser Ile Thr
20 25 30

Ser Pro Leu Thr Thr Gln Asn Thr Leu Leu Phe Asn Ile Leu Gly Gly
35 40 45

Trp Val Ala Ala Gln Leu Ala Pro Pro
50 55

<210> SEQ ID NO 154
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 154

Asn Phe Ile Ser Gly Ile Gln Tyr Leu Ala Gly Leu Ser Thr Leu Pro
1 5 10 15

Gly Asn Pro Ala Ile Ala Ser Leu Met Ala Phe Thr Ala Ser Ile Thr
20 25 30

Ser Pro Leu Thr Thr Gln Tyr Thr Leu Leu Phe Asn Ile Leu Gly Gly
35 40 45

Trp Val Ala Ala Gln Leu Ala Pro Pro 50 55

<210> SEQ ID NO 155
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 155

Asn Phe Ile Ser Gly Ile Gln Tyr Leu Ala Gly Leu Ser Thr Leu Pro
1 5 10 15

Gly Asn Pro Ala Ile Val Ser Leu Met Ala Phe Thr Ala Ser Ile Thr
20 25 30

Ser Pro Leu Thr Thr Gln His Thr Leu Leu Phe Asn Ile Leu Gly Gly
35 40 45

Trp Val Ala Ala Gln Leu Ala Pro Pro
50 55

<210> SEQ ID NO 156
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 156

Asn Phe Ile Ser Gly Ile Gln Tyr Leu Ala Gly Leu Ser Thr Leu Pro
1 5 10 15

Gly Asn Pro Ala Ile Ala Ser Leu Met Ala Phe Thr Ala Ser Val Thr
20 25 30

Ser Pro Leu Thr Thr Gln Asn Thr Leu Leu Phe Asn Ile Leu Gly Gly
35 40 45

Trp Val Ala Ala Gln Leu Ala Pro Pro
50 55

<210> SEQ ID NO 157
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 157

Asn Phe Ile Ser Gly Ile Gln Tyr Leu Ala Gly Leu Ser Thr Leu Pro
1 5 10 15

Gly Asn Pro Ala Ile Ala Ser Leu Met Ala Phe Thr Ala Ser Val Thr
20 25 30

Ser Pro Leu Thr Thr Gln Ser Thr Leu Leu Phe Asn Ile Leu Gly Gly
35 40 45

Trp Val Ala Ala Gln Leu Ala Pro Pro
50 55

<210> SEQ ID NO 158
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 158

Asn Phe Ile Ser Gly Ile Gln Tyr Leu Ala Gly Leu Ser Thr Leu Pro
1 5 10 15

```
Gly Asn Pro Ala Ile Ala Ser Leu Met Ala Phe Thr Ala Ser Ile Thr
            20                  25                  30

Ser Pro Leu Thr Thr Gln Thr Thr Leu Met Phe Asn Ile Leu Gly Gly
        35                  40                  45

Trp Val Ala Ala Gln Leu Ala Pro Pro
    50                  55


<210> SEQ ID NO 159
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 159

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Val Thr
            20                  25                  30

Ser Pro Leu Thr Thr Gln Tyr Thr Leu Leu Phe Asn Ile Leu Gly Gly
        35                  40                  45

Trp Val Ala Ala Gln Ile Ala Pro Pro
    50                  55


<210> SEQ ID NO 160
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 160

Asn Phe Ile Ser Gly Ile Gln Tyr Leu Ala Gly Leu Ser Thr Leu Pro
1               5                   10                  15

Gly Asn Pro Ala Ile Arg Ser Pro Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55


<210> SEQ ID NO 161
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 161

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Ile Gln His Thr Leu Leu Phe Asn Ile Leu Gly Gly
        35                  40                  45

Trp Val Ala Ala Gln Pro Ala Pro Pro
    50                  55


<210> SEQ ID NO 162
<211> LENGTH: 57
<212> TYPE: PRT
```

<213> ORGANISM: artificial sequence
<220> FEATURE:
<223> OTHER INFORMATION: anti-VHC immunogenic peptide

<400> SEQUENCE: 162

```
Asn Phe Ile Ser Gly Ile Gln Tyr Leu Ala Ala Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Ala
    50                  55
```

<210> SEQ ID NO 163
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 163

```
Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ser Ser Ile Thr
            20                  25                  30

Ser Pro Leu Thr Thr Gln Ser Thr Leu Leu Phe Asn Ile Leu Gly Gly
        35                  40                  45

Trp Val Ala Ala Gln Leu Ala Pro Pro
    50                  55
```

<210> SEQ ID NO 164
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 164

```
Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Ser Thr Gln Asn Thr Leu Leu Phe Asn Ile Trp Gly Gly
        35                  40                  45

Trp Val Ala Ala Gln Leu Ala Pro Pro
    50                  55
```

<210> SEQ ID NO 165
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 165

```
Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Asn Thr Leu Met Phe Asn Ile Leu Gly Gly
        35                  40                  45
```

```
Trp Val Ala Ala Gln Leu Ala Pro Pro
    50                  55


<210> SEQ ID NO 166
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 166

Asn Phe Ile Ser Gly Ile Gln Tyr Leu Ala Gly Leu Ser Thr Leu Pro
1               5                   10                  15

Gly Asn Pro Ala Met Ala Ser Leu Met Ala Phe Thr Ala Ser Ile Thr
            20                  25                  30

Ser Pro Leu Thr Thr Gln His Thr Leu Met Phe Asn Ile Leu Gly Gly
        35                  40                  45

Trp Val Ala Ala Gln Leu Ala Pro Pro
    50                  55


<210> SEQ ID NO 167
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 167

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Asn Thr Leu Leu Phe Asn Ile Leu Gly Gly
        35                  40                  45

Trp Val Ala Ala Gln Leu Ala Pro Pro
    50                  55


<210> SEQ ID NO 168
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 168

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55


<210> SEQ ID NO 169
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 169
```

```
Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Thr Thr Gln Tyr Thr Leu Leu Phe Asn Ile Leu Gly Gly
        35                  40                  45

Trp Val Ala Ala Gln Leu Ala Pro Pro
    50                  55


<210> SEQ ID NO 170
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 170

Asn Phe Ile Ser Gly Val Gln Tyr Leu Ala Gly Leu Ser Thr Leu Pro
1               5                   10                  15

Gly Asn Pro Ala Ile Ala Ser Leu Met Ala Phe Thr Ala Ser Val Thr
            20                  25                  30

Ser Pro Leu Thr Thr Gln Ser Thr Leu Leu Phe Asn Ile Leu Gly Gly
        35                  40                  45

Trp Val Ala Ala Gln Leu Ala Pro Pro
    50                  55


<210> SEQ ID NO 171
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 171

Asn Phe Ile Ser Gly Ile Gln Tyr Leu Ala Gly Leu Ser Thr Leu Pro
1               5                   10                  15

Gly Asn Leu Ala Ile Ala Ser Leu Met Ala Phe Thr Ala Ser Ile Thr
            20                  25                  30

Ser Pro Leu Thr Thr Gln His Thr Leu Leu Phe Asn Ile Leu Gly Gly
        35                  40                  45

Trp Val Ala Ala Gln Leu Ala Pro Pro
    50                  55


<210> SEQ ID NO 172
<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 172

Asn Phe Ile Ser Gly Ile Gln Tyr Leu Ala Gly Leu Ser Thr Leu Pro
1               5                   10                  15

Gly Asn Pro Ala Ile Ala Ser Leu Met Ala Phe Thr Ala Ser Ile Thr
            20                  25                  30

Ser Pro Leu Ala Thr Gln Tyr Thr Leu Leu Phe Asn Ile Leu Gly Gly
        35                  40                  45

Trp Val Ala Ala Gln Leu Ala Pro Pro
    50                  55


<210> SEQ ID NO 173
```

<211> LENGTH: 57
<212> TYPE: PRT
<213> ORGANISM: artificial sequence
<220> FEATURE:
<223> OTHER INFORMATION: anti-VHC immunogenic peptide

<400> SEQUENCE: 173

```
Asn Phe Ile Ser Gly Ile Gln Tyr Leu Ala Gly Leu Ser Thr Leu Pro
1               5                   10                  15

Gly Asn Pro Ala Ile Ala Ser Leu Met Ser Phe Thr Ala Ala Val Thr
            20                  25                  30

Ser Pro Leu Thr Thr Gln Gln Thr Leu Leu Phe Asn Ile Leu Gly Gly
        35                  40                  45

Trp Val Ala Ser Gln Ile Arg Asp Ser
    50                  55
```

<210> SEQ ID NO 174
<211> LENGTH: 29
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (1)..(1)
<223> OTHER INFORMATION: Xaa = R or Q
<220> FEATURE:
<221> NAME/KEY: MISC_FEATURE
<222> LOCATION: (3)..(3)
<223> OTHER INFORMATION: Xaa = P or A
<220> FEATURE:
<221> NAME/KEY: MISC_FEATURE
<222> LOCATION: (6)..(6)
<223> OTHER INFORMATION: Xaa = L or F
<220> FEATURE:
<221> NAME/KEY: MISC_FEATURE
<222> LOCATION: (9)..(9)
<223> OTHER INFORMATION: Xaa = F or Y
<220> FEATURE:
<221> NAME/KEY: MISC_FEATURE
<222> LOCATION: (11)..(11)
<223> OTHER INFORMATION: Xaa = D or E
<220> FEATURE:
<221> NAME/KEY: MISC_FEATURE
<222> LOCATION: (14)..(14)
<223> OTHER INFORMATION: Xaa = V or S
<220> FEATURE:
<221> NAME/KEY: MISC_FEATURE
<222> LOCATION: (20)..(20)
<223> OTHER INFORMATION: Xaa = M or R
<220> FEATURE:
<221> NAME/KEY: MISC_FEATURE
<222> LOCATION: (23)..(23)
<223> OTHER INFORMATION: Xaa = Y or H
<220> FEATURE:
<221> NAME/KEY: MISC_FEATURE
<222> LOCATION: (24)..(24)
<223> OTHER INFORMATION: Xaa = D or N
<220> FEATURE:
<221> NAME/KEY: MISC_FEATURE
<222> LOCATION: (26)..(26)
<223> OTHER INFORMATION: Xaa = V or I
<220> FEATURE:
<221> NAME/KEY: MISC_FEATURE
<222> LOCATION: (27)..(27)
<223> OTHER INFORMATION: Xaa = S, T or K
<220> FEATURE:
<221> NAME/KEY: MISC_FEATURE
<222> LOCATION: (28)..(28)
<223> OTHER INFORMATION: Xaa = T, K, I or N
<220> FEATURE:
<221> NAME/KEY: MISC_FEATURE
<222> LOCATION: (29)..(29)
<223> OTHER INFORMATION: Xaa = L or T

<400> SEQUENCE: 174

Xaa Lys Xaa Ala Arg Xaa Ile Val Xaa Pro Xaa Leu Gly Xaa Arg Val
1               5                   10                  15

Cys Glu Lys Xaa Ala Leu Xaa Xaa Val Xaa Xaa Xaa Xaa
            20                  25

<210> SEQ ID NO 175
<211> LENGTH: 44
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (4)..(4)
<223> OTHER INFORMATION: Xaa = R or Q
<220> FEATURE:
<221> NAME/KEY: MISC_FEATURE
<222> LOCATION: (6)..(6)
<223> OTHER INFORMATION: Xaa = P or A
<220> FEATURE:
<221> NAME/KEY: MISC_FEATURE
<222> LOCATION: (9)..(9)
<223> OTHER INFORMATION: Xaa = L or F
<220> FEATURE:
<221> NAME/KEY: MISC_FEATURE
<222> LOCATION: (12)..(12)
<223> OTHER INFORMATION: Xaa = F or Y
<220> FEATURE:
<221> NAME/KEY: MISC_FEATURE
<222> LOCATION: (14)..(14)
<223> OTHER INFORMATION: Xaa = D or E
<220> FEATURE:
<221> NAME/KEY: MISC_FEATURE
<222> LOCATION: (17)..(17)
<223> OTHER INFORMATION: Xaa = V or S
<220> FEATURE:
<221> NAME/KEY: MISC_FEATURE
<222> LOCATION: (23)..(23)
<223> OTHER INFORMATION: Xaa = M or R
<220> FEATURE:
<221> NAME/KEY: MISC_FEATURE
<222> LOCATION: (26)..(26)
<223> OTHER INFORMATION: Xaa = Y or H
<220> FEATURE:
<221> NAME/KEY: MISC_FEATURE
<222> LOCATION: (27)..(27)
<223> OTHER INFORMATION: Xaa = D or N
<220> FEATURE:
<221> NAME/KEY: MISC_FEATURE
<222> LOCATION: (29)..(29)
<223> OTHER INFORMATION: Xaa = V or I
<220> FEATURE:
<221> NAME/KEY: MISC_FEATURE
<222> LOCATION: (30)..(30)
<223> OTHER INFORMATION: Xaa = S, T or K
<220> FEATURE:
<221> NAME/KEY: MISC_FEATURE
<222> LOCATION: (31)..(31)
<223> OTHER INFORMATION: Xaa = T, K, I or N
<220> FEATURE:
<221> NAME/KEY: MISC_FEATURE
<222> LOCATION: (32)..(32)
<223> OTHER INFORMATION: Xaa = L or T
<220> FEATURE:
<221> NAME/KEY: MISC_FEATURE
<222> LOCATION: (33)..(33)
<223> OTHER INFORMATION: Xaa = P or A
<220> FEATURE:
<221> NAME/KEY: MISC_FEATURE
<222> LOCATION: (34)..(34)
<223> OTHER INFORMATION: Xaa = Q, L, H, R, K or P
<220> FEATURE:
<221> NAME/KEY: MISC_FEATURE
<222> LOCATION: (35)..(35)
<223> OTHER INFORMATION: Xaa = A, T, V or P
<220> FEATURE:

<221> NAME/KEY: MISC_FEATURE
<222> LOCATION: (39)..(39)
<223> OTHER INFORMATION: Xaa = P, S or A
<220> FEATURE:
<221> NAME/KEY: MISC_FEATURE
<222> LOCATION: (40)..(40)
<223> OTHER INFORMATION: Xaa = S or A
<220> FEATURE:
<221> NAME/KEY: MISC_FEATURE
<222> LOCATION: (42)..(42)
<223> OTHER INFORMATION: Xaa = G or R
<220> FEATURE:
<221> NAME/KEY: MISC_FEATURE
<222> LOCATION: (43)..(43)
<223> OTHER INFORMATION: Xaa = F or C

<400> SEQUENCE: 175

```
Lys Gly Gly Xaa Lys Xaa Ala Arg Xaa Ile Val Xaa Pro Xaa Leu Gly
1               5                   10                  15

Xaa Arg Val Cys Glu Lys Xaa Ala Leu Xaa Xaa Val Xaa Xaa Xaa Xaa
            20                  25                  30

Xaa Xaa Xaa Val Met Gly Xaa Xaa Tyr Xaa Xaa Gln
        35                  40
```

<210> SEQ ID NO 176
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 176

```
Arg Lys Pro Ala Arg Leu Ile Val Phe Pro Asp Leu Gly Val Arg Val
1               5                   10                  15

Cys Glu Lys Met Ala Leu Tyr Asp Val Val Ser Thr Leu
            20                  25
```

<210> SEQ ID NO 177
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 177

```
Arg Lys Pro Ala Arg Leu Ile Val Phe Pro Asp Leu Gly Val Arg Val
1               5                   10                  15

Cys Glu Lys Met Ala Leu Tyr Asp Val Val Ser Lys Leu
            20                  25
```

<210> SEQ ID NO 178
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 178

```
Arg Lys Pro Ala Arg Leu Ile Val Phe Pro Asp Leu Gly Val Arg Val
1               5                   10                  15

Cys Glu Lys Met Ala Leu Tyr Asp Val Val Thr Lys Leu
            20                  25
```

<210> SEQ ID NO 179
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 179

```
Gln Lys Pro Ala Arg Leu Ile Val Phe Pro Asp Leu Gly Val Arg Val
1               5                   10                  15

Cys Glu Lys Met Ala Leu Tyr Asp Val Val Ser Thr Leu
            20                  25
```

<210> SEQ ID NO 180
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 180

```
Arg Lys Ala Ala Arg Leu Ile Val Phe Pro Asp Leu Gly Val Arg Val
1               5                   10                  15

Cys Glu Lys Met Ala Leu Tyr Asp Val Val Ser Thr Leu
            20                  25
```

<210> SEQ ID NO 181
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 181

```
Arg Lys Pro Ala Arg Leu Ile Val Phe Pro Asp Leu Gly Val Arg Val
1               5                   10                  15

Cys Glu Lys Met Ala Leu Tyr Asp Val Val Ser Ile Leu
            20                  25
```

<210> SEQ ID NO 182
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 182

```
Arg Lys Pro Ala Arg Leu Ile Val Phe Pro Glu Leu Gly Val Arg Val
1               5                   10                  15

Cys Glu Lys Met Ala Leu Tyr Asp Val Val Ser Thr Leu
            20                  25
```

<210> SEQ ID NO 183
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 183

```
Arg Lys Pro Ala Arg Phe Ile Val Phe Pro Asp Leu Gly Val Arg Val
1               5                   10                  15

Cys Glu Lys Met Ala Leu Tyr Asp Val Val Ser Thr Leu
            20                  25
```

<210> SEQ ID NO 184
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 184

Arg Lys Ala Ala Arg Leu Ile Val Phe Pro Asp Leu Gly Val Arg Val
1 5 10 15

Cys Glu Lys Met Ala Leu Tyr Asn Val Val Ser Thr Leu
20 25

<210> SEQ ID NO 185
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 185

Arg Lys Pro Ala Arg Leu Ile Val Phe Pro Asp Leu Gly Val Arg Val
1 5 10 15

Cys Glu Lys Met Ala Leu Tyr Asp Val Val Ser Asn Leu
20 25

<210> SEQ ID NO 186
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 186

Arg Lys Pro Ala Arg Leu Ile Val Tyr Pro Asp Leu Gly Val Arg Val
1 5 10 15

Cys Glu Lys Met Ala Leu Tyr Asp Val Val Ser Thr Leu
20 25

<210> SEQ ID NO 187
<211> LENGTH: 29
<212> TYPE: PRT
<213> ORGANISM: artificial sequence
<220> FEATURE:
<223> OTHER INFORMATION: anti-VHC immunogenic peptide

<400> SEQUENCE: 187

Arg Lys Pro Ala Arg Leu Ile Val Tyr Pro Asp Leu Gly Ser Arg Val
1 5 10 15

Cys Glu Lys Arg Ala Leu His Asp Val Ile Lys Lys Thr
20 25

<210> SEQ ID NO 188
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 188

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Thr Leu
20 25 30

Pro Gln Ala Val Met Gly Pro Ser Tyr Gly Phe Gln
35 40

<210> SEQ ID NO 189

<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 189

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Lys Leu
20 25 30

Pro Leu Ala Val Met Gly Ser Ser Tyr Gly Phe Gln
35 40

<210> SEQ ID NO 190
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 190

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Lys Leu
20 25 30

Pro Pro Ala Val Met Gly Ser Ser Tyr Gly Phe Gln
35 40

<210> SEQ ID NO 191
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 191

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Thr Lys Leu
20 25 30

Pro Leu Ala Val Met Gly Ser Ser Tyr Gly Phe Gln
35 40

<210> SEQ ID NO 192
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 192

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Thr Leu
20 25 30

Pro Gln Ala Val Met Gly Ser Ser Tyr Gly Phe Gln
35 40

<210> SEQ ID NO 193
<211> LENGTH: 44
<212> TYPE: PRT
<213> ORGANISM: artificial sequence
<220> FEATURE:

<223> OTHER INFORMATION: anti-VHC immunogenic peptide

<400> SEQUENCE: 193

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ala Ser Tyr Gly Phe Gln
        35                  40
```

<210> SEQ ID NO 194
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 194

```
Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Val Val Met Gly Ser Ser Tyr Gly Phe Gln
        35                  40
```

<210> SEQ ID NO 195
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 195

```
Lys Gly Gly Gln Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ser Tyr Gly Phe Gln
        35                  40
```

<210> SEQ ID NO 196
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 196

```
Lys Gly Gly Arg Lys Ala Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ser Tyr Gly Phe Gln
        35                  40
```

<210> SEQ ID NO 197
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 197

-continued

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Ile Leu
20 25 30

Pro Gln Ala Val Met Gly Ser Ser Tyr Gly Phe Gln
35 40

<210> SEQ ID NO 198
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 198

Lys Gly Gly Arg Lys Pro Ala Arg Leu Ile Val Phe Pro Glu Leu Gly
1 5 10 15

Val Arg Val Cys Glu Lys Met Ala Leu Tyr Asp Val Val Ser Thr Leu
20 25 30

Pro Gln Ala Val Met Gly Ser Ser Tyr Gly Phe Gln
35 40

<210> SEQ ID NO 199
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 199

Lys Gly Gly Arg Lys Pro Ala Arg Phe Ile Val Phe Pro Asp Leu Gly
1 5 10 15

Val Arg Val Cys Glu Lys Met Ala Leu Tyr Asp Val Val Ser Thr Leu
20 25 30

Pro Lys Ala Val Met Gly Ser Ser Tyr Gly Phe Gln
35 40

<210> SEQ ID NO 200
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 200

Lys Gly Gly Arg Lys Pro Ala Arg Phe Ile Val Phe Pro Asp Leu Gly
1 5 10 15

Val Arg Val Cys Glu Lys Met Ala Leu Tyr Asp Val Val Ser Thr Leu
20 25 30

Pro Gln Ala Val Met Gly Ser Ser Tyr Gly Phe Gln
35 40

<210> SEQ ID NO 201
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 201

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Thr Leu

```
            20                  25                  30

Pro Arg Ala Val Met Gly Ser Ser Tyr Gly Cys Gln
        35                  40


<210> SEQ ID NO 202
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 202

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Pro Val Met Gly Ser Ser Tyr Gly Phe Gln
        35                  40


<210> SEQ ID NO 203
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 203

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro His Ala Val Met Gly Ser Ser Tyr Gly Phe Gln
        35                  40


<210> SEQ ID NO 204
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 204

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ala Tyr Gly Phe Gln
        35                  40


<210> SEQ ID NO 205
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 205

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Ser Ser Tyr Arg Phe Gln
        35                  40
```

```
<210> SEQ ID NO 206
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 206

Lys Gly Gly Arg Lys Ala Ala Arg Leu Ile Val Phe Pro Asp Leu Gly
1               5                   10                  15

Val Arg Val Cys Glu Lys Met Ala Leu Tyr Asp Val Val Ser Thr Leu
            20                  25                  30

Pro Gln Ala Val Met Gly Pro Ser Tyr Gly Phe Gln
        35                  40


<210> SEQ ID NO 207
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 207

Lys Gly Gly Arg Lys Ala Ala Arg Leu Ile Val Phe Pro Asp Leu Gly
1               5                   10                  15

Val Arg Val Cys Glu Lys Met Ala Leu Tyr Asn Val Val Ser Thr Leu
            20                  25                  30

Pro Gln Ala Val Met Gly Ser Ser Tyr Gly Phe Gln
        35                  40


<210> SEQ ID NO 208
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 208

Lys Gly Gly Arg Lys Pro Ala Arg Leu Ile Val Phe Pro Asp Leu Gly
1               5                   10                  15

Val Arg Val Cys Glu Lys Met Ala Leu Tyr Asp Val Val Ser Asn Leu
            20                  25                  30

Pro Gln Ala Val Met Gly Ser Ser Tyr Gly Phe Gln
        35                  40


<210> SEQ ID NO 209
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 209

Lys Gly Gly Arg Lys Pro Ala Arg Leu Ile Val Phe Pro Glu Leu Gly
1               5                   10                  15

Val Arg Val Cys Glu Lys Met Ala Leu Tyr Asp Val Val Ser Thr Leu
            20                  25                  30

Pro Gln Ala Val Met Gly Pro Ser Tyr Gly Phe Gln
        35                  40


<210> SEQ ID NO 210
<211> LENGTH: 44
```

<212> TYPE: PRT
<213> ORGANISM: artificial sequence
<220> FEATURE:
<223> OTHER INFORMATION: anti-VHC immunogenic peptide

<400> SEQUENCE: 210

Lys Gly Gly Arg Lys Pro Ala Arg Leu Ile Val Phe Pro Asp Leu Gly
1 5 10 15

Val Arg Val Cys Glu Lys Met Ala Leu Tyr Asp Val Val Ser Thr Leu
20 25 30

Pro His Thr Val Met Gly Ser Ser Tyr Gly Phe Gln
35 40

<210> SEQ ID NO 211
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 211

Lys Gly Gly Arg Lys Pro Ala Arg Leu Ile Val Tyr Pro Asp Leu Gly
1 5 10 15

Val Arg Val Cys Glu Lys Met Ala Leu Tyr Asp Val Val Ser Thr Leu
20 25 30

Pro Gln Ala Val Met Gly Ser Ser Tyr Gly Phe Gln
35 40

<210> SEQ ID NO 212
<211> LENGTH: 44
<212> TYPE: PRT
<213> ORGANISM: artificial sequence
<220> FEATURE:
<223> OTHER INFORMATION: anti-VHC immunogenic peptide

<400> SEQUENCE: 212

Lys Gly Gly Arg Lys Pro Ala Arg Leu Ile Val Tyr Pro Asp Leu Gly
1 5 10 15

Ser Arg Val Cys Glu Lys Arg Ala Leu His Asp Val Ile Lys Lys Thr
20 25 30

Ala Leu Ala Val Met Gly Ala Ala Tyr Gly Phe Gln
35 40

<210> SEQ ID NO 213
<211> LENGTH: 10
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (2)..(2)
<223> OTHER INFORMATION: Xaa = L or V
<220> FEATURE:
<221> NAME/KEY: MISC_FEATURE
<222> LOCATION: (3)..(3)
<223> OTHER INFORMATION: Xaa = L or F
<220> FEATURE:
<221> NAME/KEY: MISC_FEATURE
<222> LOCATION: (4)..(4)
<223> OTHER INFORMATION: Xaa = G or S
<220> FEATURE:
<221> NAME/KEY: MISC_FEATURE
<222> LOCATION: (5)..(5)
<223> OTHER INFORMATION: Xaa = C or T
<220> FEATURE:
<221> NAME/KEY: MISC_FEATURE
<222> LOCATION: (6)..(6)

-continued

<223> OTHER INFORMATION: Xaa = I or V
<220> FEATURE:
<221> NAME/KEY: MISC_FEATURE
<222> LOCATION: (7)..(7)
<223> OTHER INFORMATION: Xaa = I or V

<400> SEQUENCE: 213

Gly Xaa Xaa Xaa Xaa Xaa Xaa Thr Ser Leu
1 5 10

<210> SEQ ID NO 214
<211> LENGTH: 10
<212> TYPE: PRT
<213> ORGANISM: artificial sequence
<220> FEATURE:
<223> OTHER INFORMATION: anti-VHC immunogenic peptide

<400> SEQUENCE: 214

Gly Leu Leu Gly Cys Ile Ile Thr Ser Leu
1 5 10

<210> SEQ ID NO 215
<211> LENGTH: 10
<212> TYPE: PRT
<213> ORGANISM: artificial sequence
<220> FEATURE:
<223> OTHER INFORMATION: anti-VHC immunogenic peptide

<400> SEQUENCE: 215

Gly Leu Phe Gly Cys Ile Ile Thr Ser Leu
1 5 10

<210> SEQ ID NO 216
<211> LENGTH: 10
<212> TYPE: PRT
<213> ORGANISM: artificial sequence
<220> FEATURE:
<223> OTHER INFORMATION: anti-VHC immunogenic peptide

<400> SEQUENCE: 216

Gly Val Leu Gly Cys Val Ile Thr Ser Leu
1 5 10

<210> SEQ ID NO 217
<211> LENGTH: 10
<212> TYPE: PRT
<213> ORGANISM: artificial sequence
<220> FEATURE:
<223> OTHER INFORMATION: anti-VHC immunogenic peptide

<400> SEQUENCE: 217

Gly Val Leu Gly Cys Ile Ile Thr Ser Leu
1 5 10

<210> SEQ ID NO 218
<211> LENGTH: 10
<212> TYPE: PRT
<213> ORGANISM: artificial sequence
<220> FEATURE:
<223> OTHER INFORMATION: anti-VHC immunogenic peptide

<400> SEQUENCE: 218

Gly Leu Leu Gly Cys Ile Val Thr Ser Leu
1 5 10

<210> SEQ ID NO 219
<211> LENGTH: 10
<212> TYPE: PRT

<213> ORGANISM: artificial sequence
<220> FEATURE:
<223> OTHER INFORMATION: anti-VHC immunogenic peptide

<400> SEQUENCE: 219

Gly Leu Phe Gly Cys Ile Val Thr Ser Leu
1 5 10

<210> SEQ ID NO 220
<211> LENGTH: 10
<212> TYPE: PRT
<213> ORGANISM: artificial sequence
<220> FEATURE:
<223> OTHER INFORMATION: anti-VHC immunogenic peptide

<400> SEQUENCE: 220

Gly Leu Phe Ser Thr Ile Ile Thr Ser Leu
1 5 10

<210> SEQ ID NO 221
<211> LENGTH: 9
<212> TYPE: PRT
<213> ORGANISM: artificial sequence
<220> FEATURE:
<223> OTHER INFORMATION: anti-VHC immunogenic peptide
<220> FEATURE:
<221> NAME/KEY: MISC_FEATURE
<222> LOCATION: (4)..(4)
<223> OTHER INFORMATION: Xaa = T, S or A
<220> FEATURE:
<221> NAME/KEY: MISC_FEATURE
<222> LOCATION: (5)..(5)
<223> OTHER INFORMATION: Xaa = T or I
<220> FEATURE:
<221> NAME/KEY: MISC_FEATURE
<222> LOCATION: (6)..(6)
<223> OTHER INFORMATION: Xaa = Q, S or G
<220> FEATURE:
<221> NAME/KEY: MISC_FEATURE
<222> LOCATION: (7)..(7)
<223> OTHER INFORMATION: Xaa = N, Q, H, S, Y or T

<400> SEQUENCE: 221

Ser Pro Leu Xaa Xaa Xaa Xaa Thr Leu
1 5

<210> SEQ ID NO 222
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 222

Ser Pro Leu Thr Thr Gln Asn Thr Leu
1 5

<210> SEQ ID NO 223
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 223

Ser Pro Leu Thr Thr Ser Gln Thr Leu
1 5

<210> SEQ ID NO 224
<211> LENGTH: 9

<212> TYPE: PRT
<213> ORGANISM: artificial sequence
<220> FEATURE:
<223> OTHER INFORMATION: anti-VHC immunogenic peptide

<400> SEQUENCE: 224

Ser Pro Leu Thr Thr Gly Gln Thr Leu
1 5

<210> SEQ ID NO 225
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 225

Ser Pro Leu Thr Thr Gln His Thr Leu
1 5

<210> SEQ ID NO 226
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 226

Ser Pro Leu Thr Thr Gln Ser Thr Leu
1 5

<210> SEQ ID NO 227
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 227

Ser Pro Leu Thr Thr Gln Tyr Thr Leu
1 5

<210> SEQ ID NO 228
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 228

Ser Pro Leu Thr Thr Gln Thr Thr Leu
1 5

<210> SEQ ID NO 229
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 229

Ser Pro Leu Thr Ile Gln His Thr Leu
1 5

<210> SEQ ID NO 230
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 230

Ser Pro Leu Ser Thr Gln Asn Thr Leu
1               5

<210> SEQ ID NO 231
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 231

Ser Pro Leu Ala Thr Gln Tyr Thr Leu
1               5

<210> SEQ ID NO 232
<211> LENGTH: 9
<212> TYPE: PRT
<213> ORGANISM: artificial sequence
<220> FEATURE:
<223> OTHER INFORMATION: anti-VHC immunogenic peptide

<400> SEQUENCE: 232

Ser Pro Leu Thr Thr Gln Gln Thr Leu
1               5

<210> SEQ ID NO 233
<211> LENGTH: 9
<212> TYPE: PRT
<213> ORGANISM: Artificial Sequence
<220> FEATURE:
<223> OTHER INFORMATION: Synthetic Construct

<400> SEQUENCE: 233

Phe Leu Ala Thr Cys Val Asn Gly Val
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic Construct

<400> SEQUENCE: 234

Leu Leu Gly Cys Ile Ile Thr Ser Leu
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic Construct

<400> SEQUENCE: 235

Phe Leu Leu Leu Ala Asp Ala Arg Val
1               5

<210> SEQ ID NO 236
<211> LENGTH: 10
<212> TYPE: PRT
<213> ORGANISM: Artificial Sequence
<220> FEATURE:
<223> OTHER INFORMATION: Synthetic Construct -continued

<400> SEQUENCE: 236

```
Ile Leu Ala Gly Tyr Ala Gly Ala Gly Val
1               5                   10
```

<210> SEQ ID NO 237
<211> LENGTH: 9
<212> TYPE: PRT
<213> ORGANISM: Artificial Sequence
<220> FEATURE:
<223> OTHER INFORMATION: Synthetic Construct

<400> SEQUENCE: 237

```
Ala Thr Leu Gly Phe Gly Ala Tyr Met
1               5
```

<210> SEQ ID NO 238
<211> LENGTH: 9
<212> TYPE: PRT
<213> ORGANISM: Artificial Sequence
<220> FEATURE:
<223> OTHER INFORMATION: Synthetic Construct

<400> SEQUENCE: 238

```
Ala Leu Tyr Asp Val Val Ser Thr Leu
1               5
```

<210> SEQ ID NO 239
<211> LENGTH: 9
<212> TYPE: PRT
<213> ORGANISM: Artificial Sequence
<220> FEATURE:
<223> OTHER INFORMATION: Synthetic Construct

<400> SEQUENCE: 239

```
Asp Leu Met Gly Tyr Ile Pro Leu Val
1               5
```